(12) United States Patent
Kikuchi et al.

(10) Patent No.: US 11,040,937 B2
(45) Date of Patent: Jun. 22, 2021

(54) AMIDE DERIVATIVE

(71) Applicants: TOHOKU UNIVERSITY, Sendai (JP); NATIONAL UNIVERSITY CORPORATION GUNMA UNIVERSITY, Maebashi (JP); FUSO PHARMACEUTICAL INDUSTRIES, LTD., Osaka (JP)

(72) Inventors: Haruhisa Kikuchi, Sendai (JP); Yoshiteru Oshima, Sendai (JP); Toshio Hattori, Kurashiki (JP); Yuzuru Kubohara, Sakura (JP); Osamu Yamada, Kobe (JP); Jing Zhang, Osaka (JP); Yoshihisa Matsushita, Osaka (JP); Shinya Kida, Akashi (JP)

(73) Assignees: TOHOKU UNIVERSITY, Miyagi (JP); NATIONAL UNIVERSITY CORPORATION GUNMA UNIVERSITY, Gunma (JP); FUSO PHARMACEUTICAL INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/121,687

(22) PCT Filed: Feb. 27, 2015

(86) PCT No.: PCT/JP2015/055873
§ 371 (c)(1),
(2) Date: Aug. 25, 2016

(87) PCT Pub. No.: WO2015/129860
PCT Pub. Date: Sep. 3, 2015

(65) Prior Publication Data
US 2016/0368860 A1 Dec. 22, 2016

(30) Foreign Application Priority Data
Feb. 28, 2014 (JP) .............................. JP2014-038919

(51) Int. Cl.
*C07C 235/50* (2006.01)
*C07C 235/48* (2006.01)
(Continued)

(52) U.S. Cl.
CPC .......... *C07C 235/50* (2013.01); *A61K 31/165* (2013.01); *A61K 31/166* (2013.01);
(Continued)

(58) Field of Classification Search
CPC ... C07C 235/50; C07C 233/36; C07C 233/62; C07C 233/78; C07C 235/48;
(Continued)

(56) References Cited

U.S. PATENT DOCUMENTS

| 6,013,836 A | 1/2000 | Hsu et al. |
| 9,463,188 B2 | 10/2016 | Kikuchi et al. |

(Continued)

FOREIGN PATENT DOCUMENTS

| CN | 102320989 | 1/2012 |
| CN | 103613593 A | 3/2014 |

(Continued)

OTHER PUBLICATIONS

Coelho, Assessing melatonin and its oxidative metabolites amounts in biological fluid and culture medium by liquid chromatography electrospray ionization tandem mass spectrometry (LC-ESI-MS/MS), Anal. Methods, 2013, 5, pp. 6911-6918.*
(Continued)

*Primary Examiner* — Savitha M Rao
*Assistant Examiner* — Andrew P Lee
(74) *Attorney, Agent, or Firm* — Hamre, Schumann, Mueller & Larson, P.C.

(57) ABSTRACT

The present invention provides a useful medicament for the treatment and/or prophylaxis of a disease associated with the
(Continued)

enhancement of OPN production including cancer, which comprises a compound of formula:

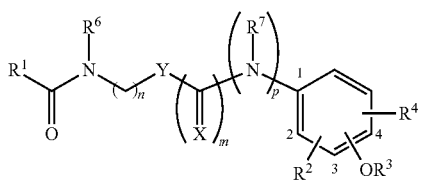

wherein $R^1$, $R^2$, $R^3$, $R^4$, $R^5$, $R^6$, $R^7$, m, n, p, X, and Y are as defined in the specification, a pharmaceutically acceptable salt thereof.

13 Claims, 5 Drawing Sheets

(51) Int. Cl.

| | |
|---|---|
| C07C 233/36 | (2006.01) |
| C07C 233/78 | (2006.01) |
| C07C 233/62 | (2006.01) |
| C07D 309/08 | (2006.01) |
| C07D 471/04 | (2006.01) |
| C07D 213/81 | (2006.01) |
| C07C 235/60 | (2006.01) |
| C07C 237/22 | (2006.01) |
| C07C 237/42 | (2006.01) |
| C07D 209/14 | (2006.01) |
| C07C 237/34 | (2006.01) |
| A61K 31/437 | (2006.01) |
| A61K 31/4045 | (2006.01) |
| A61K 31/4409 | (2006.01) |
| A61K 31/445 | (2006.01) |
| A61K 31/40 | (2006.01) |
| A61K 31/351 | (2006.01) |
| A61K 31/167 | (2006.01) |
| A61K 31/381 | (2006.01) |
| A61K 31/397 | (2006.01) |
| A61K 31/166 | (2006.01) |
| A61K 31/165 | (2006.01) |
| C07D 205/04 | (2006.01) |
| C07D 207/16 | (2006.01) |
| C07D 211/60 | (2006.01) |
| C07D 333/38 | (2006.01) |

(52) U.S. Cl.
CPC .......... *A61K 31/167* (2013.01); *A61K 31/351* (2013.01); *A61K 31/381* (2013.01); *A61K 31/397* (2013.01); *A61K 31/40* (2013.01); *A61K 31/4045* (2013.01); *A61K 31/437* (2013.01); *A61K 31/445* (2013.01); *A61K 31/4409* (2013.01); *C07C 233/36* (2013.01); *C07C 233/62* (2013.01); *C07C 233/78* (2013.01); *C07C 235/48* (2013.01); *C07C 235/60* (2013.01); *C07C 237/22* (2013.01); *C07C 237/34* (2013.01); *C07C 237/42* (2013.01); *C07D 205/04* (2013.01); *C07D 207/16* (2013.01); *C07D 209/14* (2013.01); *C07D 211/60* (2013.01); *C07D 213/81* (2013.01); *C07D 309/08* (2013.01); *C07D 333/38* (2013.01); *C07D 471/04* (2013.01); *C07C 2601/14* (2017.05)

(58) Field of Classification Search
CPC ... C07C 235/60; C07C 237/22; C07C 237/42; C07C 2601/14; A61K 31/437; A61K 31/4045; A61K 31/4409; A61K 31/445; A61K 31/40; A61K 31/351; A61K 31/167; A61K 31/381; A61K 31/397; A61K 31/166; A61K 31/165; C07D 205/04; C07D 207/16; C07D 211/60; C07D 333/38; C07D 471/04; C07D 237/34; C07D 213/81; C07D 309/08; C07D 209/14; A61P 9/10
See application file for complete search history.

(56) References Cited

U.S. PATENT DOCUMENTS

| | | |
|---|---|---|
| 2007/0054928 A1 | 3/2007 | Bannen et al. |
| 2007/0093529 A1 | 4/2007 | Finsinger et al. |
| 2009/0143445 A1 | 6/2009 | Kovach et al. |
| 2009/0326074 A1 | 12/2009 | Scott et al. |
| 2011/0280940 A1 | 11/2011 | Kiss et al. |

FOREIGN PATENT DOCUMENTS

| | | |
|---|---|---|
| JP | 349101348 | 9/1974 |
| JP | 2003128639 | 5/2003 |
| JP | 2007506777 | 3/2007 |
| JP | 2010540633 | 12/2010 |
| JP | 2011512321 | 4/2011 |
| JP | 2012505855 | 3/2012 |
| WO | 2006016218 | 2/2006 |
| WO | 2007003934 | 1/2007 |
| WO | 2010028192 | 3/2010 |
| WO | 2011032291 | 3/2011 |
| WO | 2011035143 | 3/2011 |
| WO | 2013063492 | 5/2013 |

OTHER PUBLICATIONS

Substituent effects on the stability of carbocations. Anomalous case of phenyl vs. cyclopropyl substitution, 1975, J. Am. Chem. Soc. 97, 10, pp. 2902-2904 (Year: 1975).*
The extended European Search Report issued in European application No. 15755910.5 dated Sep. 28, 2017.
Office Action issued in Chinese application No. 201580009530.5 dated Sep. 29, 2017, with its English translation.
Prasad, et al., "Synthesis and insect growth regulating activity of structurally modified benzoylphenylureas", Indian Journal of Chemistry, vol. 29B, Oct. 1, 1990, pp. 951-953, 4 pages.
Oikawa, et al., "Quantitative Structure-Activity Studies of Insect Growth Regulators", Pesticide Biochemistry and Physiology, vol. 48, pp. 135-144 (Dec. 31, 1994), 10 pages.
Barho et al., "N-Acyl Derivatives of 4-Phenoxyaniline as Neuroprotective Agents", ChemMedChem vol. 9, 2260-2273, , Jul. 17, 2014, 14 pages.
Bell, et al., "Optimization of Novel Nipecotic Bis(amide) Inhibitors of the Rho/MKL1/SRF Transcriptional Pathway as Potential Antimetastasis Agents", Bioorganic & Medicinal Chemistry Letters, vol. 23 (May 7, 2013) pp. 3826-3832, 7 pages.
STN Columbus, Chemical Abstract Service, RN:949872-95-1 et al., STN Registry database, Feb. 16, 2015, 30 pages.
Kikuchi et al."Isolation and Synthesis of a New Aromatic Compound, Brefelamide, from Dictyostelium Cellular Slime Molds and Its Inhibitory Effect on the Proliferation of Astrocytoma Cells", The Journal of Organic Chemistry, 2005, 70 (22), p. 8854-8858, particularly, p. 8856, compunds 1,9,10,1, total 5 pages.
Entrena et al. "Kynurenamines as neural nitric oxide synthase inhibitors", Journal of Medicinal Chemistry, 2005, 48 (26), p. 8174-8181, particularly, pp. 8175-8176, compounds 4a-4i, total 8 pages.

(56) References Cited

OTHER PUBLICATIONS

Moon et al. "Structure and Bioactivity of Erebusinone, a Pigment from the Antarctic Sponge *Isodictya erinacea*", Tetrahedron, 2000, 56 (46), p. 9057-9062, particularly, Figure 2, compounds 1, 4, total 6 pages.
Barho et al."N-Acyl Derivatives of 4-Phenoxyaniline as Neuroprotective Agents", Chemmedchem, Oct. 2014, 9 (10), p. 2260-2273, particularly, Table 3, compounds 23, 25, 27, total 14 pages.
Djurendic et al."Synthesis and biological evaluation of some new 2-oxazoline and salicylic acid derivatives", Arkivoc, 2011, (2), p. 83-102, particularly, Table 1, compounds 5d, 8c, p. 91, total 20 pages.
Shinya et al."Osteopontin expression inhibitory effect of brefelamide isolated from cellular slime molds and a derivative thereof", with English translation, The Pharmaceutical Society of Japan Tohoku Shibu Taikai Koen Yoshishu, Oct. 5, 2014, total 3 pages.
Senger et al. "Secreted phosphoproteins associated with neoplastic transformation: close homology with plasma proteins cleaved during blood coagulation", Cancer Research 1988; 48; 5770-5774, total 6 pages.
Brown et al."Osteopontin expression and distribution in human carcinomas", American Journal of Pathology, vol. 145, No. 3, Sep. 1994, p. 610-623, total 14 pages.
Kikuchi, "Novel biologically active compounds isolated from unexploited organisms, cellular sime molds", with English translation, the Pharmaceutical Society of Japan, 1431-1439 (2007), total 10 pages.
Honma et al."A reduction of epidermal growth factor receptor is involved in brefelamide-induced inhibition of phosphorylation of ERK in human astrocytoma cells", European Journal of Pharmacology 616 (2009) 38-42, total 5 pages.
The International Preliminary Report on Patentability of Intentional Application No. PCT/JP2015/055873, dated Oct. 7, 2016, total 19 pages.
The International Search Report of International Application No. PCT/JP2015/055873, dated Jun. 2, 2015, total 5 pages.
Mor,M. et al., Melatonin Receptor Ligands: Synthesis of New Melatonin Derivatives and Comprehensive Comparative Molecular Field Analysis (CoMFA) Study, Journal of Medicinal Chemistry, 1998, vol. 41, No. 20, p. 3831-3844.
Boyd,E.M. et al., Synthetic studies towards dendridine A: synthesis of hemi-dendridine A acetate by Fischer indolization, Tetrahedron Letters, 2012, vol. 53, No. 28, p. 3623-3626.
Database Registry, Feb. 15, 2015, RN 1647377-65-8, Retrieved from STN, international [online]; retrieved on Nov. 26, 2018; 1 page.
Database Registry, Feb. 13, 2015, RN 1646923-13-8, Retrieved from STN, international [online]; retrieved on Nov. 26, 2018; 1 page.
Database Registry, 2012, RN 1388181-34-7, RN 1387187-23-6, Retrieved from STN, international [online]; retrieved on Nov. 26, 2018; 1 page.
Database Registry, 2011, RN 1297220-12-2, RN 1285958-42-0, RN 1278166-88-3, RN 1277610-03-3, Retrieved rom STN, international [online]; retrieved on Nov. 26, 2018; 2 pages.
Database Registry, 2008, RN 1043173-43-8, RN 1011162-67-6, RN 1011159-28-6, RN 1011111-39-9, Retrieved from STN, international [online]; retrieved on Nov. 26, 2018; 2 pages.
Database Registry, 2007, RN 950104-05-9, Retrieved from STN, international [online]; retrieved on Nov. 26, 2018; 1 page.
Office Action issued in corresponding Japanese application No. 2016-505324 dated Dec. 11, 2018; 6 pages.

\* cited by examiner

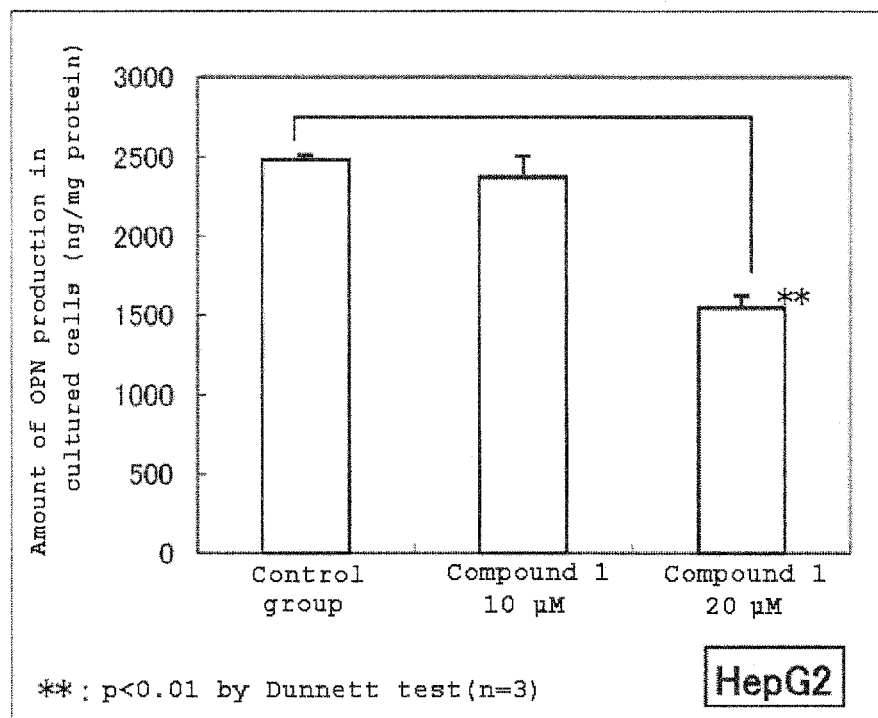
Fig.1 Inhibition of OPN production/ELISA
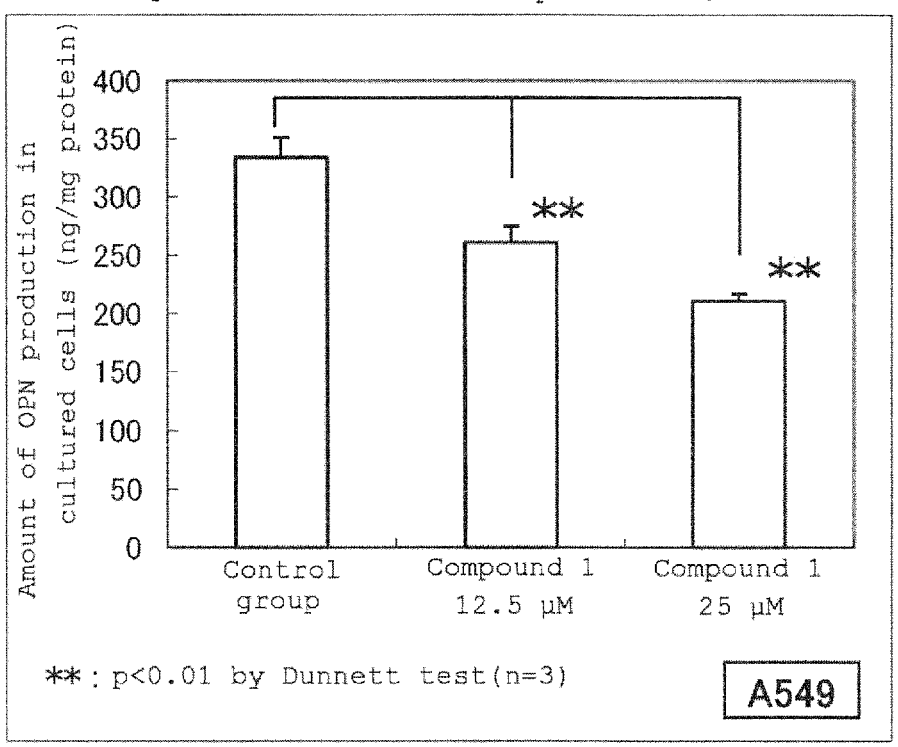
Fig.2 Inhibition of OPN production/ELISA

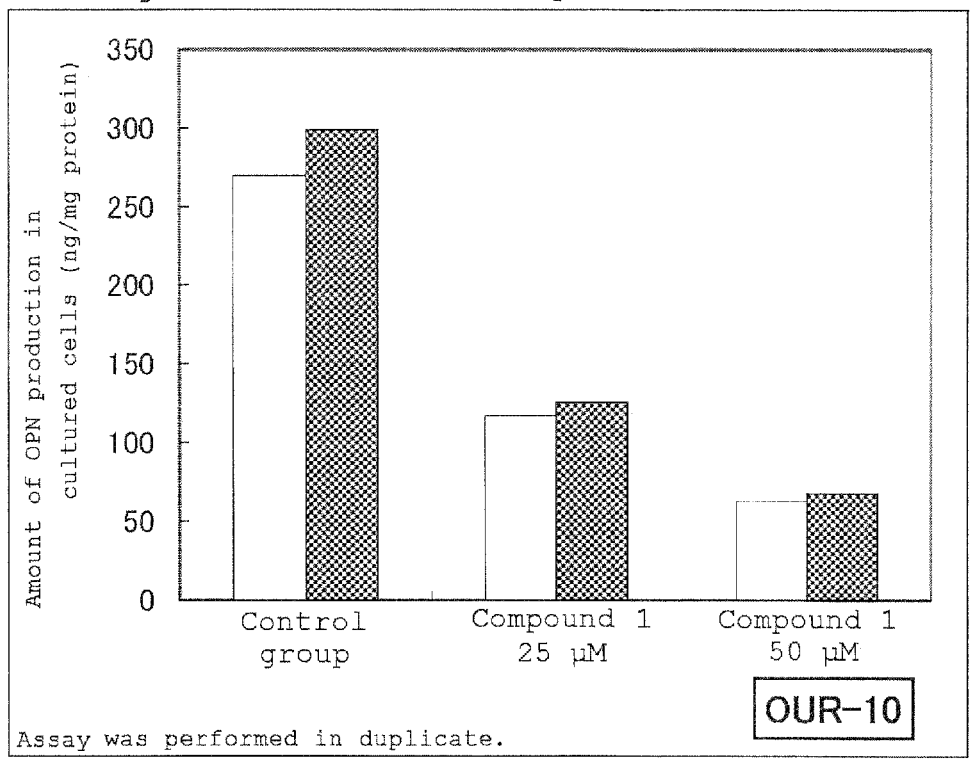
Fig. 3 Inhibition of OPN production/ELISA
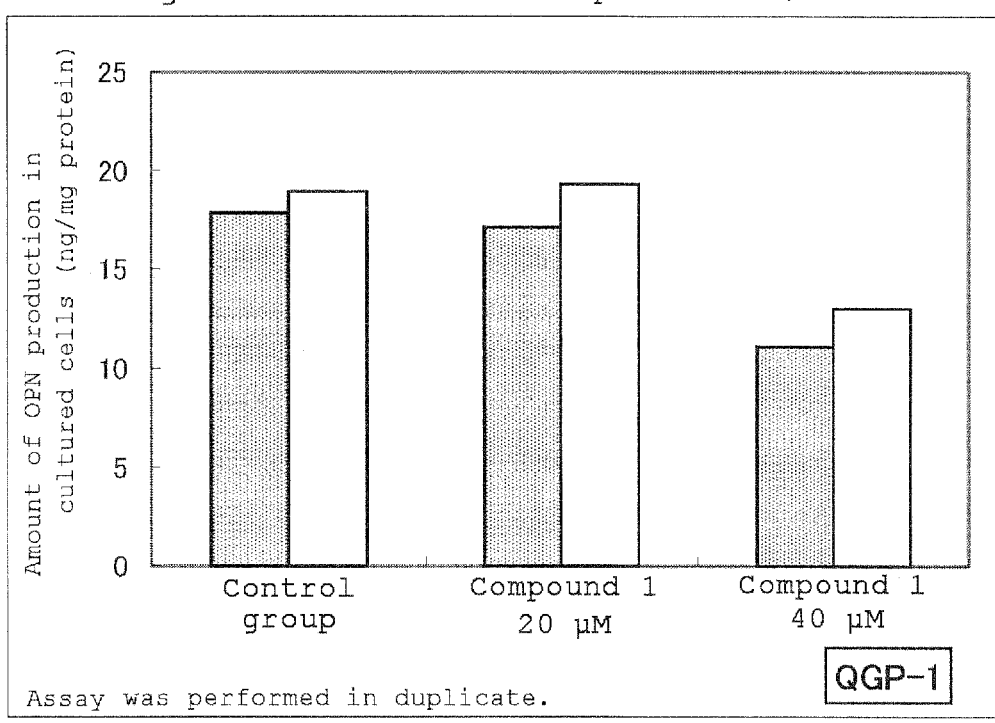
Fig. 4 Inhibition of OPN production/ELISA

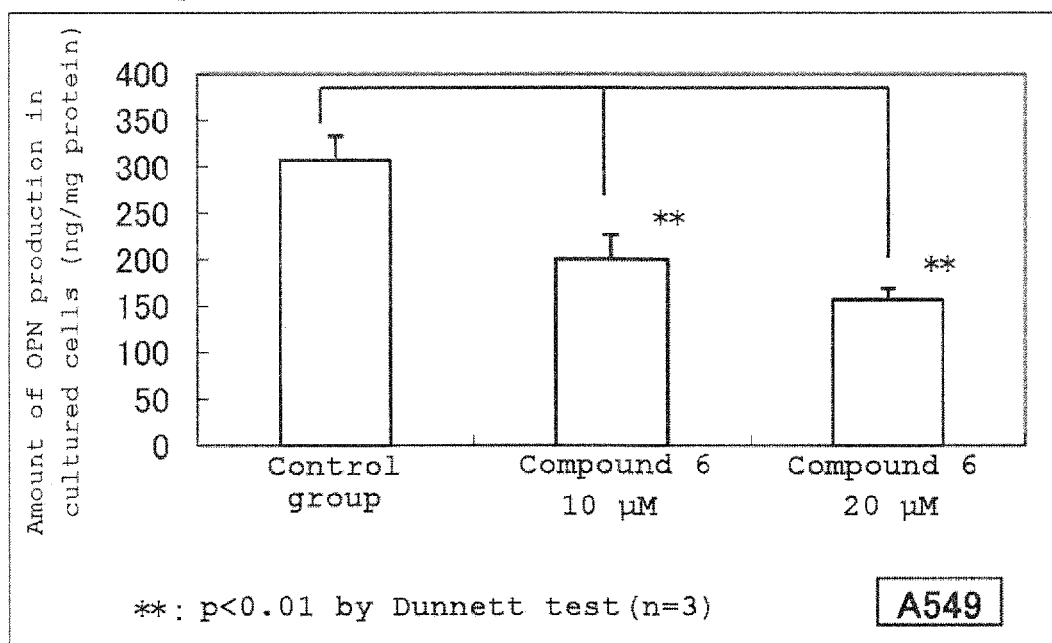
Fig.5 Inhibition of OPN production/ELISA
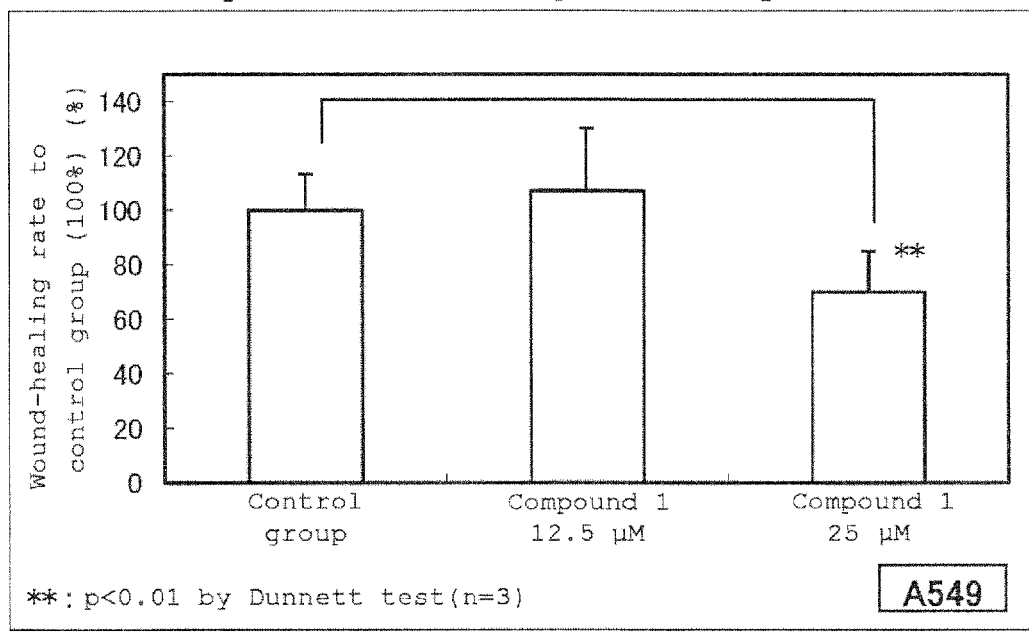
Fig.6 Wound-healing inhibitory effect

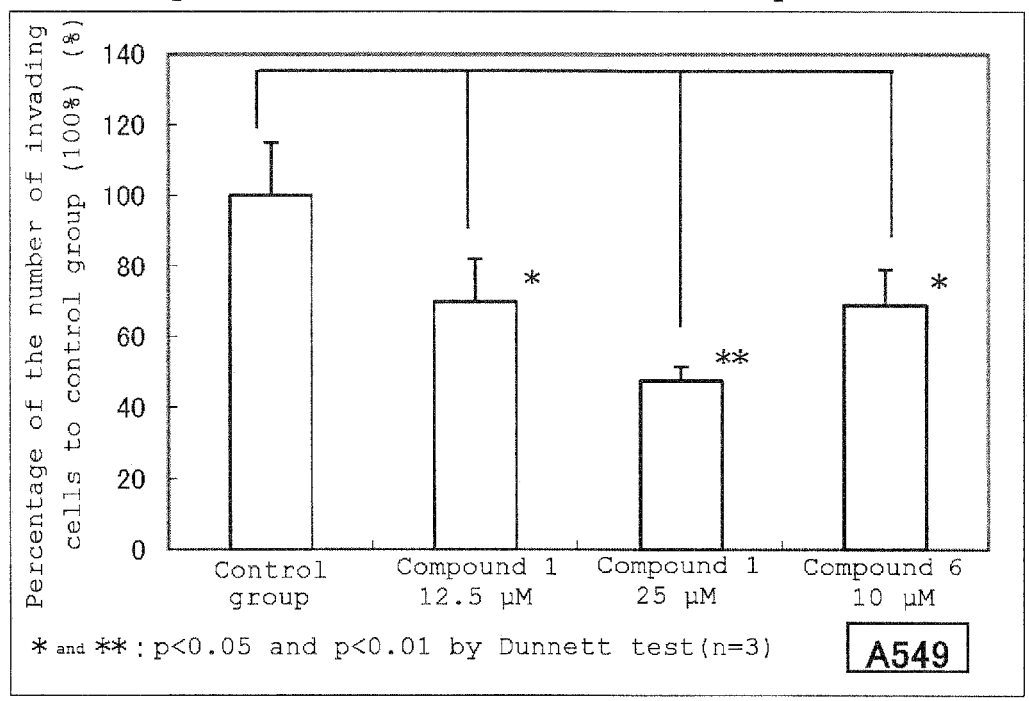
Fig.7 Matrix invasion inhibitory effect
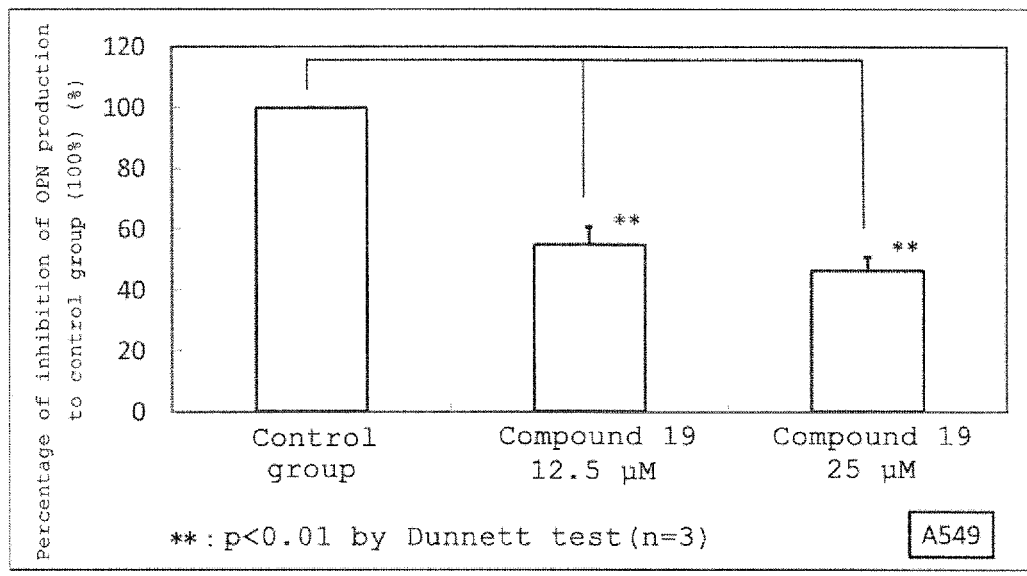
Fig.8 Inhibition of OPN production/ELISA

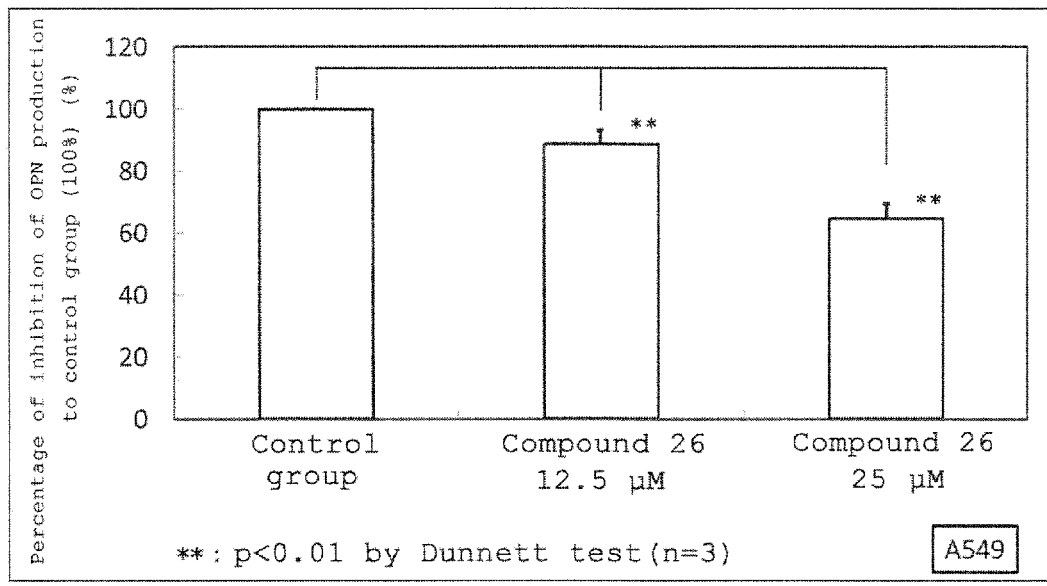
Fig. 9 Inhibition of OPN production/ELISA
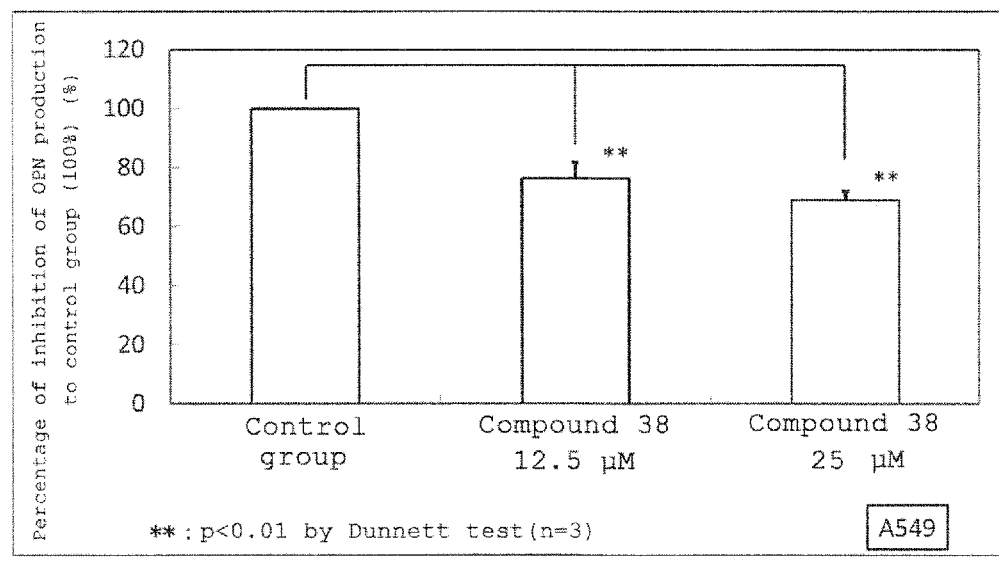
Fig. 10 Inhibition of OPN Production/ELISA

AMIDE DERIVATIVE

TECHNICAL FIELD

The present invention relates to a novel amide derivative. Also, the present invention can be useful for the treatment and/or prophylaxis of a disease associated with the enhancement of the osteopontin (OPN) production including cancer.

BACKGROUND ART

Recently, it has been found that the OPN expression correlates with the tumor progression, which suggests that OPN is associated with the metastasis of cancer. For example, it has been reported that OPN was detected from the plasma of patients suffering from lung cancer, liver cancer, breast cancer, or prostate cancer, and also the OPN mRNA expression in a cancer site was increased as compared to that of a normal site (e.g. Non-Patent Documents 1-2). As a result, it is thought that the metastasis of cancer can be prevented by inhibiting the OPN production that enhances the metastasis and infiltration of tumor cells, which can lead to a new strategy for a cancer treatment. Thus, the development of a compound for inhibiting the OPN production is expected to lead to a new therapy for various diseases including cancer.

As drugs having an inhibitory effect of the OPN production, insulin sensitizers (such as troglitazone, pioglitazone, and rosiglicazone) which are PPAR-γ (Peroxisome Proliferator-Activated Receptor-gamma) agonists, non-steroidal anti-inflammatory drugs (such as indomethacin and ibuprofen), and statin-type therapeutic drugs for hypercholesterolemia (such as rosuvatatin, simvastatin, and fluvastatin) which are HMG-CoA reductase inhibitors have been known. However, any compounds having a similar structure to that of the present invention have not been found.

On the other hand, it has been found that N-(3-(2-amino-3-(4-hydroxyphenoxy)phenyl)-3-oxopropyl)-4-hydroxybenzamide (hereinafter referred to as "brefelamide") is isolated from cellular slime mold, and inhibits cell growth by blocking the phosphorylation of ERK through reduction of epidermal growth factor receptor in human astrocytoma cells (e.g. Non-Patent References 3-5).

PRIOR ART DOCUMENTS

Non-Patent Documents

Non-Patent Reference 1: Senger D R, Perruzzi C A, Gracey C F, Papadopoulos A, Tenen D G. (1988) Secreted phosphoproteins associated with neoplastic transformation: close homology with plasma proteins cleaved during blood coagulation. Cancer Res 48, 3770-5774

Non-Patent Reference 2: Brown L F, Papadopog μ Los-Seigiou A, Brygida B, Manseau E J, Tognazzi K, Perruzzi C A, Dvorak H F, Senger D R. (1994) Osteopontin expression in human carcinoma. Am J Pathol. 145, 610-623

Non-Patent Reference 3: Kikuchi H. at al., J. Org. Chem., 70, 8854-8858 (2005)

Non-Patent Reference 4: Kikuchi H., YAKUGAKU ZASSHI 127(9) 1431-1439 (2007)

Non-Patent Reference 5: Shigeyoshi Honma et al., European Journal of Pharmacology, 616 (2009) 38-42

SUMMARY OF INVENTION

Problem to be Solved by the Invention

An object of the present invention is to find a novel compound having an inhibitory effect of the OPN production and to provide a useful medicament for the treatment and/or prophylaxis of a disease associated with the enhancement of the OPN production including cancer.

(Means for Solving the Problems)

The present inventors have extensively studied to reach the above object, and then have found that brefelamide isolated from cellular slime mold has an inhibitory effect of the OPN production and also that compound of the following formula which is a brefelamide derivative has a potent inhibitory effect of the OPN production. Based upon the new findings, the present invention has been completed. The present invention relates to an amide derivative of the following formula (including brefelamide) or a pharmaceutically acceptable salt thereof (hereinafter referred to as "the present compound", as necessary) and a medical use of the derivative having an inhibitory effect of the OPN production.

The present invention provides inventions of various embodiments described below.

[1] A compound of formula:

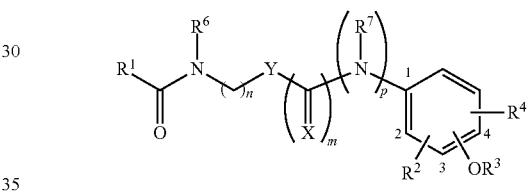

wherein $R^1$ and $R^3$ are independently hydrogen atom, $C_{1-6}$ alkyl, $C_{2-6}$ alkenyl, $C_{2-6}$ alkynyl, $C_{3-8}$ cycloalkyl, $C_{3-8}$ heterocycloalkyl, $C_{6-10}$ aryl, or 5- to 10-membered heteroaryl wherein the $C_{1-6}$ alkyl, $C_{2-6}$ alkenyl, $C_{2-6}$ alkynyl, $C_{3-8}$ cycloalkyl, $C_{3-8}$ heterocycloalkyl, $C_{6-10}$ aryl, and 5- to 10-membered heteroaryl independently may be optionally substituted with one group or the same or different two or more groups selected independently from the group consisting of halogen, hydroxy, mercapto, cyano, nitro, amino, mono- or di-$C_{1-6}$ alkylamino, $C_{1-4}$ acyl, $C_{1-4}$ acylamino, $C_{1-4}$ alkylsulfonyl, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and —$OR^5$ at any replaceable positions;

$R^2$ is hydrogen atom, amino, amino substituted with one or two independently-selected $C_{1-6}$ alkyl, hydroxy, or $C_{1-6}$ alkoxy;

$R^4$ is hydrogen atom, halogen, amino, amino substituted with one or two independently-selected $C_{1-6}$ alkyl, $C_{1-6}$ alkyl, or $C_{1-6}$ haloalkyl;

$R^5$ is $C_{2-6}$ alkenyl, $C_{2-6}$ alkynyl, $C_{3-8}$ cycloalkyl, $C_{3-8}$ heterocycloalkyl, aryl, or 5- to 10-membered heteroaryl wherein the $C_{2-6}$ alkenyl, $C_{2-6}$ alkynyl, cycloalkyl, $C_{3-8}$ heterocycloalkyl, $C_{6-10}$ aryl, and 5- to 10-membered heteroaryl may be optionally substituted with one group or the same or different two or more groups selected independently from the group consisting of halogen, hydroxy, mercapto, cyano, nitro, amino, mono- or di-$C_{1-6}$ alkylamino, $C_{1-4}$ acyl, $C_{1-4}$ acylamino, $C_{1-4}$ alkylsulfoxy, $C_{1-6}$ alkyl, $C_{1-6}$ haloalkyl, $C_{1-6}$ alkoxy, $C_{1-6}$ haloalkoxy, $C_{2-6}$ alkenyl, and $C_{2-6}$ alkynyl at any replaceable positions;

$R^6$ and $R^7$ are independently hydrogen atom or $C_{1-4}$ alkyl;
n is 0 to 4, provided that when n is 1 to 4 and $R^6$ is $C_{1-4}$ alkyl, the terminal carbon atom of $R^6$ may be combined with any one carbon atom of the alkylene group in the parenthesis for n to form a 4- to 6-membered ring;
m is 0 or 1;
p is 0 or 1;
X is O, or when p is 0 and $R^2$ is amino or substituted amino which is linked at the 2-position of the benzene ring, X may be CH connecting the nitrogen atom in $R^2$ to form a pyrrole ring; and
Y is $CH_2$ or NH;
or a pharmaceutically acceptable salt thereof, provided that the following compound is excluded:
N-(3-(2-amino-3-(4-hydroxyphenoxy)phenyl)-3-oxopropyl)-4-hydroxybenzamide.

[2] The compound according to the above [1] represented by formula (I):

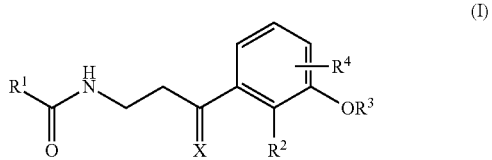

(I)

wherein $R^1$, $R^2$, $R^3$, $R^4$, and X are as defined in the above [1], or a pharmaceutically acceptable salt thereof.

[3] The compound according to the above [1] or [2], or a pharmaceutically acceptable salt thereof wherein $R^1$ is $C_{3-8}$ cycloalkyl, $C_{3-8}$ heterocycloalkyl, $C_{6-10}$ aryl, or 5- to 10-membered heteroaryl wherein the $C_{3-8}$ cycloalkyl, $C_{3-8}$ heterocycloalkyl, $C_{6-10}$ aryl, and 5- to 10-membered heteroaryl may be optionally substituted with one group or the same or different two or more groups selected independently from the group consisting of halogen, hydroxy, amino, mono- or di-$C_{1-6}$ alkylamino, $C_{1-4}$ acyl, $C_{1-4}$ acylamino, $C_{1-6}$ alkyl, $C_{1-6}$ haloalkyl, $C_{1-6}$ alkoxy, and $C_{1-6}$ haloalkoxy at any replaceable positions;
$R^2$ is hydrogen atom, amino, or hydroxy which is linked at the 2-position of the benzene ring;
$OR^3$ is linked at the 3-position of the benzene ring, and $R^3$ is phenyl which may be optionally substituted with one group or the same or different two or more groups selected independently from the group consisting of halogen, hydroxy, $C_{1-6}$ alkyl, $C_{1-6}$ haloalkyl, $C_{1-6}$ alkoxy, and $C_{1-6}$ haloalkoxy at any replaceable positions; and
$R^4$ is hydrogen atom, halogen, or amino.

[4] The compound according to any one of the above [1] to [3] or a pharmaceutically acceptable salt thereof wherein $R^1$ is $C_{3-8}$ cycloalkyl, tetrahydropyranyl, pyridyl, thienyl, or phenyl wherein the $C_{3-8}$ cycloalkyl, tetrahydropyranyl, pyridyl, thienyl, and phenyl may be optionally substituted with one group or the same or different two or more groups selected independently from the group consisting of halogen, hydroxy, amino, $C_{1-4}$ acyl, $C_{1-4}$ acylamino, $C_{1-6}$ alkyl, $C_{1-6}$ haloalkyl, $C_{1-6}$ alkoxy, and $C_{1-6}$ haloalkoxy at any replaceable positions.

[5] The compound according to any one of the above [1] to [4] or a pharmaceutically acceptable salt thereof wherein $R^1$ is phenyl which is substituted with the group(s) selected independently from halogen, hydroxy, amino, $C_{1-4}$ acylamino, or $C_{1-6}$ alkoxy at the 3- and/or 4-position(s).

[6] The compound according to any one of the above [1] to [5] or a pharmaceutically acceptable salt thereof wherein $R^3$ is phenyl which is substituted with the group(s) selected independently from halogen, hydroxy, $C_{1-6}$ alkyl, $C_{1-6}$ haloalkyl, $C_{1-6}$ alkoxy, or $C_{1-6}$ haloalkoxy at the 3- and/or 4-position(s).

[7] The compound according to any one of the above [1] to [6] or a pharmaceutically acceptable salt thereof wherein $R^4$ is hydrogen atom.

[8] The compound according to any one of the above [1] to [7] or a pharmaceutically acceptable salt thereof wherein it is 1 and X is O.

[9] The compound according to any one of the above [1] to [7] or a pharmaceutically acceptable salt thereof wherein m is 1, X is O, and p is 1.

[10] The compound according to any one of the above [1] to [9] or a pharmaceutically acceptable salt thereof wherein n is 1 to 4, and $R^6$ is $C_{1-4}$ alkyl and further the terminal carbon atom of $R^6$ is combined with any one carbon atom of the alkylene group in the parenthesis for n to form a 4- to 6-membered ring.

[11] The compound according to any one of the above [1] to [10] which is selected from the group consisting of:
4-hydroxy-N-(2-(7-(4-hydroxyphenoxy)-1H-indol-3-yl)ethyl)benzamide (Compound 2);
N-(3-(2,3-dihydroxyphenyl)-3-oxopropyl)-4-(4-hydroxyphenoxy)benzamide (Compound 3);
N-(3-(2-amino-3-(4-hydroxyphenoxy)phenyl)-3-oxopropyl)-4-methoxybenzamide (Compound 4);
N-(3-(2-amino-3-(4-methoxyphenoxy)phenyl)-3-oxopropyl)-4-methoxybenzamide (Compound 5);
N-(3-(2-amino-3-(4-methoxyphenoxy)phenyl)-3-oxopropyl)-4-hydroxybenzamide (Compound 6);
N-(3-(2-amino-3-(4-hydroxyphenoxy)phenyl)-3-oxopropyl)-3-methoxybenzamide (Compound 7);
N-(3-(2-amino-3-(4-hydroxyphenoxy)phenyl)-3-oxopropyl)-acetamide (Compound 8);
N-(3-(2-amino-3-(4-hydroxyphenoxy)phenyl)-3-oxopropyl)-4-fluorobenzamide (Compound 9);
N-(3-(2-amino-3-(4-hydroxyphenoxy)phenyl)-3-oxopropyl)-cyclohexanecarboxamide (Compound 10);
N-(3-(2-amino-3-(4-hydroxyphenoxy)phenyl)-3-oxopropyl)-(tetrahydro-2H-pyran-4-yl)-carboxamide (Compound 11);
N-(3-(2-amino-3-methoxyphenyl)-3-oxopropyl)-4-hydroxybenzamide (Compound 12);
N-(3-(2-amino-3-hydroxyphenyl)-3-oxopropyl)-4-hydroxybenzamide (Compound 13);
N-(3-(2-amino-3-(4-methylphenoxy)phenyl)-3-oxopropyl)-4-hydroxybenzamide (Compound 14);
N-(3-(2-amino-3-(4-(trifluoromethyl)phenoxy)phenyl)-3-oxopropyl)-4-hydroxybenzamide (Compound 15);
N-(3-(2-amino-3-(3,4-dimethoxyphenoxy)phenyl)-3-oxopropyl)-4-hydroxybenzamide (Compound 16);
N-(3-(2-amino-3-(4-chlorophenoxy)phenyl)-3-oxopropyl)-4-hydroxybenzamide (Compound 17);
N-(3-(2-amino-3-(4-chlorophenoxy)phenyl)-3-oxopropyl)-4-aminobenzamide (Compound 19);
N-(3-(2-amino-3-(4-chlorophenoxy)phenyl)-3-oxopropyl)-4-acetylaminobenzamide (Compound 20);
N-(2-(3-(4-methoxyphenoxy)benzoylamino)ethyl)-4-hydroxybenzamide (Compound 21);
N-(2-(2-(4-methoxyphenoxy)benzoylamino)ethyl)-4-hydroxybenzamide (Compound 22);
N-(4-hydroxyphenyl)-4-(3-(4-chlorophenoxy)phenylamino)-4-oxobutanamide (Compound 23);

N-(3-(3-(4-chlorophenoxy)phenylamino)-3-oxopropyl)-4-hydroxybenzamide (Compound 24);
N-(2-(3-(4-methoxyphenoxy)phenylamino)-2-oxyethyl)-4-hydroxybenzamide (Compound 25);
N-(3-(3-(4-methoxyphenoxy)phenylamino)-3-oxopropyl)-4-hydroxybenzamide (Compound 26)
N-(4-(3-(4-methoxyphenoxy)phenylamino)-4-oxobuthyl)-4-hydroxybenzamide (Compound 27)
N-(2-(2-(4-methoxyphenoxy)phenylamino)-2-oxoethyl)-4-hydroxybenzamide (Compound 28);
N-(3-(2-(4-methoxyphenoxy)phenylamino)-3-oxopropyl)-4-hydroxybenzamide (Compound 29);
N-(3-(4-(4-methoxyphenoxy)phenylamino)-3-oxopropyl)-4-hydroxybenzamide (Compound 30);
N-(3-(4-chlorophenoxy)phenyl)-1-(4-hydroxyphenylcarbonyl)azetidine-3-carboxamide (Compound 31);
N-(3-(4-chlorophenoxy)phenyl)-1-(4-hydroxyphenylcarbonyl)pyrrolidine-3-carboxamide (Compound 32);
N-(3-(4-chlorophenoxy)phenyl)-1-(4-hydroxyphenylcarbonyl)piperidine-3-carboxamide (Compound 33);
N-(3-(4-chlorophenoxy)phenyl)-1-(4-hydroxyphenylcarbonyl)pyrrolidine-2-carboxamide (Compound 34);
N-(3-(3-(4-chlorophenoxy)phenylamino)-3-oxopropyl)thiophene-2-carboxamide (Compound 35);
N-(3-(3-(4-chlorophenoxy)phenylamino)-3-oxopropyl)thiophene-3-carboxamide (Compound 36);
N-(3-(3-(4-chlorophenoxy)phenylamino)-3-oxopropyl)pyridine-4-carboxamide (Compound 37); and
N-(3-(3-(3,4-dichlorophenoxy)phenylamino)-3-oxopropyl)-4-hydroxybenzamide (Compound 38);
or a pharmaceutically acceptable salt thereof.

[12] A pharmaceutical composition comprising the compound according to any one of the above [1] to [11] or a pharmaceutically acceptable salt thereof and a pharmaceutically acceptable additive.

[13] The pharmaceutical composition according to the above [12] for use in the treatment of a disease associated with the enhancement of the osteopontin production.

[14] A medicament for treating a disease associated with the enhancement of the osteopontin production, comprising a compound of formula:

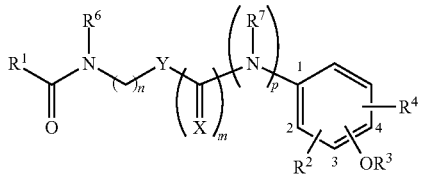

wherein
$R^1$ and $R^3$ are independently hydrogen atom, $C_{1-6}$ alkyl, $C_{2-6}$ alkenyl, $C_{2-6}$ alkynyl, $C_{3-8}$ cycloalkyl, $C_{3-8}$ heterocycloalkyl, $C_{6-10}$ aryl, or 5- to 10-membered heteroaryl wherein the $C_{1-6}$ alkyl, $C_{2-6}$ alkenyl, $C_{2-6}$ alkynyl, $C_{3-8}$ cycloalkyl, $C_{3-8}$ heterocycloalkyl, $C_{6-10}$ aryl, and 5- to 10-membered heteroaryl independently may be optionally substituted with one group or the same or different two or more groups selected independently from the group consisting of halogen, hydroxy, mercapto, cyano, nitro, amino, mono- or di-$C_{1-6}$ alkylamino, $C_{1-4}$ acyl, $C_{1-4}$ acylamino, $C_{1-4}$ alkylsulfonyl, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and —$OR^5$ at any replaceable positions;

$R^2$ is hydrogen atom, amino, amino substituted with one or two independently-selected $C_{1-6}$ alkyl, hydroxy, or $C_{1-6}$ alkoxy;

$R^4$ is hydrogen atom, halogen, amino, amino substituted with one or two independently-selected $C_{1-6}$ alkyl, $C_{1-6}$ alkyl, or $C_{1-6}$ haloalkyl;

$R^5$ is $C_{2-6}$ alkenyl, $C_{2-6}$ alkynyl, $C_{3-8}$ cycloalkyl, $C_{3-8}$ heterocycloalkyl, $C_{6-10}$ aryl, or 5- to 10-membered heteroaryl, wherein the $C_{2-6}$ alkenyl, $C_{2-6}$ alkynyl, $C_{3-8}$ cycloalkyl, $C_{3-8}$ heterocycloalkyl, $C_{6-10}$ aryl, and 5- to 10-membered heteroaryl may be optionally substituted with one group or the same or different two or more groups selected independently from the group consisting of halogen, hydroxy, mercapto, cyano, nitro, amino, mono- or di-$C_{1-6}$ alkylamino, $C_{1-4}$ acyl, $C_{1-4}$ acylamino, $C_{1-4}$ alkylsulfoxy, $C_{1-6}$ alkyl, $C_{1-6}$ haloalkyl, $C_{1-6}$ alkoxy, $C_{1-6}$ haloalkoxy, $C_{2-6}$ alkenyl, and $C_{2-6}$ alkynyl;

$R^6$ and $R^7$ are independently hydrogen atom or $C_{1-4}$ alkyl;

n is 0 to 4, provided that when n is 1 to 4 and $R^6$ is $C_{1-4}$ alkyl, the terminal carbon atom of $R^6$ may be combined with any one carbon atom of the alkylene group in the parenthesis for n to form a 4- to 6-membered ring;

m is 0 or 1;
p is 0 or 1;
X is O, or when p is 0 and $R^2$ is amino or substituted amino which is linked at the 2-position of the benzene ring, X may be CH connecting the nitrogen atom in $R^2$ to form a pyrrole ring; and
Y is $CH_2$ or NH;
or a pharmaceutically acceptable salt thereof as an active ingredient.

[15] The medicament according to the above [14] wherein the compound represented by the formula is a compound of formula (I):

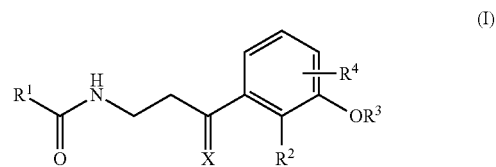

wherein $R^1$, $R^2$, $R^3$, $R^4$, and X are as defined in the above [14].

[16] The medicament according to the above [14] or [15] wherein $R^1$ is $C_{3-8}$ cycloalkyl, $C_{3-8}$ heterocycloalkyl, $C_{6-10}$ aryl, or 5- to 10-membered heteroaryl wherein the $C_{3-8}$ cycloalkyl, $C_{3-8}$ heterocycloalkyl, $C_{6-10}$ aryl, and 5- to 10-membered heteroaryl may be optionally substituted with one group or the same or different two or more groups selected independently from the group consisting of halogen, hydroxy, amino, mono- or di-$C_{1-6}$ alkylamino, $C_{1-4}$ acyl, acylamino, $C_{1-6}$ alkyl, $C_{1-6}$ haloalkyl, $C_{1-6}$ alkoxy, and $C_{1-6}$ haloalkoxy at any replaceable positions;

$R^2$ is hydrogen atom, amino, or hydroxy which is linked at the 2-position of the benzene ring;

$OR^3$ is linked at the 3-position of the benzene ring, and $R^3$ is phenyl which may be optionally substituted with one group or the same or different two or more groups selected independently from the group consisting of halogen, hydroxy, $C_{1-6}$ alkyl, $C_{1-6}$haloalkyl, $C_{1-6}$ alkoxy, and $C_{1-6}$ haloalkoxy at any replaceable positions; and $R^4$ is hydrogen atom, halogen, or amino.

[17] The medicament according to any one of the above [14] to [16] wherein $R^1$ is $C_{3-8}$ cycloalkyl, tetrahydropyranyl, pyridyl, thienyl, or phenyl wherein the $C_{3-4}$ cycloalkyl, tetrahydropyranyl, pyridyl, thienyl, and phenyl may be optionally substituted with one group or the same or different two or more groups selected independently from the group consisting of halogen, hydroxy, amino, $C_{1-4}$ acyl, $C_{1-4}$ acylamino, $C_{1-6}$ alkyl, $C_{1-6}$ haloalkyl, $C_{1-6}$ alkoxy, and $C_{1-6}$ haloalkoxy at any replaceable positions.

[18] The medicament according to any one of the above [14] to [17], wherein $R^1$ is phenyl which is substituted with the group(s) selected independently from halogen, hydroxy, amino, $C_{1-4}$ acylamino, or $C_{1-6}$ alkoxy at the 3- and/or 4-position(s).

[19] The medicament according to any one of the above [14] to [18] wherein $R^3$ is phenyl which is substituted with the group(s) selected independently from halogen, hydroxy, $C_{1-6}$ alkyl, $C_{1-6}$ haloalkyl, $C_{1-6}$ alkoxy, and/or $C_{1-6}$ haloalkoxy at the 3- and/or 4-position(s).

[20] The medicament according to any one of the above [14] to [19] wherein $R^4$ is hydrogen atom.

[21] The medicament according to any one of the above [14] to [20] wherein m is 1 and X is O.

[22] The medicament according to any one of the above [14] to [20] wherein m is 1, X is O, and p is 1.

[23] The medicament according to any one of the above [14] to [22] wherein n is 1 to 4, and $R^6$ is $C_{1-4}$ alkyl and further the terminal carbon atom of $R^6$ is combined with any one carbon of the alkylene group in the parenthesis for n to form a 4- to 6-membered ring.

[24] The medicament according to any one of the above [14] to [23] wherein the compound is selected from the group consisting of:

N-(3-(2-amino-3-(4-hydroxyphenoxy)phenyl)-3-oxopropyl)-4-hydroxybenzamide (Compound 1);
4-hydroxy-N-(2-(7-(4-hydroxyphenoxy)-1H-indol-3-yl)ethyl)benzamide (Compound 2);
N-(3-(2,3-dihydroxyphenyl)-3-oxopropyl)-4-(4-hydroxyphenoxy)benzamide (Compound 3);
N-(3-(2-amino-3-(4-hydroxyphenoxy)phenyl)-3-oxopropyl)-4-methoxybenzamide (Compound 4);
N-(3-(2-amino-3-(4-methoxyphenoxy)phenyl)-3-oxopropyl)-4-methoxybenzamide (Compound 5);
N-(3-(2-amino-3-(4-methoxyphenoxy)phenyl)-3-oxopropyl)-4-hydroxybenzamide (Compound 6);
N-(3-(2-amino-3-(4-hydroxyphenoxy)phenyl)-3-oxopropyl)-3-methoxybenzamide (Compound 7);
N-(3-(2-amino-3-(4-hydroxyphenoxy)phenyl)-3-oxopropyl)-acetamide (Compound 8);
N-(3-(2-amino-3-(4-hydroxyphenoxy)phenyl)-3-oxopropyl)-4-fluorobenzamide (Compound 9);
N-(3-(2-amino-3-(4-hydroxyphenoxy)phenyl)-3-oxopropyl)-cyclohexanecarboxamide (Compound 10);
N-(3-(2-amino-3-(4-hydroxyphenoxy)phenyl)-3-oxopropyl)-(tetrahydro2H-pyran-4-yl)-carboxamide (Compound 11);
N-(3-(2-amino-3-methoxyphenyl)-3-oxopropyl)-4-hydroxybenzamide (Compound 12);
N-(3-(2-amino-3-hydroxyphenyl)-3-oxopropyl)-4-hydroxybenzamide (Compound 13);
N-(3-(2-amino-3-(4-methylphenoxy)phenyl)-3-oxopropyl)-4-hydroxybenzamide (Compound 14);
N-(3-(2-amino-3-(4-(trifluoromethyl)phenoxy)phenyl)-3-oxopropyl)-4-hydroxybenzamide (Compound 15);
N-(3-(2-amino-3-(3,4-dimethoxyphenoxy)phenyl)-3-oxopropyl)-4-hydroxybenzamide (Compound 16);
N-(3-(2-amino-3-(4-chlorophenoxy)phenyl)-3-oxopropyl)-4-hydroxybenzamide (Compound 17);
N-(3-(2-amino-3-(4-chlorophenoxy)phenyl)-3-oxopropyl)-4-aminobenzamide (Compound 19);
N-(3-(2-amino-3-(4-chlorophenoxy)phenyl)-3-oxopropyl)-4-acetylaminobenzamide (Compound 20);
N-(2-(3-(4-methoxyphenoxy)benzoylamino)ethyl)-4-hydroxybenzamide (Compound 21);
N-(2-(2-(4-methoxyphenoxy)benzoylamino)ethyl)-4-hydroxybenzamide (Compound 22);
N-(4-hydroxyphenyl)-4-(3-(4-chlorophenoxy)phenylamino)-4-oxobutanamide (Compound 23);
N-(3-(3-(4-chlorophenoxy)phenylamino)-3-oxopropyl)-4-hydroxybenzamide (Compound 24);
N-(2-(3-(4-methoxyphenoxy)phenylamino)-2-oxyethyl)-4-hydroxybenzamide (Compound 25);
N-(3-(3-(4-methoxyphenoxy)phenylamino)-3-oxopropyl)-4-hydroxybenzamide (Compound 26);
N-(4-(3-(4-methoxyphenoxy)phenylamino)-4-oxobuthyl)-4-hydroxybenzamide (Compound 27);
N-(2-(2-(4-methoxyphenoxy)phenylamino)-2-oxoethyl)-4-hydroxybenzamide (Compound 28);
N-(3-(2-(4-methoxyphenoxy)phenylamino)-3-oxopropyl)-4-hydroxybenzamide (Compound 29);
N-(3-(4-(4-methoxyphenoxy)phenylamino)-3-oxopropyl)-4-hydroxybenzamide (Compound 30);
N-(3-(4-chlorophenoxy)phenyl)-1-(4-hydroxyphenylcarbonyl)azetidine-3-carboxamide (Compound 31);
N-(3-(4-chlorophenoxy)phenyl)-1-(4-hydroxyphenylcarbonyl)pyrrolidine-3-carboxamide (Compound 32);
N-(3-(4-chlorophenoxy)phenyl)-1-(4-hydroxyphenylcarbonyl)piperidine-3-carboxamide (Compound 33);
N-(3-(4-chlorophenoxy)phenyl)-1-(4-hydroxyphenylcarbonyl)pyrrolidine-2-carboxamide (Compound 34);
N-(3-(3-(4-chlorophenoxy)phenylamino)-3-oxopropyl)thiophene-2-carboxamide (Compound 35);
N-(3-(3-(4-chlorophenoxy)phenylamino)-3-oxopropyl)thiophene-3-carboxamide (Compound 36);
N-(3-(3-(4-chlorophenoxy)phenylamino)-3-oxopropyl)pyridine-4-carboxamide (Compound 37); and
N-(3-(3-(3,4-dichlorophenoxy)phenylamino)-3-oxopropyl)-4-hydroxybenzamide (Compound 38).

[25] A medicament for treating a disease associated with the enhancement of the osteopontin production, comprising N-(3-(2-amino-3-(4-hydroxyphenoxy)phenyl)-3-oxopropyl)-4-hydroxybenzamide or a pharmaceutically acceptable salt thereof.

[26] The medicament according to any one of the above [14] to [25] wherein the disease is cancer, hepatitis, arteriosclerosis, multiple sclerosis, arthritis, rheumatism, pulmonary fibrosis, osteoporosis, or urolithiasis.

[27] A method for treating a disease associated with the enhancement of the osteopontin production, which comprises administering a therapeutically effective amount of the compound according to any one of the above [1] to [11] or N-(3-(2-amino-3-(4-hydroxyphenoxy)phenyl)-3-oxopropyl)-4-hydroxybenzamide, or a pharmaceutically acceptable salt thereof to a patient in need thereof.

[28] The compound according to any one of the above [1] to [11] or N-(3-(2-amino-3-(4-hydroxyphenoxy)phenyl)-3-oxopropyl)-4-hydroxybenzamide, or a pharmaceutically acceptable salt thereof for use in the treatment of a disease associated with the enhancement of the osteopontin production.

[29] Use of the compound according to any one of the above [1] to [11] or N-(3-(2-amino-3-(4-hydroxyphenoxy)phenyl)-3-oxopropyl)-4-hydroxybenzamide, or a pharmaceutically acceptable salt thereof in manufacturing of a medicament for treating a disease associated with the enhancement of the osteopontin production.

[30] An inhibitor of the osteopontin production, comprising the compound according to any one of the above [1] to [11] or N-(3-(2-amino-3-(4-hydroxyphenoxy)phenyl)-3-oxopropyl)-4-hydroxybenzamide, or a pharmaceutically acceptable salt thereof.

[31] A method for inhibiting the osteopontin production, which comprises administering a therapeutically effective amount of the compound according to any one of the above [1] to [11] or N-(3-(2-amino-3-(4-hydroxyphenoxy)phenyl)-3-oxopropyl)-4-hydroxybenzamide, or a pharmaceutically acceptable salt thereof to a patient in need thereof.

[32] A compound of formula (I):

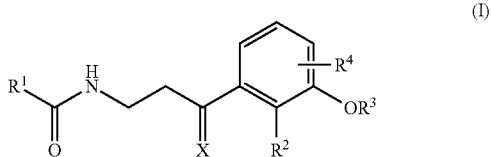

wherein $R^1$ and $R^3$ are independently hydrogen atom, $C_{1-6}$ alkyl, $C_{2-6}$ alkenyl, $C_{2-6}$ alkynyl, $C_{3-8}$ cycloalkyl, $C_{3-8}$ heterocycloalkyl, $C_{6-10}$ aryl, or $C_{6-10}$ heteroaryl wherein the $C_{1-6}$ alkyl, $C_{2-6}$ alkenyl, $C_{2-6}$ alkynyl, $C_{3-8}$ cycloalkyl, $C_{3-8}$ heterocycloalkyl, $C_{6-10}$ aryl, and $C_{6-10}$ heteroaryl independently may be optionally substituted with one group or the same or different two or more groups selected independently from the group consisting of halogen, hydroxy, mercapto, cyano, nitro, amino, mono- or di-$C_{1-6}$ alkylamino, $C_{1-4}$ acyl, $C_{1-4}$ alkylsulfonyl, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and $-OR^5$ at any replaceable positions;

$R^2$ is hydrogen atom, amino, amino substituted with one or two independently-selected $C_{1-6}$ alkyl, hydroxy, or $C_{1-6}$ alkoxy;

$R^4$ is hydrogen atom, halogen, amino, amino substituted with one or two independently-selected $C_{1-6}$ alkyl, $C_{1-6}$ alkyl, or $C_{1-6}$ haloalkyl;

$R^5$ is $C_{2-6}$ alkenyl, $C_{2-6}$ alkynyl, $C_{3-8}$ cycloalkyl, $C_{3-8}$ heterocycloalkyl, $C_{6-10}$ aryl, or $C_{6-10}$ heteroaryl wherein the $C_{2-6}$ alkenyl, $C_{2-6}$ alkynyl, $C_{3-8}$ cycloalkyl, $C_{3-8}$ heterocycloalkyl, $C_{6-10}$ aryl, and $C_{6-10}$ heteroaryl may be optionally substituted with one group or the same or different two or more groups selected independently from the group consisting of halogen, hydroxy, mercapto, cyano, nitro, amino, mono- or di-$C_{1-6}$ alkylamino, $C_{1-4}$ acyl, $C_{1-4}$ alkylsulfoxy, $C_{1-6}$ alkyl, $C_{1-6}$ haloalkyl, $C_{1-6}$ alkoxy, $C_{1-6}$ haloalkoxy, $C_{2-6}$ alkenyl, and $C_{2-6}$ alkynyl at any replaceable positions; and X is O, or when $R^2$ is amino or substituted amino, X may be CH connecting the nitrogen atom in $R^2$ to form a pyrrole ring, or a pharmaceutically acceptable salt thereof, provided that the following compound is excluded:

N-(3-(2-amino-3-(4-hydroxyphenoxy)phenyl)-3-oxopropyl)-4-hydroxybenzamide.

Effects of the Invention

The present compound has an inhibitory effect of the osteopontin production and can be useful as a novel medicament for the treatment and/or prophylaxis of a disease associated with the enhancement of the osteopontin production, for example, cancer.

BRIEF DESCRIPTION OF THE DRAWINGS

FIG. 1 shows the amounts of the OPN production calculated by the ELISA of the control group and Compound 1-treated groups (10 μM and 20 μM) in HepG2 cells.

FIG. 2 shows the amounts or the OPN production calculated by the ELISA of the control group and Compound 1-treated groups (12.5 μM and 23 μM) in A549 cells.

FIG. 3 shows the amounts of the OPN production calculated by the ELISA of the control group and Compound 1-treated groups (25 μM and 50 μM) in OUR-10 cells.

FIG. 4 shows the amounts of the OPN production calculated by the ELISA of the control group and Compound 1-treated groups (20 μM and 40 μM) in QGP-1 cells.

FIG. 5 shows the amounts of the OPN production calculated by the ELISA of the control group and Compound 6-treated groups (10 μM and 20 μM) in A549 cells.

FIG. 6 shows the wound-healing rates of Compound 1-treated groups (12.5 μM and 25 μM) to chat of the control group defined as 100%, in A549 cells.

FIG. 7 shows the percentages of the numbers of invading cells of Compound 1-treated groups (12.5 μM and 25 μM) and Compound 6-treated group (10 μM) to that of the control group defined as 100%, in A549 cells.

FIG. 8 shows the percentages of the amounts of the OPN production calculated by the ELISA of Compound 19-treated groups (12.5 μM and 25 μM) to that of the control group defined as 100%, in A549 cells.

FIG. 9 shows the percentages of the amounts of the OPN production calculated by the ELISA of Compound 26-treated groups (12.5 μM and 25 μM) to that of the control group defined as 100%, in A549 cells.

FIG. 10 shows the percentages of the amounts of the OPN production calculated by the ELISA of Compound 38-treated groups (12.5 μM and 25 μM) to that of the control group defined as 100%, in A549 cells.

DESCRIPTION OF EMBODIMENTS

The present compound may be in the forms of a hydrate and/or a solvate. Thus, the present compound also encompasses the hydrate and/or the solvate. Examples of the solvate include an ethanol solvate.

The present compound may have one or more asymmetric carbon atoms or may have geometrical isomerism or axial chirality, and thus it may include some kinds of enantiomers or stereoisomers thereof. The present compound encompasses the stereoisomers, mixtures thereof, and racemic compounds thereof.

Also, the present compound encompasses compounds wherein one or more of $^1H$ are replaced with $^2H(D)$ (i.e. deuterated form).

The present compound and a pharmaceutically acceptable salt thereof which is obtained in a form of crystal may show polymorphism. Such crystalline polymorphism is also encompassed in the present invention.

Hereinafter, the terms used herein are explained. The term "$C_{1-6}$ alkyl" as used herein means a straight or branched, saturated hydrocarbon group having 1 to 6 carbon atoms, and may be optionally substituted with one or more substituents within the scope of the present invention. The preferred number of carbon atoms in the "$C_{1-6}$ alkyl" may be 1 to 5, 1 to 4, or 1 to 3. Specific examples thereof include methyl, ethyl, propyl, isopropyl, butyl, isobutyl, sec-butyl, tert-butyl, pentyl, isopentyl, neopentyl, and hexyl.

The term "$C_{2-6}$ alkenyl" as used herein means a straight or branched, aliphatic hydrocarbon group having 2 to 6 carbon atoms and one or more carbon-carbon double bonds, and may be optionally substituted with one or more substituents within the scope of the present invention. The preferred number of carbon atoms in the "$C_{2-6}$ alkenyl" may be 2 to 5, 2 to 4, or 2 to 3. Specific examples thereof include ethenyl, propenyl, butenyl, pentenyl, and hexenyl.

The term "$C_{2-6}$ alkynyl" as used herein means a straight or branched, aliphatic hydrocarbon group having 2 to 6 carbon atoms and one or more carbon-carbon triple bonds, and may be optionally substituted with one or more substituents within the scope of the present invention. The preferred number of carbon atoms in the "$C_{2-6}$ alkynyl" may be 2 to 5, 2 to 4, or 2 to 3. Specific examples thereof include ethynyl, propynyl, butynyl, pentynyl, and hexynyl.

The term "$C_{3-8}$ cycloalkyl" as used herein means a mono- or poly-cyclic saturated hydrocarbon group, and may be optionally substituted with one or more substituents within the scope of the present invention. Specific examples thereof include cyclopropyl, cyclobutyl, cyclopentyl, cyclohexyl, cycloheptyl, and cyclooctyl.

The term "$C_{3-8}$ heterocycloalkyl" as used herein means a mono- or bi-cyclic non-aromatic heterocyclyl group having 3 to 8 carbon atoms and 1 to 4 heteroatoms selected independently from the group consisting of nitrogen atom, oxygen atom, and sulfur atom, and may be optionally substituted with one or more substituents within the scope of the present invention. Nitrogen and sulfur atoms may be optionally oxidized, and nitrogen atom may be optionally quaternized. As for the bicyclic group, the fused rings thereof may contain a ring composed of only carbon atoms, and said ring may be saturated, partially-saturated, or unsaturated. The "$C_{3-8}$ heterocycloalkyl" may be 5- to 7-membered monocyclic heterocycloalkyl containing 1 or 2 nitrogen atom(s) and/or oxygen atom(s) in total. Specific examples thereof include azetidinyl, pyrrolidinyl, piperidinyl, piperazinyl, morpholinyl, homopiperidinyl, tetrahydrofuranyl, and tetrahydropyranyl.

The term "$C_{6-10}$ aryl" as used herein means a mono- or bi-cyclic aromatic hydrocarbon group having 6 to 10 carbon atoms in which one or more hydrogen atoms on the aromatic ring may be optionally substituted with one or more substituents within the scope of the present invention. Specific examples thereof include phenyl, 1-naphtyl, 2-naphtyl, and anthracenyl.

The term "heteroaryl" as used herein means a mono- or bi-cyclic aromatic heterocyclyl group having 1 to 4 heteroatoms selected independently from the group consisting of nitrogen atom, oxygen atom, and sulfur atom, and may be optionally substituted with one or more substituents within the scope of the present invention. The preferred "heteroaryl" may be 5- or 6-membered monocyclic aromatic heterocyclyl group containing 1 or 2 nitrogen atoms. Specific examples thereof include pyridyl, pyridazinyl, isothiazolyl, pyrrolyl, furyl, thienyl, thiazolyl, imidazolyl, pyrimidinyl, thiadiazolyl, pyrazolyl, oxazolyl, isoxazolyl, pyrazinyl, triazinyl, triazolyl, imidazolidinyl, oxadiazolyl, triazolyl, tetrazolyl, indolyl, indazolyl, chromenyl, quinolyl, isoquinolyl, benzofuranyl, benzothienyl, benzoxazolyl, benzothiazolyl, benzisoxazolyl, benzisothiazolyl, benzotriazolyl, and benzimidazoly The term "halogen" as used herein means fluorine atom, chlorine atom, bromine atom, or iodine atom. Among them, fluorine atom or chlorine atom is preferred.

The term "mono- or di-$C_{1-6}$ alkylamino" as used herein means an amino group in which one or two hydrogen atoms thereon are replaced with the above-mentioned alkyl group having 1 to 6 carbon atoms. When an amino group is substituted with two alkyl groups, the alkyl groups may be same or different. Specific examples thereof include methylamino, ethylamino, dimethylamino, and diethylamino.

The term "$C_{1-4}$ acyl" as used herein means a carbonyl (—C(=O)) group which is linked to hydrogen atom or the above-mentioned alkyl group having 1 to 3 carbon atoms. Specific examples thereof include formyl, acetyl, and propionyl.

The term "$C_{1-4}$ acylamino" as used herein means an amino group which is linked to the above-mentioned acyl group. Specific examples thereof include acetylamino and propionylamino.

The term "$C_{1-4}$ alkylsulfonyl" as used herein means a sulfonyl (—S(=O)$_2$) group which is linked to the above-mentioned alkyl group having 1 to 4 carbon atoms. Specific examples thereof include methylsulfonyl, ethylsulfonyl, and propylsulfonyl.

The term "$C_{1-6}$ haloalkyl" as used herein means the above-mentioned alkyl group having 1 to 6 carbon atoms in which one or more hydrogen atoms thereon are replaced with halogen atom(s). The number of replaceable hydrogen atoms can range from one up to the total number of hydrogen atoms in the parent alkyl group. When the group has two or more halogen atoms, the halogen atoms may be the same or different. Specific examples thereof include chloromethyl, trifluoromethyl, and 2,2,2-trifluoroethyl.

The term "$C_{1-6}$ alkoxy" as used herein means a group wherein the above-mentioned alkyl group having 1 to 6 carbon atoms is linked through oxygen atom. Specific examples thereof include, but are not limited to, methoxy, ethoxy, propoxy, isopropoxy, butyloxy, pentyloxy, isopentyloxy, neopentyloxy, and hexyloxy.

The term "$C_{1-6}$ haloalkoxy" as used herein means the above-mentioned alkoxy group having 1 to 6 carbon atoms in which one or more hydrogen acorns thereon are replaced with halogen atom(s). The number of replaceable hydrogen atoms can range from one up to the total number of hydrogen atoms in the parent alkyl group. When the group has two or more halogen atoms, the halogen atoms may be the same or different. Specific examples thereof include chloromethoxy, trifluoromethoxy, and 2,2,2-trifluoroethoxy.

The term "osteopontin" or "OPN" as used herein means a secreted acidic phosphorylated glycoprotein identified as a major non-collagenous protein constituting the matrix of bone tissue wherein calcium is precipitated, which has a molecular weight of about 41 kDa. Osteopontin has a RGD sequence which binds to integrin, and makes both osteoclasts and osteoblasts adhere to the periphery of bone system. Also, osteopontin is highly negatively charged, thereby it can precipitate hydroxyapatite therein to retain calcium in bone. In addition, OPN is involved in various functions such as cell migration, control of nitric monoxide production, tumors, and the immune system.

Examples of the term "disease associated with the enhancement of the osteopontin (OPN) production" as used herein include cancer, hepatitis, arteriosclerosis, multiple sclerosis, arthritis, rheumatism, pulmonary fibrosis, osteoporosis, and urolithiasis. The disease in the present invention is preferably cancer.

The term "pharmaceutically acceptable salt thereof" as used herein means a salt formed from the present compound and a pharmaceutically acceptable acid or base. Where the present compound has a basic functional group such as amino group, the present compound can form a salt with any of various acids. Specific examples of the acid addition salts include inorganic acid salts such as hydrochloride, hydrobromate, hydroiodide, sulfate, perchlorate, and phosphate; organic acid salts such as oxalate, malonate, maleate, fumarate, lactate, malate, citrate, tartrate, benzoate, trifluoroacetate, acetate, methanesulfonate, p-toluenesulfonate, and trifluoromethanesulfonate; and amino acid salts such as glutamate and aspartate.

Where the present compound has an acidic functional group, the present compound can form a salt with any of various bases. Specific examples of the base addition salts include alkaline metal salts such as sodium salt and potassium salt; alkaline-earth metal salts such as calcium salt; and ammonium salts.

These salts can be prepared from a mixture of the present compound and an acid or a base by a conventional method such as recrystallization.

The term "treating" or "treatment" as used herein means cure and/or improvement of a disease and/or disorder in a mammal, particularly in a human. For example, the term includes (a) preventing a disease and/or disorder; and also (b) relieving and/or alleviating a disease and/or disorder.

The term "patient" as used herein includes a human and an animal such as a dog, a cat, and a horse. Among them, human is preferred.

The term "therapeutically effective amount" as used herein means an amount for improving, treating, preventing and/or alleviating a disease, disorder and/or side effect, or an amount for slowing progression of a disease and/or disorder, relative to untreated subjects. The term also means an effective amount for promoting a normal physiological function. In the use for therapy, the therapeutically effective amount of the present compound including a salt, a solvate, and a physiologically functional derivative thereof may be administrated as a compound itself. Typically, the effective amount of the present compound or a pharmaceutically acceptable salt thereof is 0.001 to 1000 mg/kg (body weight) per a day, but is not limited thereto.

Examples of the effective amount include an amount of the present compound or a pharmaceutically acceptable salt alone, an amount of a combination of the present compounds, and/or an amount of the present compound in combination with another active ingredient useful for the treatment of cancer.

Preferred aspects of $R^1$ to $R^6$, m, n, p, X, and Y in the present compound of formula (including formula (I) and formula (II)) are illustrated below; but the invention should be limited thereto.

Examples of $R^1$ include $C_{1-6}$ alkyl, $C_{2-6}$ alkynyl, $C_{3-8}$ cycloalkyl, $C_{3-8}$ heterocycloalkyl, $C_{6-10}$ aryl, and 5- to 10-membered heteroaryl which may be optionally substituted with one group or the same or different two or more groups selected independently from the group consisting of halogen, hydroxy, mercapto, cyano, nitro, amino, mono- or di-$C_{1-6}$ alkylamino, $C_{1-4}$ acyl, $C_{1-4}$ acylamino, $C_{1-4}$ alkylsulfonyl, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and —$OR^5$ at any replaceable positions. Among them, $R^1$ is preferably an optionally-substituted, $C_{3-8}$ cycloalkyl, tetrahydropyranyl, pyridyl, thienyl, or phenyl, more preferably phenyl which may be optionally substituted with the group(s) selected independently from halogen, hydroxy, $C_{1-6}$ alkyl, $C_{1-6}$ haloalkyl, or $C_{1-6}$ alkoxy at the 3- and/or 4-position(s), and most preferably phenyl which is substituted the group(s) selected independently from with fluoro, hydroxy, or methoxy at the 3- and/or 4-position(s).

Examples of $R^2$ include hydrogen atom, amino, amino substituted with one or two independently-selected $C_{1-6}$ alkyl, hydroxy, and $C_{1-6}$ alkoxy. Among them, $R^2$ is preferably amino, amino substituted with one or two independently-selected $C_{1-6}$ alkyl, or hydroxy, and more preferably amino. $R^2$ may be linked at any position of the benzene ring. $R^2$ is preferably linked at the 2-position thereof.

Examples of $R^3$ include hydrogen atom, $C_{1-6}$ alkyl, $C_{2-6}$ alkenyl, $C_{2-6}$ alkynyl, $C_{3-8}$ cycloalkyl, $C_{3-8}$ heterocycloalkyl, $C_{6-10}$ aryl, and 5- to 10-membered heteroaryl which may be optionally substituted with one group or the same or different two or more groups selected independently from the group consisting of halogen, hydroxy, mercapto, cyano, nitro, amino, mono- or di-$C_{1-6}$ alkylamino, $C_{1-4}$ acyl, $C_{1-4}$ acylamino, $C_{1-4}$ alkylsulfonyl, $C_{1-6}$ alkyl, $C_{1-6}$ haloalkyl, $C_{1-6}$ alkoxy, $C_{1-6}$ haloalkoxy, $C_{2-6}$ alkenyl, $C_{2-6}$ alkynyl, and —$OR^5$ at any replaceable positions. Among them, $R^3$ is preferably phenyl which may be optionally with the group(s) selected independently from halogen, hydroxy, $C_{1-6}$ alkyl, $C_{1-6}$ haloalkyl, or $C_{1-6}$ alkoxy at 3- and/or 4-position(s), and more preferably phenyl which is substituted with the group(s) selected independently from chloro, hydroxy, methyl, trifluoromethyl, or methoxy at 3- and/or 4-position (s).

Also, when $OR^3$ is linked at the 3-position of the benzene ring, $R^3$ is preferably phenyl which is substituted with one group or the same or different two or more groups selected independently from the group consisting of halogen, hydroxy, $C_{1-6}$ alkyl, $C_{1-6}$ haloalkyl, $C_{1-6}$ alkoxy, and $C_{1-6}$ haloalkoxy at any replaceable positions.

Examples of $R^4$ include hydrogen atom, halogen, amino, mono- or di-$C_{1-6}$ alkylamino, $C_{1-6}$ alkyl, and $C_{1-6}$ haloalkyl. Among them, $R^4$ is preferably hydrogen atom, halogen, or amino, and more preferably hydrogen atom.

Examples of $R^5$ include $C_{2-6}$ alkenyl, $C_{2-6}$ alkynyl, $C_{3-8}$ cycloalkyl, $C_{3-8}$ heterocycloalkyl, $C_{6-10}$ aryl, and 5- to 10-membered heteroaryl which may be optionally substituted with one group or the same or different two or more groups selected independently from the group consisting of halogen, hydroxy, mercapto, cyano, nitro, amino, mono- or di-$C_{1-6}$ alkylamino, $C_{1-4}$ acyl, $C_{1-4}$ acylamino, $C_{1-4}$ alkylsulfoxy, $C_{1-6}$ alkyl, $C_{1-6}$ haloalkyl, $C_{1-6}$ alkoxy, haloalkoxy, $C_{2-6}$ alkenyl, and $C_{2-6}$ alkynyl at any replaceable positions. Among them, $R^5$ is preferably phenyl which may be optionally substituted with halogen, hydroxy, $C_{1-6}$ alkyl, $C_{1-6}$ haloalkyl, or alkoxy, and more preferably phenyl which is substituted with hydroxy.

$R^6$ and $R^7$ are preferably hydrogen atom and $C_{1-4}$ alkyl.

n is preferably 0 to 4. When n is 1 to 4 and $R^6$ is $C_{1-4}$ alkyl, the terminal carbon atom of $R^6$ may be combined with any one carbon atom of the alkylene group in the parenthesis for n to form a 4- to 6-membered ring.

m is preferably 0 or 1.

p is preferably 0 or 1.

X is preferably O. Also, when p is 0 and $R^2$ is amino or substituted amino which is linked at the 2-position of the benzene ring, X may be CH connecting the nitrogen atom in $R^2$ to form a pyrrole ring.

Y is preferably $CH_2$ or NH.

Hereinafter, the processes for preparing the present compounds in Examples are explained.

The present compound of formula (I) can be prepared according to, for example, the following Scheme 1 and the process as described in Non-Patent Reference 4.

Scheme 1

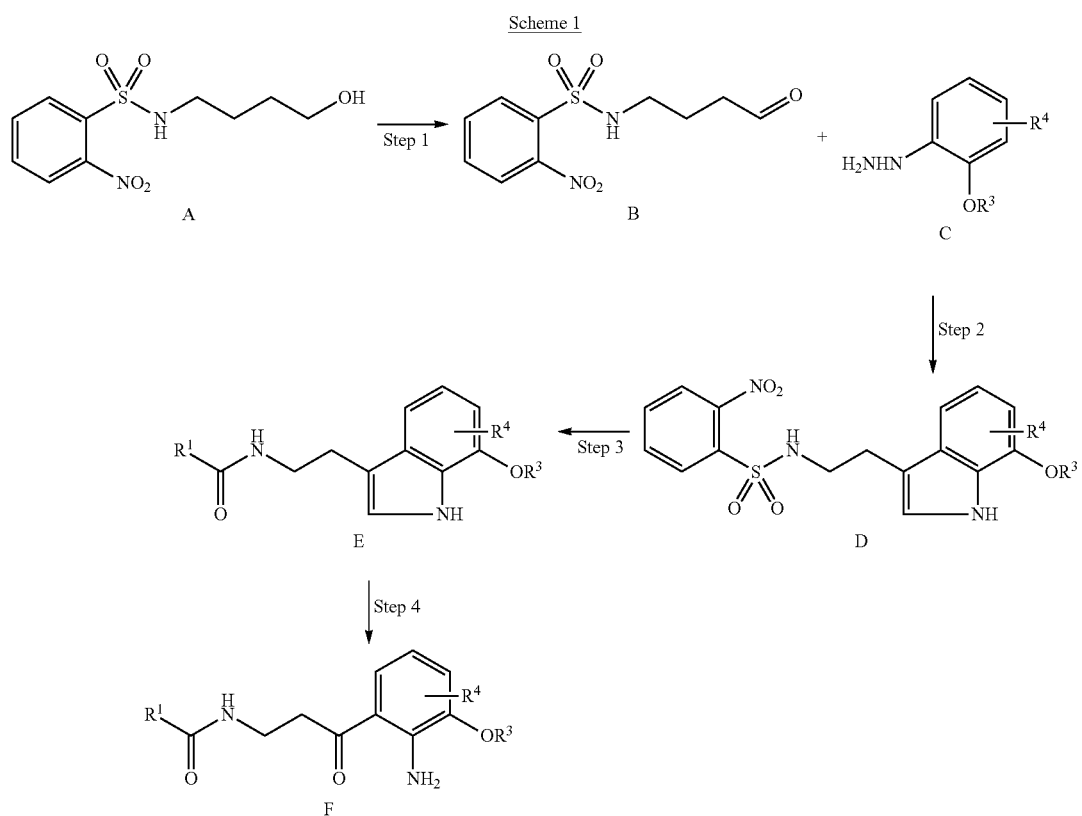

wherein $R^1$, $R^3$, and $R^4$ are as defined in the above [1].

Step 1 is the step for oxidizing the hydroxy group protected with nosyl group (o-nitrobenzenesulfonyl group) of aminoalcohol A with a conventional oxidant such as Jones reagent to produce aldehyde B.

Step 2 is the step for reacting the resulting aldehyde B with aromatic hydrazine C in a protic solvent such as methanol to produce hydrazide, and then heating the hydrazide to 70-80° C. in a weakly acidic solvent such as formic acid and acetic acid to produce indole D.

Step 3 is the step for reacting the resulting indole D with a thiol such as p-mercaptobenzoic acid in a non-protic solvent such as dimethylformamide to cleave o-nitrobenzenesulfonyl group, and then amidating the resulting compound with acyl chloride to produce compound E.

Step 4 is the step for dissolving the resulting compound E in a solvent such as acetonitrile, adding an aqueous sodium metaperiodate solution thereto, heating the mixture to 70-80° C., and undergoing the oxidative cleavage of the indole ring to produce compound F.

Also, when the present compound of formula (I) is substituted with any of various groups, the given group(s) can be introduced in the preparation step of aromatic hydrazine C or indole D in the above Scheme 1, in the amidation with acyl chloride used in step 3, or in the preparation step of compound F, for example, by protecting a reactive group with a commonly-used protecting group, and then cleaving the protected group.

The present compound of formula (II):

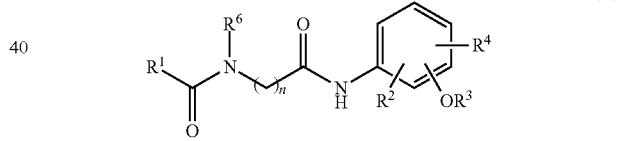

wherein $R^1$ to $R^4$, $R^6$, and n are as defined in the above [1]. can be prepared according to, for example, the following Scheme 2.

Scheme 2

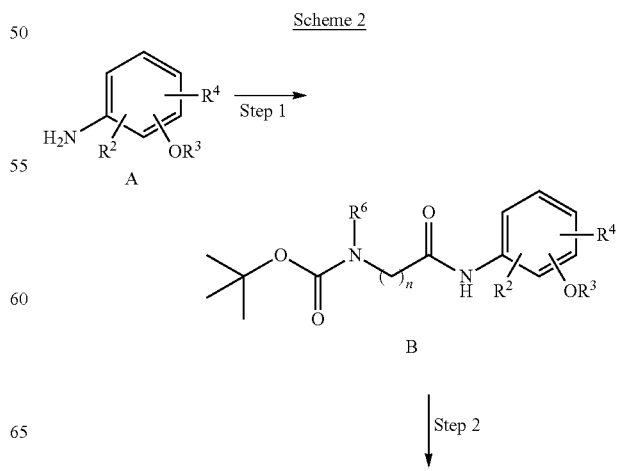

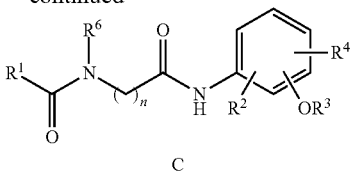

C wherein $R^1$ to $R^4$, $R^6$, and n are as defined in the above [1].

Step 1 is the step for amidating phenoxyaniline derivative A with a carboxylic acid compound having an amino group protected with tert-butyloxycarbonyl group at the terminus thereof in a non-protic solvent such as dichloromethane to produce compound B.

Step 2 is the step for cleaving tert-butyloxycarbonyl group of the resulting compound B, and then amidating the compound with an aromatic carboxylic acid compound to produce compound C.

Also, when the present compound of formula (II) is substituted with any of various groups, the given group(s) can be introduced in Step 1 of the above Scheme 2 or in the preparation step of compound B or compound C, for example, by protecting a reactive group with a commonly-used protecting group, and then cleaving the protected group.

As appropriate, the solvent to be used in each step of the above processes should be selected according to various factors such as the kinds of reaction and starting compound. Examples thereof include alcohols such as methanol, ethanol, and isopropanol; ketones such as acetone and methylketone; halogenated hydrocarbons Such as methylene chloride and chloroform; ethers such as tetrahydrofuran (THF) and dioxane; aromatic hydrocarbons such as toluene and benzene; aliphatic hydrocarbons such as hexane and heptane; esters such as ethyl acetate and propyl acetate; amides such as dimethylformamide (DMF) and N-methyl-2-pyrrolidene; sulfoxides such as dimethylsulfoxide (DMSO); and nitriles such as acetonitrile, and these solvents may be used alone or in combination with two or more solvents. In addition, an organic acid and an organic base may be used as a solvent depending on the types of reaction.

The present compound or an intermediate thereof can be isolated and purified by well-known methods. Examples of the methods include extraction, distribution, reprecipitation, column chromatography (e.g. silica gel column chromatography, ion-exchange column chromatography, or preparative liquid chromatography), and recrystallization. The solvents used for recrystallization may include, for example, alcohol-based solvents such as methanol, ethanol, and 2-propanol; ether-based solvents such as diethyl ether; ester-based solvents such as ethyl acetate; aromatic hydrocarbon-based solvents such as benzene and toluene; ketone-based solvents such as acetone; halogen-based solvents such as dichloromethane and chloroform; hydrocarbon-based solvents such as hexane; non-protic solvents such as dimethylformamide and acetonitrile; water; or a mixed solvent selected from two or more of the above-listed solvents. Other purification methods, for example, those disclosed in Experimental Chemistry Textbook Vol. 1 (the Chemical Society of Japan, ed., Maruzen) can also be used herein.

The present compound or a pharmaceutically acceptable salt thereof can give chirality or contain a substituent with an asymmetric carbon, which can exist as optical isomers. The present compound encompasses a mixture of each of the isomers and an isolated individual isomer, which can be prepared according to a conventional process. Such conventional process includes, for example, using a starting material with an asymmetric center or introducing chirality during the process. For example, an optical isomer can be prepared by using an optically active compound as a starting material or optically resolving a stereo mixture at an appropriate stage during the process. Examples of the optical resolution method include the following diastereomeric salt formation method. When the present compound or an intermediate thereof has a basic functional group, a diastereomeric salt thereof can be formed with an optically active acid (e.g. a monocarboxylic acid such as mandelic acid, N-benzyloxyalanine, and lactic acid; a dicarboxylic acid such as tartaric acid, o-diisopropylidene tartaric acid, and malic acid; and a sulfonic acid such as camphor sulfonic acid and bromocamphor sulfonic acid) in an inert solvent (e.g. an alcohol solvent such as methanol, ethanol, and 2-propanol; an ether solvent such as diethyl ether; an ester solvent such as ethyl acetate; a hydrocarbon solvent such as toluene; an aprotic solvent such as acetonitrile; and a mixture selected from two or more of the above-listed solvents. When the present compound or an intermediate thereof has an acidic functional group, a diastereomeric salt thereof can be formed with an optically active amine (e.g. an organic amine such as 1-phenylethylamine, kinin, quinidine, cinchonidine, cinchonine, and strychnine). The resulting mixture of diastereomeric salts can be resolved to optical isomers.

The present compound has an inhibitory effect osteopontin production, and thus can be useful as a novel medicament for the treatment and/or prophylaxis of a disease associated with the enhancement of osteopontin production, such as cancer, hepatitis, arteriosclerosis, multiple sclerosis, arthritis, rheumatism, pulmonary fibrosis, osteoporosis, and urolithiasis.

Examples of the administration route of the present compound include, but are not limited to, oral, sublingual, buccal, parenteral (e.g. subcutaneous, intramuscular, or intravenous), rectal, topical, or intranasal administration. The daily dosage may vary according to various factors such as the kinds of compounds, administration method, and patient's symptom and age. For example, the present compound for oral administration is typically administered to a human or a mammal at a dose of about 0.001 to 1000 mg/kg, preferably about 0.1 to 500 mg/kg, which may be administered once to several times. The present compound for parenteral administration such as intravenous injection may be administered to a human or a mammal, for example, at a dose of about 0.001 to 300 mg/Kg, preferably about 0.1 to 100 mg/kg.

As appropriate, the dosage form of the present compound may be selected and prepared according to various conditions such as physical status and physical condition of subjects. Examples of the dosage forms include tablets (e.g. orally disintegrating tablets, chewable tablets, effervescent tablets, dispersible tablets, soluble tablets), capsules, granules (e.g. effervescent granules), powders, liquids and solutions for oral administration (e.g. elixirs, suspensions, emulsions, lemonades), syrups (e.g. preparations for syrup), jellies for oral administration, tablets for oral cavity application (e.g. troches/lozenges, sublingual tablets, buccal tablets, mucoadhesive tablets, medicated chewing gums), sprays for oral cavity application, semi-solid preparations for oral cavity application, preparations for gargles, injections (e.g. parenteral infusions, implants/pellets, and sustained release injections), dialysis agents (e.g. peritoneal dialysis agents and hemodialysis agents), inhalations (e.g. dry powder inhalers, inhalation solutions, and inhalation aerosolized agents), suppositories, semi-solid preparations for rectal application, enema agents, ophthalmic preparations, ophthalmic ointment, ear drops, nasal preparations (e.g. nasal dry powder inhalers and nasal solutions), tablets for vaginal use, suppositories for vaginal use, solid dosage forms for cutaneous application (e.g. powders for cutaneous application), liquids and solutions for cutaneous application (e.g. liniments and lotions), sprays for cutaneous application (e.g. aerosols for cutaneous application, and pump sprays for cutaneous application), ointments, creams, gels, patches (e.g. tapes/plasters and cataplasms/gel patches). The present compound is added by 0.1 to 70% by weight to the composition in the preparation.

The medicament for the treatment and/or prophylaxis of the present invention may include any of various types of pharmaceutical active ingredients and pharmaceutically acceptable additives by well-known methods as necessary as long as it does not prevent the effect of the present compound on the treatment and/or prophylaxis of a disease, for example, cancer.

Examples of the various types of pharmaceutical active ingredients to be added in the medicament for the treatment and/or prophylaxis of the present invention include an anti-cancer drug, an anti-inflammatory drug, a herbal drug, and a natural product. Examples of the pharmaceutically acceptable additives include a stabilizing agent, a surfactant, a solubilizer, a buffer, a suspending agent, an antioxidant agent, a coating agent, a moistening agent, a moisture regulator, an algefacient, a coloring agent, a flavor, an isotonicity agent, an emulsifier, a pH adjuster, a skin protectant, a dispersant, a propellant, a fragrance, an antiseptic agent, and a solvent.

EXAMPLES

Hereinafter, the present invention is illustrated in more detail with Examples and Test Examples, but the present invention should not be limited thereto. The identification of the present compound was performed by conventional methods such as nuclear magnetic resonance (NMR) spectroscopy and mass spectrometry.

The following abbreviations may be used herein for the sake of simplicity. The signs used in NMR are follows: s means singlet, d means is doublet, dd is doublet of doublet, ddd means doublet of doublet of doublet, t means triplet, dt means doublet of triplet, td means triplet of doublet, tt means triplet of triplet, q is quartet, it means multiplet, br means broad, brs means broad singlet, brt means broad triplet, and J means coupling constant.

Example 1

N-(3-(2-Amino-3-(4-hydroxyphenoxy)phenyl)-3-oxopropyl)-4-hydroxybenzamide (Brefelamide, Compound 1)

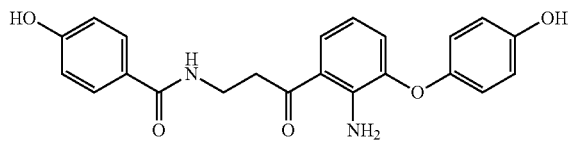 [SMILES: Nc1c(Oc2ccc(O)cc2)cccc1C(=O)CCNC(=O)c1ccc(O)cc1]

Step 1. N-(4-Hydroxybutyl)-2-nitrobenzenesulfonamide (1.80 g, 6.25 mmol) was dissolved in dichloromethane (12.5 ml), and iodobenzene diacetate (3.11 g, 9.66 mmol) and 2,2,6,6-tetramethylbiperidine 1-oxyl (145 mg, 0.94 mmol) were added thereto, and then the mixture was stirred at room temperature for 6 hours. To the reaction mixture were added dioxane (8 mL), water (4 mL), sulfuric acid (0.2 mL), and then (2-(4-(benzyloxy)phenoxy)phenyl)hydrazine (2.01 g, 6.66 mmol), and the mixture was stirred at room temperature for 3 hours. Formic acid (12 ml) was then added thereto, and the mixture was stirred at 40° C. for 9 hours. To the reaction solution was added water (150 mL), and the mixture was extracted with ethyl acetate (100 mL) three times. The combined ethyl acetate layer was washed with water (200 mL), saturated aqueous sodium hydrogen carbonate solution (200 mL), and brine (200 mL), dried over anhydrous sodium sulfate, and the solvent therein was removed in vacuo. The residue was purified by silica gel column chromatography (elution with hexane-ethyl acetate (3:2)) to provide N-(2-(7-(4-(benzyloxy)phenoxy)-1H-indol-3-yl)ethyl)-2-nitrobenzenesulfonamide (1.11 g, 1.99 mmol, 32% (3 steps)).

Step 2. N-(2-(7-(4-(Benzyloxy)phenoxy)-1H-indol-3-yl)ethyl)-2-nitrobenzenesulfonamide (1.11 g, 1.99 mmol) was dissolved in N,N-dimethylformamide (20 mL), and potassium carbonate (1.11 g, 3.98 mmol) and p-mercaptobenzoic acid (614 mg, 7.97 mmol) were added thereto, and then the mixture was stirred at 40° C. for 10 hours. To the reaction solution was added water (60 mL), and the mixture was extracted with ethyl acetate (40 mL) four times. The combined ethyl acetate layer was washed with water (100 mL), saturated aqueous sodium hydrogen carbonate solution (100 mL), and brine (100 mL), dried over anhydrous sodium sulfate, and the solvent therein was removed in vacuo. The residue was dissolved in dichloromethane (10 mL), and triethylamine (1.39 mL, 9.96 mmol) and a solution of 4-(methoxymethoxy)benzoyl chloride (1.00 g, 4.98 mmol) in acetone (10 mL) were added thereto, and then the mixture was stirred at room temperature for 2 hours. To the reaction solution was added 0.3 M hydrochloric acid (50 mL), and the mixture was extracted with ethyl acetate (30 mL) three times. The combined ethyl acetate layer was washed with water (50 mL), saturated aqueous sodium hydrogen carbonate solution (50 mL), and brine (50 mL), dried over anhydrous sodium sulfate, and the solvent therein was removed in vacuo. The residue was purified by silica gel column chromatography (elution with hexane-ethyl acetate (2:3)) to provide N-(2-(7-(4-(benzyloxy)phenoxy)-1H-indol-3-yl)ethyl)-4-(methoxymethoxy)benzamide (431 mg, 0.825 mmol, 41% (2 steps)).

Step 3. N-(2-(7-(4-(Benzyloxy)phenoxy)-1H-indol-3-yl)ethyl)-4-(methoxymethoxy)benzamide (321 mg, 0.614 mmol) was dissolved in ethyl acetate (5 mL) and methanol (5 mL), and 20% palladium hydroxide-carbon (150 mg) was added thereto, and then the mixture was stirred under a hydrogen atmosphere (1 atm) at room temperature for 5 hours. The reaction solution was filtered, and the filtrate was concentrated in vacuo. The residue was dissolved in dichloromethane (8 mL), and triethylamine (260 μL) and acetic anhydride (120 μL) were added thereto, and then the mixture was stirred at room temperature for 4 hours. To the reaction solution was added saturated aqueous ammonium solution (30 mL), and the mixture was extracted with ethyl acetate (20 mL). The combined ethyl acetate layer was washed with water (30 mL), saturated aqueous sodium hydrogen carbonate solution (30 mL), and brine (30 mL), dried over anhydrous sodium sulfate, and the solvent therein was removed in vacuo. The residue was purified by silica gel column chromatography (elution with hexane-ethyl acetate (1:1)) to provide 4-(3-(2-(4-(methoxymethoxy)phenylamido)ethyl)-1H-indol-7-yloxy)phenyl ethanolate (144 mg, 0.303 mmol, 49% (2 steps)).

Step 4. 4-(3-(2-(4-(Methoxymetoxy)phenylamido)ethyl)-1H-indol-7-yloxy)phenyl-ethanolate (144 mg, 0.303 mmol) was dissolved in acetonitrile (4 mL) and water (4 mL), and sodium metaperiodate (259 mg, 1.21 mmol) was added thereto, and then the mixture was stirred at 60° C. for 18 hours. To the reaction solution was added water (20 mL), and the mixture was extracted with ethyl acetate (20 mL) three times. The combined ethyl acetate layer was washed with brine (40 mL), dried over anhydrous sodium sulfate, and the solvent therein was removed in vacuo. The residue was dissolved in methanol (2.5 mL), and hydrochloric acid-methanol reagent (5-10%) (2.5 mL) was added thereto, and then the mixture was stirred at room temperature for 4 hours. To the reaction solution was added saturated aqueous sodium hydrogen carbonate solution (15 mL), and the mixture was extracted with ethyl acetate (20 mL) three times. The combined ethyl acetate layer was washed with brine (30 mL), dried over anhydrous sodium sulfate, and the solvent therein was removed in vacuo. The residue was purified by silica gel column chromatography (elution with chloroform-methanol (49:1)) to provide Compound 1 (50 mg, 0.127 mmol, 42% (2 steps)).

The product was analyzed by electron impact mass spectrometry (EIMS) and NMR. The results of EIMS and NMR are entirely consistent with those of J. Org. Chem. 2005, 70, 8854-8858.

Example 2

4-Hydroxy-N-(2-(7-(4-hydroxyphenoxy)-1H-indol-3-yl)ethyl)benzamide (Compound 2)

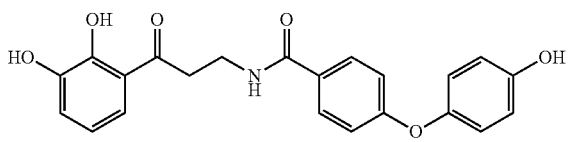

N-(2-(7-(4-(benzyloxy)phenoxy)-1H-indol-3-yl)ethyl)-4-(methoxymethoxy)benzamide (8.2 mg, 0.016 mmol) was dissolved in ethyl acetate (0.5 mL) and methanol (0.5 mL), and 20% palladium hydroxide-carbon (3.0 mg) was added thereto, and then the mixture was stirred under a hydrogen atmosphere 1 atm) at room temperature for 5 hours. The reaction solution was filtered, and the filtrate was concentrated in vacuo. The residue was dissolved in methanol (0.5 mL), and hydrochloric acid-methanol reagent (5-10%) (0.5 mL) was added thereto, and then the mixture was stirred at room temperature for 3 hours. To the reaction solution was added saturated aqueous sodium hydrogen carbonate solution (10 ml), and the mixture was extracted with ethyl acetate (10 mL) three times. The combined ethyl acetate layer was washed with brine (10 mL), dried over anhydrous sodium sulfate, and the solvent therein was removed in vacuo. The residue was purified by silica gel column chromatography (elution with hexane-ethyl acetate (1:2)) to provide Compound 2 (3.2 mg, 0.008 mmol, 53% (2 steps)).

The product was analyzed by electron impact mass spectrometry (EIMS) and NMR. The results of EIMS and NMR are as follows.

$^1$H-NMR (400 MHz, acetone-d$_6$) δ 8.75 (1H, brs), 8.15 (1H, brs), 7.66 (2H, d, J=8.8 Hz), 7.54 (1H, brs), 7.26 (1H, d, J=7.9 Hz), 7.08 (1H, d, J=2.4 Hz), 6.98 (1H, brs), 6.80 (1H, t, J=7.9 Hz), 6.78 (2H, d, J=8.9 Hz), 6.73 (2H, d, J=8.9 Hz), 6.71 (2H, d, J=8.9 Hz), 6.39 (1H, d, J=7.9 Hz), 3.57 (2H, q, J=5.8 Hz), 2.93 (2H, t, J=5.8 Hz). $^{13}$C-NMR (100 MHz, CDCl$_3$) δ 166.9, 160.8, 154.4, 150.4, 145.2, 131.3, 129.8 (2C), 129.0, 127.3, 123.6, 120.9 (2C), 119.9, 116.9 (2C), 115.6 (2C), 114.4, 114.2, 109.2, 41.2, 26.5. EIMS m/z (rel. int) 388 [M]$^+$ (18), 251 (100), 238 (11). HREIMS m/z 388.1411 (388.1423 calculated for C$_{23}$H$_{20}$O$_4$N$_2$).

Example 3

N-(3-(2,3-Dihydroxyphenyl)-3-oxopropyl)-4-(4-hydroxyphenoxy)benzamide (Compound 3)

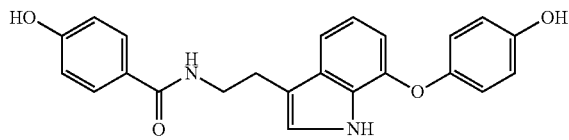 [SMILES: O=C(NCCc1c[nH]c2c(Oc3ccc(O)cc3)cccc12)c1ccc(O)cc1]

Step 1. A mixture of tetrahydrofuran (50 mL) and acetonitrile (3.8 mL, 72.2 mmol) were stirred at −78° C., and then n-butyllithium (1.56 M solution in hexane) (46.0 mL) was added dropwise thereto over 30 minutes. A solution of 2,3-bis(methoxymethoxy)benzaldehyde (3.96 g, 17.52 mmol) which was synthesized according to the process described in J. Org. Chem. 2005, 70, 7505-7511 in tetrahydrofuran (25 mL) was then added dropwise thereto over 30 minutes, and the mixture was stirred for 1 hour with keeping the temperature an −78° C. The mixture was warmed to 0° C., and saturated aqueous ammonium chloride solution (100 mL) was added to the reaction solution, and then the mixture was extracted with diethyl ether (100 mL) three times. The combined diethyl ether layer was washed with water (500 mL) and brine (500 mL), dried over anhydrous sodium sulfate, and the solvent therein was removed in vacuo. The residue was purified by silica gel column chromatography (elution with hexane-ethyl acetate (7:3)) to provide 3-(2,3-bis(methoxymethoxy)phenyl)-3-hydroxypropanenitrile (2.56 g, 9.56 mmol, 55%).

Step 2. Lithium aluminium hydride (429 mg, 11.3 mmol) was suspended in tetrahydrofuran (15 mL), and the suspension was stirred at 0° C. A solution of 3-(2,3-bis (methoxymethoxy)phenyl)-3-hydroxypropanenitrile (1.21 g, 4.52 mmol) in tetrahydrofuran (5 mL) was added thereto, and the mixture was stirred at 70° C. for 4 hours. The mixture was cooled to 0° C., and 1M aqueous sodium hydroxide solution (60 mL) was added thereto. The reaction solution was filtered through Celite®, and the filtrate was extracted with ethyl acetate (50 mL) three times. The combined ethyl acetate layer was washed with brine (100 mL), dried over anhydrous sodium sulfate, and the solvent therein was removed in vacuo. The residue was dissolved in dichloromethane (8.0 mL). Triethylamine (1.0 mL) and then 9-fluorenylmethyl chloroformate (1.675 g, 6.47 mmol) were added thereto at 0° C., and the mixture was stirred for 2 hours. To the reaction solution was added 0.5M hydrochloric acid (30 mL), and then the mixture was extracted with ethyl acetate (20 mL) three times. The combined ethyl acetate layer was washed with saturated aqueous sodium hydrogen carbonate solution (50 mL) and brine (50 mL), dried over anhydrous sodium sulfate, and the solvent therein was removed in vacuo. The residue was purified by silica gel column chromatography (elution with hexane-ethyl acetate (1:1)) to provide (9H-fluoren-9-yl)methyl 3-(2,3-bis (methoxymethoxy)phenyl)-3-hydroxypropylcarbamate (1.017 g, 2.06 mmol, 46% (2 steps)).

Step 3. (9H-Fluoren-9-yl)methyl 3-(2,3-bis (methoxymethoxy)phenyl)-3-hydroxypropylcarbamate (114 mg, 0.231 mmol) was dissolved in N,N-dimethylformamide (1.0 mL). Imidazole (78.4 mg, 1.152 mmol) and then tert-butyldimethysilyl chloride (83.4 mg, 0.553 mmol) were added thereto, and the mixture was stirred at 45° C. for 8 hours. To the reaction solution was then added 0.1M hydrochloric acid (10 mL), and the mixture was extracted with ethyl acetate (10 mL) three times. The combined ethyl acetate layer was washed with water (15 mL), saturated aqueous sodium hydrogen carbonate solution (15 mL), and brine (15 mL), dried over anhydrous sodium sulfate, and the solvent therein was removed in vacuo. The residue was purified by silica gel column chromatography (elution with hexane-ethyl acetate (3:1)) to provide (9H-fluoren-9-yl) methyl 3-(2,3-bis(methoxymethoxy)phenyl)-3-(tert-butyldimethylsilyloxy)propylcarbamate (105 mg, 0.173 mmol, 75%).

Step 4. (9H-Fluoren-9-yl)methyl 3-(2,3-bis (methoxymethoxy)phenyl)-3-(tert-butyldimethylsilyloxy)-propylcarbamate (88.7 mg, 0.146 mmol) was dissolved in N,N-dimethylformamide (1.0 mL), and piperidine (50 µL) was added thereto, and then the mixture was stirred at room temperature for 1 hour. The reaction solution was concentrated in vacuo, and the residue was purified by silica gel column chromatography (elution with chloroform-methanol (8:1)) to provide 3-(2,3-bis(methoxymethoxy)phenyl)-3-(tert-butyldimethylsilyloxy)propane-1-amine (46.6 mg, 0.121 mmol, 83%).

Step 5. 4-(4-(Methoxymethoxy)phenoxy)benzoic acid (31.0 mg, 0.113 mmol) was dissolved in dichloromethane (2.0 mL), and the mixture was stirred at 0° C. 1-Ethyl 3-(3-dimethylaminopropyl)carbodiimide hydrochloride (32.8 mg, 0.171 mmol), 3-(2,3-bis(methoxymethoxy)phenyl)-3-(tert-butyldimethyl-silyloxy)propane-1-amine (43.8 mg, 0.113 mmol) and triethylamine (25 µL) were added thereto, and the mixture was stirred for 2 hours. To the reaction solution was then added 0.2 M hydrochloric acid (10 ml), and the mixture was extracted with ethyl acetate (10 mL) three times. The combined ethyl acetate layer was washed with water (15 mL), saturated aqueous sodium hydrogen carbonate solution (15 mL), and brine (15 mL), dried over anhydrous sodium sulfate, and the solvent therein was removed in vacuo. The residue was purified by silica gel column chromatography (elution with hexane-chloroform (1:4)) to provide N-(3-(2,3-bis(methoxymethoxy)phenyl)-3-(tert-butyldimethylsilyloxy)propyl)-4-(4-(methoxymethoxy)phenoxy)benzamide (38.3 mg, 0.060 mmol, 53%).

Step 6. N-(3-(2,3-bis(methoxymethoxy)phenyl)-3-(tert-butyldimethylsilyloxy)propyl)-4-(4-(methoxymethoxy)phenoxy)benzamide (35.0 mg, 0.055 mmol) was dissolved in tetrahydrofuran (2.0 mL), Tetra-n-butylammonium fluoride (1.0 M solution in tetrahydrofuran) (50 µL) was added thereto at 0° C., and the mixture was stirred for 1 hour. To the reaction solution was then added 0.2 M hydrochloric acid (10 mL), and the mixture was ethyl acetate (10 mL) three times. The combined ethyl acetate layer was washed with water (15 mL), saturated aqueous sodium hydrogen carbonate solution (15 mL), and brine (15 mL), dried over anhydrous sodium sulfate, and the solvent therein was removed in vacuo. The residue was dissolved in N,N-dimethylformamide (2.0 mL), and pyridinium dichromate (103 mg, 0.182 mmol) was added thereto, and the mixture was stirred at room temperature for 15 hours. To the reaction solution was added diethyl ether (15 mL), and the solution was filtered through Celite®, and then the filtrate was washed with water (10 mL), saturated aqueous sodium hydrogen carbonate solution (10 mL), and brine (10 mL), dried over anhydrous sodium sulfate, and the solvent therein was removed in vacuo. The residue was purified by silica gel column chromatography (elution with hexane-ethyl acetate (3:2)) to provide N-(3-(2,3-bis(methoxymethoxy)phenyl)-3-oxopropyl)-4-(4-(methoxymethoxy)phenoxy)benzamide (18.4 mg, 0.035 mmol, 64% (2 steps)).

Step 7. N-(3-(2,3-Bis(methoxymethoxy)phenyl)-3-oxopropyl)-4-(4-(methoxymethoxy)phenoxy)benzamide (13.2 mg, 0.025 mmol) was dissolved in dichloromethane (1.4 mL). Trifluoroacetic acid (0.6 mL) was added thereto at 0° C., and the mixture was stirred for 2 hours. The reaction solution was concentrated in vacuo, and the residue was purified by silica gel column chromatography (elution with hexane-ethyl acetate (1:2)) to provide Compound 3 (9.4 mg, 0.024 mmol, 95%).

The product was analyzed by electron impact mass spectrometry (EIMS) and NMR. The results of EIMS and NMR are as follows.

$^1$H-NMR (600 MHz, CDCl$_3$) δ 7.62 (2H, d, J=8.9 Hz), 7.24 (1H, dd, J=8.2, 1.2 Hz), 7.05 (1H, dd, J=8.2, 1.2 Hz), 7.01 (1H, t, J=6.1 Hz), 6.86 (2H, d, J=8.6 Hz), 6.84 (2H, d, J=8.9 Hz), 6.76 (2H, d, J=8.6 Hz), 6.75 (1H, t, J=8.2 Hz), 3.77 (2H, q, J=6.1 Hz), 3.31 (2H, t, J=6.1 Hz), $^{13}$C-NMR (150 MHz, CDCl$_3$) δ 205.9, 167.3, 161.8, 153.7, 149.6, 147.9, 145.6, 128.7 (2C), 127.5, 121.5 (2C), 121.4 (2C), 121.1, 120.6, 119.2, 116.3 (2C), 116.0, 38.1, 34.6.

EIMS m/z (rel. int) 393 [M]$^+$ (37), 230 (20), 213 (100). HREIMS m/z 393.1211 (393.1212 calculated for C$_{22}$H$_{19}$O$_6$N).

Example 4

N-(3-(2-Amino-3-(4-hydroxyphenoxy)phenyl)-3-oxopropyl)-4-methoxybenzamide (Compound 4)

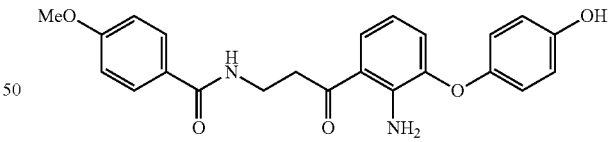

Compound 1 (9.4 mg, 0.024 mmol) was dissolved in N,N-dimethylformamide (1 mL), and potassium carbonate (10.6 mg, 0.077 mmol) and methyl iodide (2.5 µL, 0.040 mmol) were added thereto, and then the mixture was stirred at room temperature for 6 hours. To the reaction solution was then added 0.5 M hydrochloric acid (10 mL), and the mixture was extracted with ethyl acetate (10 mL) three times. The combined ethyl acetate layer was washed with water (15 mL), saturated aqueous sodium hydrogen carbonate solution (15 mL), and brine (15 mL), dried over anhydrous sodium sulfate, and the solvent therein was removed in vacuo. The residue was purified by silica gel column chromatography (elution with chloroform) to provide Compound 4 (4.4 mg, 0.011 mmol, 45%).

The product was analyzed by electron impact mass spectrometry (EIMS) and NMR. The results of EIMS and NMR are as follows.

$^1$H-NMR (600 MHz, CDCl$_3$) δ 7.72 (2H, d, J=8.8 Hz), 7.46 (1H, dd, J=8.3, 1.1 Hz), 6.89 (2H, d, J=8.8 Hz), 6.87 (2H, d, J=8.9 Hz), 6.82 (1H, dd, J=8.3, 1.1 Hz), 6.79 (2H, d, J=8.9 Hz), 6.51 (1H, t, J=8.3 Hz), 3.86 (2H, q, J=5.9 Hz), 3.82 (3H, s), 3.30 (2H, t, J=5.9 Hz).

$^{13}$C-NMR (150 MHz, CDCl$_3$) δ 201.7, 166.9, 162.2, 151.9, 150.1, 145.6, 142.7, 128.7 (2C), 126.9, 125.3, 121.2, 119.9 (2C), 118.4, 116.4 (2C), 114.6, 113.7 (2C), 55.4, 39.0, 35.1.

EIMS m/z (rel. int) 406 [M]$^+$ (100), 254 (88), 135 (79). HREIMS m/z 406.1353 (406.1529 calculated for C$_{23}$H$_{22}$O$_5$N$_2$)

Example 5

N-(3-(2-Amino-3-(4-methoxyphenoxy)phenyl)-3-oxopropyl)-4-methoxybenzamide (Compound 5)

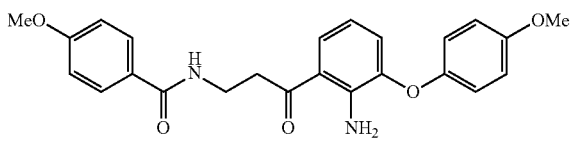 [SMILES: COc1ccc(Oc2cccc(C(=O)CCNC(=O)c3ccc(OC)cc3)c2N)cc1]

Compound 1 (9.4 mg, 0.024 mmol) was dissolved in N,N-dimethylformamide (1 mL), and potassium carbonate (10.6 mg, 0.077 mmol) and methyl iodide (2.5 μL, 0.040 mmol) were added thereto, and then the mixture was stirred at room temperature for 6 hours. To the reaction solution was then added 0.5 M hydrochloric acid (10 mL), and the mixture was extracted with ethyl acetate (10 mL) three times. The combined ethyl acetate layer was washed with water (15 mL), saturated aqueous sodium hydrogen carbonate solution (15 mL), and brine (15 mL), dried over anhydrous sodium sulfate, and the solvent therein was removed in vacuo. The residue was purified by silica gel column chromatography (elution with chloroform-methanol (49:1)) to provide Compound 5 (4.8 mg, 0.011 mmol, 48%).

The product was analyzed by electron impact mass spectrometry (EIMS) and NMR. The results of EIMS and NMR are as follows.

$^1$H-NMR (400 MHz, CDCl$_3$) δ 7.74 (2H, d, J=8.9 Hz), 7.48 (1H, dd, J=8.4, 1.2 Hz), 6.95 (2H, d, J=9.1 Hz), 6.91 (2H, d, J=8.9 Hz), 6.87 (2H, d, J=9.1 Hz), 6.86 (1H, brs), 6.83 (1H, dd, J=8.4, 1.2 Hz), 6.64 (2H, br. s), 6.53 (1H, t, J=8.4 Hz), 3.86 (2H, q, J=5.4 Hz), 3.83 (3H, s), 3.81 (3H, s), 3.32 (2H, t, J=5.4 Hz).

$^{13}$C-NMR (100 MHz, CDCl$_3$) δ 201.7, 166.8, 162.1, 156.0, 145.7, 142.7, 128.7 (2C), 125.3, 121.2, 119.8 (2C), 118.3, 115.0 (2C), 114.6, 113.7 (2C), 55.7, 55.4, 39.0, 35.0.

EIMS m/z (rel. int) 420 [M]$^+$ (61), 269 (100), 135 (48). HREIMS m/z 420.1710 (420.1685 calculated for C$_{24}$H$_{24}$O$_5$N$_2$).

Example 6

N-(3-(2-Amino-3-(4-methoxyphenoxy)phenyl)-3-oxopropyl)-4-hydroxybenzamide (Compound 6)

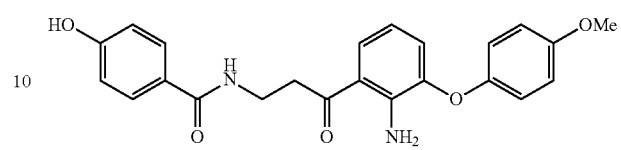

Compound 6 was synthesized according to a similar process to that of Compound 1, except that (2-(4-(methoxyphenoxy)phenyl)hydrazine was used in place of (2-(4-(benzyloxy)phenoxy)phenyl)hydrazine.

The product was analyzed by electron impact mass spectrometry (EIMS) and NMR. The results of EIMS and NMR are as follows.

$^1$H-NMR (400 MHz, CDCl$_3$) δ 7.64 (2H, d, J=8.6 Hz), 7.45 (1H, dd, J=8.3, 1.1 Hz), 6.93 (2H, d, J=8.7 Hz), 6.86 (2H, d, J=8.7 Hz), 6.85 (2H, d, J=8.6 Hz), 6.82 (1H, dd, J=8.3, 1.1 Hz), 6.63 (2H, brs), 6.52 (1H, t, J=8.3 Hz), 3.86 (2H, q, J=5.8 Hz), 3.79 (3H, s), 3.31 (2H, t, J=5.8 Hz).

$^{13}$C-NMR (100 MHz, CDCl$_3$) δ 201.6, 167.5, 159.5, 155.9, 149.9, 145.6, 142.7, 128.9 (2C), 126.0, 125.2, 121.2, 119.7 (2C), 118.2, 115.5 (2C), 114.9 (2C), 114.7, 55.7, 38.9, 35.1.

EIMS m/z (rel. int) 406 [M]$^+$ (3), 268 (100), 121 (29). HREIMS m/z 406.1535 (406.1529 calculated for C$_{23}$H$_{22}$O$_5$N$_2$).

Example 7

N-(3-(2-Amino-3-(4-hydroxyphenoxy)phenyl)-3-oxopropyl)-3-methoxybenzamide (Compound 7)

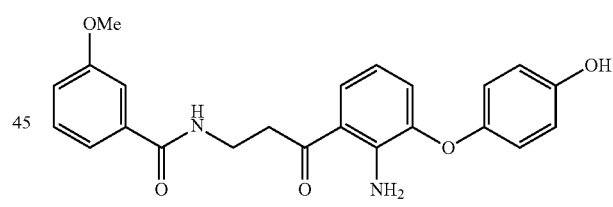

Compound 7 was synthesized according to a similar process to chat of Compound 1, except that 3-methoxybenzoyl chloride was used in place of 4-(methoxymethoxy)benzoyl chloride.

The product was analyzed by electron impact mass spectrometry (EIMS) and NMR. The results of EIMS and NMR are as follows.

$^1$H-NMR (400 MHz, CDCl$_3$) δ 7.46 (1H, dd, J=8.3, 1.0 Hz), 7.23-7.38 (3H, m), 7.00-7.08 (2H, m), 6.88 (2H, d, J=8.8 Hz), 6.83 (2H, d, J=8.8 Hz), 6.79-6.84 (1H, m), 6.64 (2H, brs), 6.52 (1H, t, J=8.3 Hz), 6.30 (1H, brs), 3.87 (2H, q, J=5.5 Hz), 3.83 (3H, s), 3.32 (2H, t, J=5.5 Hz).

$^{13}$C-NMS (100 MHz, CDCl$_3$) δ 201.5, 167.6, 159.8, 152.5, 149.6, 145.8, 142.7, 135.8, 129.6, 125.1, 121.0, 120.0 (2C), 118.7, 118.2, 117.8, 116.5 (2C), 114.6, 112.3, 55.4, 38.8, 35.2.

EIMS m/z (rel. int) 406 [M]$^+$ (95), 255 (100), 151 (54), 135 (44).

HREIMS m/z 406.1550 (406.1529 calculated for $C_{23}H_{22}O_5N_2$).

Example 8

N-(3-(2-Amino-3-(4-hydroxyphenoxy)phenyl)-3-oxopropyl)-acetamide (Compound 8)

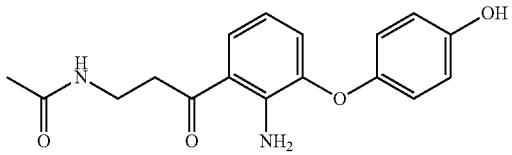 [SMILES: CC(=O)NCCC(=O)c1cccc(Oc2ccc(O)cc2)c1N]

Compound 8 was synthesized according to a similar process to that of Compound 1, except that acetic anhydride was used in place of 4-(methoxymethoxy)benzoyl chloride.

The product was analyzed by electron impact mass spectrometry (EIMS) and NMR. The results of EIMS and NMR are as follows.

$^1$H-NMR (400 MHz, CDCl$_3$) δ 7.44 (1H, dd, J=8.3, 1.2 Hz), 6.89 (2H, d, J=8.9 Hz), 6.83 (1H, dd, J=8.3, 1.2 Hz), 6.82 (2H, d, J=8.9 Hz), 6.63 (2H, brs), 6.53 (1H, t, J=8.3 Hz), 6.22 (1H, brs), 5.47 (1H, brs), 3.68 (2H, q, J=5.4 Hz), 3.22 (2H, t, J=5.4 Hz), 1.97 (3H, s).

$^{13}$C-NMR (100 MHz, CDCl$_2$) δ 201.4, 170.4, 152.3, 149.7, 145.8, 142.6, 125.1, 121.0, 120.0 (2C), 118.2, 116.4 (2C), 114.6, 38.9, 34.6, 23.3.

EIMS m/z (rel. int) 314 (98), 254 (100).

HREIMS m/z 314.1259 (314.1267 calculated for $C_{17}H_{18}O_4N_2$).

Example 9

N-(3-(2-Amino-3-(4-hydroxyphenoxy)phenyl)-3-oxopropyl)-4-fluorobenzamide (Compound 9)

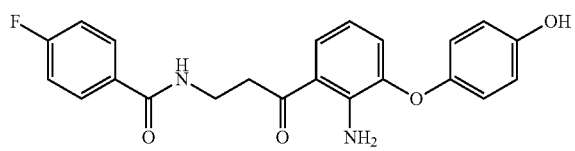 [SMILES: Nc1c(Oc2ccc(O)cc2)cccc1C(=O)CCNC(=O)c1ccc(F)cc1]

Compound 9 was synthesized according to a similar process to that of Compound 1, except that 4-fluorobenzoyl chloride was used in place of 4-(methoxymethoxy)benzoyl chloride.

The product was analyzed by electron impact mass spectrometry (EIMS) and NMR. The results of EIMS and NMR are as follows.

$^1$H-NMR (600 MHz, CD$_3$OD) δ 7.79 (2H, dd, J=8.5, 5.3 Hz), 7.50 (1H, dd, J=8.3, 1.2 Hz), 7.11 (2H, dd, J=9.0, 8.5 Hz), 6.87 (2H, d, J=8.9 Hz), 6.82 (1H, dd, J=8.3, 1.2 Hz), 6.81 (2H, d, J=8.9 Hz), 6.54 (1H, t, J=8.3 Hz), 3.82 (2H, t, J=6.0 Hz), 3.34 (2H, t, J=6.0 Hz).

$^{13}$C-NMR (150 MHz, CD$_3$OD) δ 201.8, 167.4, 166.6 (d, J=229.9 Hz), 164.1, 153.5, 149.1, 146.3, 142.6, 129.5 (2C, d, J=8.6 Hz), 125.1, 120.9, 120.2 (2C), 118.4, 116.4 (2C), 115.7 (2C, d, J=21.5 Hz), 114.9, 38.9, 35.6.

EIMS m/z (rel. int) 394 [M]$^+$ (46), 254 (100), 123 (39).

HREIMS m/z 394.1327 (394.1329 calculated for $C_{22}H_{19}O_4N_2F$).

Example 10

N-(3-(2-Amino-3-(4-hydroxyphenoxy)phenyl)-3-oxopropyl)-cyclohexanecarboxamide (Compound 10)

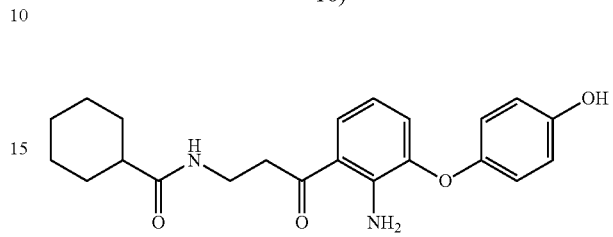

Compound 10 was synthesized according to a similar process to that of Compound 1, except that cyclohexanecarbonyl chloride was used in place of 4-(methoxymethoxy)benzoyl chloride.

The product was analyzed by electron impact mass spectrometry (EIMS) and NMR. The results of FINS and NMR are as follows.

$^1$H-NMR (400 MHz, CDCl$_3$) δ 7.44 (1H, d, J=8.0 Hz), 6.90 (2H, d, J=8.9 Hz), 6.78-6.87 (3H, m), 6.63 (2H, brs), 6.52 (1H, t, J=8.0 Hz), 6.23 (1H, brs), 5.56 (1H, brs), 3.66 (2H, q, J=5.7 Hz), 3.20 (2H, t, J=5.7 Hz), 2.05 (1H, tt, J=12.2, 3.9 Hz), 1.73-1.86 (4H, m), 1.35-1.48 (2H, m), 1.17-1.31 (4H, m).

$^{13}$C-NMR (100 MHz, CDCl$_3$) δ 201.6, 176.2, 152.2, 149.9, 145.7, 142.6, 125.2, 121.1, 120.0 (2C), 118.3, 116.5 (2C), 114.6, 45.5, 39.0, 34.4, 29.6 (2C), 25.7 (3C).

EIMS m/z (rel. int) 382 [M]$^+$ (100), 254 (90).

HREIMS m/z 382.1854 (382.1893 calculated for $C_{22}H_{26}O_4N_2$).

Example 11

N-(3-(2-Amino-3-(4-hydroxyphenoxy)phenyl)-3-oxopropyl)-(tetrahydro-2H-pyran-4-yl)-carboxamide (Compound 11)

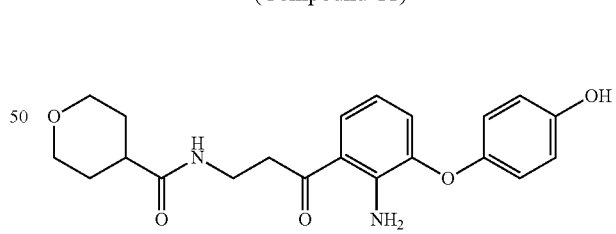

Compound 11 was synthesized according to a similar process to that of Compound 1, except that tetrahydro-2H-pyran-4-carbonyl chloride was used in place of 4-(methoxymethoxy)benzoyl chloride.

The product was analyzed by electron impact mass spectrometry (EIMS) and NMR. The results of EIMS and NMR are as follows.

$^1$H-NMR (400 MHz, CDCl$_3$) δ 8.68 (1H, brs), 7.45 (1H, dd, J=8.3, 1.2 Hz), 6.87 (2H, d, J=8.9 Hz), 6.83 (1H, dd, J=8.3, 1.2 Hz), 6.80 (2H, d, J=8.9 Hz), 6.76 (2H, brs), 6.62 (1H, brs), 6.54 (1H, t, J=8.3 Hz), 3.99 (2H, ddd, J=11.3, 3.8, 2.2 Hz), 3.65 (2H, q, J=5.6 Hz), 3.41 (2H, td, J=11.3, 3.4 Hz), 3.21 (2H, t, J=5.6 Hz), 2.33 (1H, tt, J=10.7, 5.0 Hz), 1.70-1.83 (4H, m).

$^{13}$C-NMR (100 MHz, CDCl$_3$) δ 201.8, 175.1, 153.4, 149.1, 146.2, 142.5, 125.1, 120.9, 120.2 (2C), 118.3, 116.4 (2C), 114.9, 67.4 (2C), 42.2, 38.8, 34.9, 29.2 (2C).

EIMS m/z (rel. int) 384 [M]$^+$ (100), 328 (20), 254 (78). HREIMS m/z 384.1673 (384.1685 calculated for C$_{21}$H$_{24}$O$_5$N$_2$).

Example 12

N-(3-(2-Amino-3-methoxyphenyl)-3-oxopropyl)-4-hydroxybenzamide (Compound 12)

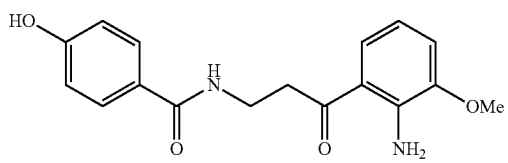 [SMILES: COc1cccc(C(=O)CCNC(=O)c2ccc(O)cc2)c1N]

Compound 12 was synthesized according to a similar process to that of Compound 1, except that (2-methoxyphenyl)hydrazine was used in place of 2-(4-(benzyloxy)phenoxy)phenyl)hydrazine.

The product was analyzed by electron impact mass spectrometry (EIMS) and NMR. The results of EIMS and NMR are as follows.

$^1$H-NMR (400 MHz, CDCl$_3$-CD$_3$OD (4:1)) δ 7.63 (2H, d, J=8.3 Hz), 7.37 (1H, d, J=8.3 Hz), 6.86 (1H, d, J=8.3 Hz), 6.83 (2H, d, J=8.5 Hz), 6.60 (1H, t, J=8.3 Hz), 3.88 (3H, s), 3.80 (2H, q, J=5.7 Hz), 3.29 (2H, t, J=6.6 Hz). $^{13}$C-NMR (100 MHz, CDCl$_3$-CD$_3$OD (4:1)) δ 202.0, 168.2, 160.4, 147.5, 141.6, 129.0 (2C), 125.5, 122.6, 117.2, 115.4, 114.7, 113.3 (2C), 55.9, 39.0, 35.3.

EIMS m/z (rel. int) 314 [M]$^+$ (41) 177 (100), 121 (67), 44 (77).

HREIMS m/z 314.1258 (314.1267 calculated for C$_{17}$H$_{18}$O$_4$N$_2$).

Example 13

N-(3-(2-Amine-3-hydroxyphenyl)-3-oxopropyl)-4-hydroxybenzamide (Compound 13)

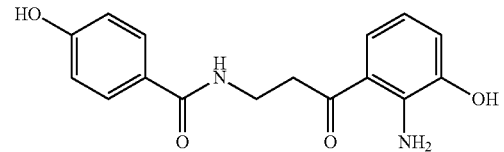 [SMILES: Nc1c(O)cccc1C(=O)CCNC(=O)c1ccc(O)cc1]

Compound 13 was synthesized according to a similar process to that of Compound 1, except that (2-(benzyloxy)phenyl)hydrazine was used in place of 2-(4-(benzyloxy)phenoxy)phenyl)hydrazine.

The product was analyzed by electron impact mass spectrometry (EIMS) and NMR. The results of RIMS and NMR are as follows.

$^1$H-NMR (400 MHz, CD$_3$OD) δ 7.68 (2H, d, J=8.5 Hz), 7.35 (1H, d, J=8.1 Hz), 6.78-6.84 (3H, m), 6.48 (1H, t, J=8.1 Hz), 3.72 (2H, q, J=6.6 Hz), 3.28 (2H, t, J=6.6 Hz).

$^{13}$C-NMR (100 MHz, CD$_3$OD) δ 202.6, 170.2, 162.0, 146.3, 142.4, 130.2 (2C), 126.5, 122.9, 118.9, 118.0, 116.1 (2C), 115.7, 39.8, 37.2.

EIMS m/z (rel. int) 300 [M]$^-$ (87), 163 (37), 121 (100), 44 (91).

HREIMS m/z 300.1128 (300.1110 calculated for C$_{16}$H$_{16}$O$_4$N$_2$)

Example 14

N-(3-(2-Amino-3-(4-methylphenoxy)phenyl)-3-oxopropyl)-4-hydroxybenzamide (Compound 14)

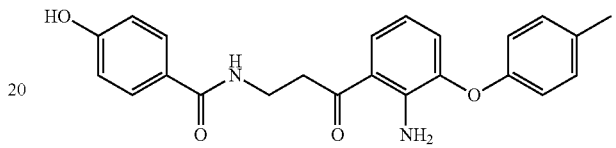

Compound 14 was synthesized according to a similar process to that of Compound 1, except that (2-(4-tolyloxy)phenyl)hydrazine was used in place of 2-(4-(benzyloxy)phenoxy)phenyl)hydrazine.

The product was analyzed by electron impact mass spectrometry (EIMS) and NMR. The results of EIMS and NMR are as follows.

$^1$H-NMR (400 MHz, CD$_3$OD) δ 7.68 (2H, d, J=8.7 Hz), 7.63 (1H, d, J=8.2 Hz), 7.13 (2H, d, J=8.2 Hz), 6.82-6.88 (3H, m), 6.80 (2H, d, J=8.2 Hz), 6.55 (1H, t, J=8.2 Hz), 3.74 (2H, t, J=6.8 Hz), 3.31 (2H, t, J=6.8 Hz), 2.30 (3H, s).

$^{13}$C-NMR (100 MHz, CD$_3$OD) δ 202.4, 170.2, 162.0, 156.2, 146.1, 144.6, 134.0, 131.3 (2C), 130.2 (2C), 127.4, 126.4, 123.5, 119.9, 118.9 (2C), 116.1 (2C), 115.4, 39.9, 37.1, 20.7.

EIMS m/z (rel. int) 390 [M]$^+$ (100), 303 (16), 252 (82), 226 (25), 121 (17).

HREIMS m/z 390.157 (390.1580 calculated for C$_{23}$H$_{22}$O$_4$N$_2$).

Example 15

N-(3-(2-Amino-3-(4-(trifluoromethyl)phenoxy)phenyl)-3-oxopropyl)-4-hydroxybenzamide (Compound 15)

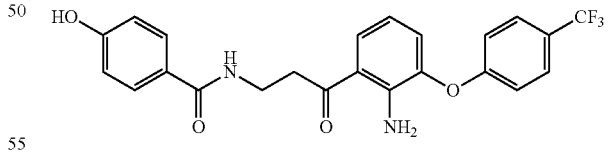

Compound 15 was synthesized according to a similar process to that of Compound 1, except that (2-(4-(trifluoromethyl)phenoxy)phenyl)hydrazine was used in place of 2-(4-(benzyloxy)phenoxy)phenyl)hydrazine.

The product was analyzed by electron impact mass spectrometry (EIMS) and NMR. The results of EIMS and NMR are as follows.

$^1$H-NMR (600 MHz, CD$_3$OD) δ 7.77 (1H, d, J=8.2 Hz), 7.68 (2H, d, J=8.7 Hz), 7.60 (2H, d, J=9.0 Hz), 7.04-7.08 (3H, m), 6.81 (2H, d, J=8.7 Hz), 6.65 (1H, t, J=8.2 Hz), 3.74 (2H, t, J=6.7 Hz), 3.33 (2H, t, J=6.8 Hz).

$^{13}$C-NMR (150 MHz, CD$_3$OD) δ 202.4, 170.2, 162.0, 161.9, 145.1, 143.7, 130.2 (2C), 129.3, 128.2 (2C, q, J=3.6 Hz), 126.7, 126.2, 125.8 (q, J=32.2 Hz), 125.7 (q, J=270.8 Hz), 120.5, 117.9 (2C), 116.1 (2C), 115.6, 39.9, 37.1.

EIMS m/z (rel. int) 444 [M]$^+$ (100), 306 (90), 280 (41), 121 (30).

HREIMS m/z 444.1296 (444.1297 calculated for C$_{23}$H$_{19}$O$_4$N$_2$F$_3$).

Example 16

N-(3-(2-Amino-3-(3,4-dimethoxyphenoxy)phenyl)-3-oxopropyl)-4-hydroxybenzamide (Compound 16)

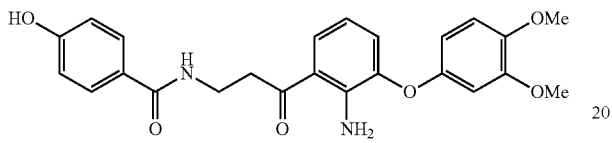

Compound 16 was synthesized according to a similar process to that of Compound 1, except that (2-(3,4-dimethoxyphenoxy)phenyl)hydrazine was used in place of 2-(4-(benzyloxy)phenoxy)phenyl)hydrazine.

The product was analyzed by electron impact mass spectrometry (EIMS) and NMR. The results of EIMS and NMR are as follows.

$^1$H-NMR (400 MHz, CD$_3$OD) δ 7.68 (2H, d, J=8.5 Hz), 7.61 (1H, d, J=8.3 Hz), 6.87 (1H, d, J=8.0 Hz), 6.86 (1H, d, J=8.3 Hz), 6.80 (2H, d, J=8.5 Hz), 6.70 (1H, d, J=2.7 Hz), 6.55 (1H, t, J=8.3 Hz), 6.47 (1H, dd, J=8.0, 2.7 Hz), 3.80 (3H, s), 3.77 (3H, s), 3.74 (2H, t, J=6.6 Hz), 3.31 (2H, t, J=6.6 Hz).

$^{13}$C-NMR (100 MHz, CD$_3$OD) δ 202.4, 170.2, 162.0, 152.4, 151.6, 146.8, 146.6, 144.4, 130.2, 127.1, 126.4, 122.9, 119.8, 116.1 (2C), 115.4, 113.9, 110.5 (2C), 104.9, 57.0, 56.5, 39.9, 37.1.

EIMS m/z (rel. int) 436 [M]$^+$ (100), 299 (85), 284 (47), 272 (19), 121 (52).

HREIMS m/z 436.1656 (436.1634 calculated for C$_{24}$H$_{24}$O$_6$N$_2$).

Example 17

N-(3-(2-Amino-3-(4-chlorophenoxy)phenyl)-3-oxopropyl)-4-hydroxybenzamide (Compound 17)

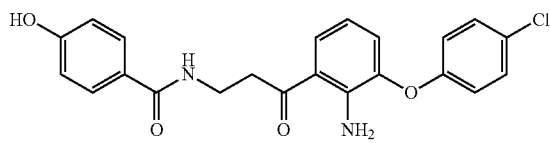 [SMILES: Nc1c(Oc2ccc(Cl)cc2)cccc1C(=O)CCNC(=O)c1ccc(O)cc1]

Compound 17 was synthesized according to a similar process to that of Compound 1, except that (2-(4-chlorophenoxy)phenyl)hydrazine was used in place of 2-(4-(benzyloxy)phenoxy)phenyl)hydrazine.

The product was analyzed by electron impact mass spectrometry (EIMS) and NMR. The results of EIMS and NMR are as follows.

$^1$H-NMR (400 MHz, CD$_3$OD) δ 7.70 (1S, d, J=8.3 Hz), 7.67 (2H, d, J=8.7 Hz), 7.30 (2H, d, J=8.7 Hz), 6.97 (1H, d, J=8.3 Hz), 6.93 (2H, d, J=8.8 Hz), 6.80 (2H, d, J=8.8 Hz), 6.60 (1H, t, J=8.3 Hz), 3.74 (2H, t, J=6.8 Hz), 3.30 (2H, t, J=6.8 Hz).

$^{13}$C-NMR (100 MHz, CD$_3$OD) δ 202.4, 170.2, 162.1, 157.6, 144.9, 131.4, 130.8 (2C), 130.2 (2C), 129.0, 128.4, 126.4, 124.9, 120.2, 119.8 (2C), 116.0 (2C), 115.5, 39.9, 37.1.

EIMS m/z (rel. int) 412 [M+2]$^+$ (38), 410 [M]$^+$ (100), 274 (38), 272 (83), 246 (36), 121 (56).

HREIMS m/z 410.1046 (410.1033 calculated for C$_{22}$H$_{19}$O$_4$ClN$_2$).

Example 18

8-(4-Hydroxyphenoxy)-1,2,3,4-tetrahydro-β-carboline-1-one (Compound 18)

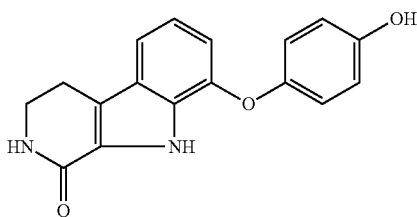 [SMILES: O=C1NCCc2c1[nH]c1c(Oc3ccc(O)cc3)cccc21]

8-(4-Benzyloxyphenoxy)-1,2,3,4-tetrahydro-β-carboline-1-one (299 mg, 0.778 mmol) which was synthesized according to the process as described in J. Org. Chem. 2005, 70, 8854-8858 was dissolved in ethyl acetate (3 mL) and ethanol (3 mL), and 20% palladium hydroxide-carbon (60 mg) was added thereto, and then the mixture was stirred under a hydrogen atmosphere (1 atm) at room temperature for 4 hours. The reaction solution was filtered, and the filtrate was concentrated in vacuo. The residue was purified by silica gel column chromatography (elution with chloroform-methanol (9:1)) to provide Compound 18 (171.7 mg, 0.583 mmol, 75%).

The product was analyzed by electron impact mass spectrometry (EIMS) and NMR. The results of EIMS and NMR are as follows.

$^1$H-NMR (600 MHz, DMSO-d$_6$) δ 11.69 (1H, br.s), 9.23 (1H, br.s), 7.53 (1H, br.s), 7.30 (1H, d, J=8.0 Hz), 6.97 (1H, t, J=8.0 Hz), 6.88 (2H, d, J=8.2 Hz), 6.77 (2H, d, J=8.2 Hz), 6.59 (1H, d, J=8.0 Hz), 3.51 (2H, t, J=6.8 Hz), 2.92 (2H, t, J=6.8 Hz).

$^{13}$C-NMR (150 MHz, DMSO-d$_6$) δ 161.4, 153.4, 148.7, 144.7, 128.8, 127.8, 127.4, 120.0 (2C), 119.9, 118.9, 115.9 (2C), 114.6, 110.8, 41.0, 20.5.

EIMS m/z (rel. int) 294 [M]$^+$ (100), 265 (14), 237 (49).
HREIMS m/z 294.0992 (294.1004 calculated for C$_{17}$H$_{14}$O$_3$N$_2$).

Examples 19 and 20

N-(3-(2-Amino-3-(4-chlorophenoxy)phenyl)-3-oxo-propyl)-4-aminobenzamide (Compound 19) and N-(3-(2-amino-3-(4-chlorophenoxy)phenyl)-3-oxo-propyl)-4-acetylaminobenzamide (Compound 20)

Compound 19:

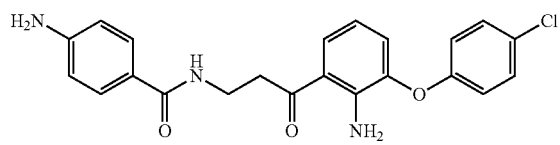 [SMILES: Nc1ccc(C(=O)NCCC(=O)c2cccc(Oc3ccc(Cl)cc3)c2N)cc1]

Compound 20:

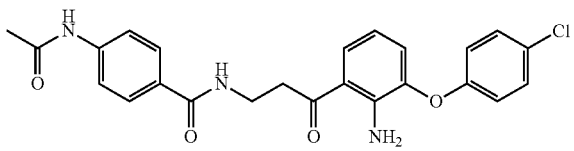 [SMILES: CC(=O)Nc1ccc(C(=O)NCCC(=O)c2cccc(Oc3ccc(Cl)cc3)c2N)cc1]

Step 1. N-(2-(7-(4-Chlorophenoxy)-1H-indol-3-yl)ethyl)-2-nitrobenzenesulfonamide (172 mg, 0.364 mmol) was dissolved in N,N-dimethylformamide (4 mL), and potassium carbonate (100 mg, 0.728 mmol) and p-mercaptobenzoic acid (225 mg, 1.46 mmol) were added thereto, and then the mixture was stirred at 40° C. for 10 hours. To the reaction solution was then added water (15 mL), and the mixture was extracted with ethyl acetate (10 mL) four times. The combined ethyl acetate layer was washed with water (30 mL), saturated aqueous sodium hydrogen carbonate solution (20 mL), and brine (20 mL), dried over anhydrous sodium sulfate, and the solvent therein was removed in vacuo. The residue was dissolved in dichloromethane (4 mL), and triethylamine (0.300 mL, 2.16 mmol) and a solution of 4-acetamidebenzoyl chloride (194 mg, 1.08 mmol) in acetone (5 ml) were added thereto, and then the mixture was stirred at room temperature for 2 hours. To the reaction solution was then added 0.3 M hydrochloric acid (20 mL), and the mixture was extracted with ethyl acetate (20 mL) three times. The combined ethyl acetate layer was washed with water (30 mL), saturated aqueous sodium hydrogen carbonate solution (30 mL), and brine (30 mL), dried over anhydrous sodium sulfate, and the solvent therein was removed in vacuo. The residue was purified by silica gel column chromatography (elution with hexane-ethyl acetate (9:1)) to provide N-(2-(7-(4-chlorophenoxy)-1H-indol-3-yl)ethyl)-4-acetamidobenzamide (29 mg, 0.065 mmol, 18% (2 steps)).

Step 2. N-(2-(7-(4-Chlorophenoxy)-1H-indol-3-yl)ethyl)-4-acetamidobenzamide (29 mg, 0.065 mmol) was dissolved in acetonitrile (1 mL) and water (1 mL), and sodium metaperiodate (60 mg, 0.281 mmol) was added thereof, and then the mixture was stirred at 60° C. for 48 hours. To the reaction solution was then added water (10 mL), and the mixture was extracted with ethyl acetate (10 mL) three times. The combined ethyl acetate layer was washed with brine (10 mL), dried over anhydrous sodium sulfate, and the solvent therein was removed in vacuo. The residue was dissolved in methanol (1 mL), and hydrochloric acid-methanol reagent (5-10%) (1 mL) was added thereto, and then the mixture was stirred at room temperature for 4 hours. To the reaction solution was then added saturated aqueous sodium hydrogen carbonate solution (10 mL), and the mixture was extracted with ethyl acetate (15 mL) three times. The combined ethyl acetate layer was washed with brine (20 mL), dried over anhydrous sodium sulfate, and the solvent therein was removed in vacuo. The residue was purified by silica gel column chromatography (elution with chloroform-methanol (99:1)) to provide Compound 19 (3 mg, 0.007 mmol, 10% (2 steps)). Also, the residue was purified by silica gel column chromatography (elution with chloroform-methanol (49:1)) to provide Compound 20 (2 mg, 0.005 mmol, 7% (2 steps)).

The product was analyzed by electron impact mass spectrometry (EIMS) and NMR. The results of EIMS and NMR are as follows.

Compound 19:
$^1$H-NMR (600 MHz, CD$_3$OD) δ 7.71 (1H, dd, J=8.2, 1.3 Hz), 7.57 (2H, d, J=8.9 Hz), 7.31 (2H, d, J=8.9 Hz), 6.97 (1H, dd, J=8.2, 1.3 Hz), 6.94 (2H, d, J=9.1 Hz), 6.66 (2H, d, J=9.1 Hz), 6.60 (1H, t, J=8.2 Hz), 3.73 (2H, t, J=6.9 Hz), 3.32 (2H, t, J=6.9 Hz).

$^{13}$C-NMR (150 MHz, CD$_3$OD) δ 202.5, 170.5, 157.6, 153.2, 144.9, 144.8, 130.8 (2C), 129.9 (2C), 129.0, 128.5, 124.9, 123.2, 120.2, 119.8 (2C), 115.5, 114.7 (2C), 40.0, 37.0.

EIMS m/z (rel. int) 411 [M+2]$^-$ (4), 409 [M]$^+$ (12), 274 (29), 272 (69), 136 (47), 120 (100).

HREIMS m/z 409.1219 (409.1193 calculated for C$_{22}$H$_{20}$O$_3$N$_3$Cl).

Compound 20:
$^1$H-NMR (600 MHz, CDCl$_3$) δ 7.71 (2H, d, J=8.9 Hz), 7.55 (2H, d, J=8.9 Hz), 7.53 (1H, dd, J=8.2, 1.2 Hz), 7.37 (1H, br.s), 7.25 (2H, d, J=9.1 Hz), 6.92 (1H, dd, J=8.2, 1.2 Hz), 6.88 (2H, d, J=9.1 Hz), 6.87 (1H, t, J=6.3 Hz), 6.56 (1H, t, J=8.2 Hz), 6.53 (2H, br.s), 3.84 (2H, q, J=5.7 Hz), 3.30 (2H, t, J=5.7 Hz), 2.17 (3H, s).

$^{13}$C-NMR (150 MHz, CDCl$_3$) δ 201.6, 168.3, 166.6, 155.5, 143.8, 143.1, 140.8, 129.9, 129.8 (2C), 128.4, 128.0 (2C), 126.6, 123.4, 119.0 (2C), 118.9 (2C), 118.8, 114.8, 38.9, 35.0, 24.7.

EIMS m/z (rel. int) 453 [M+2] (2), 451 [M]$^+$ (5), 274 (40), 272 (100), 136 (34), 120 (49).

HREIMS m/z 451.1278 (451.1299 calculated for C$_{24}$H$_{22}$O$_4$N$_3$Cl).

Example 21

N-(2-(3-(4-Methoxyphenoxy)benzoylamino)ethyl)-4-hydroxybenzamide (Compound 21)

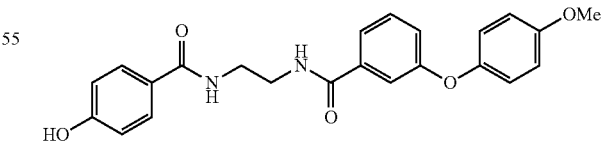

Step 1. N-(Tert-butoxycarbonyl)ethylenediamine (202 mg, 1.26 mol) was dissolved in dichloromethane (3 mL), and 3-(4-methoxyphenoxy)benzoic acid (385 mg, 1.58 mmol), N,N-diisopropylethylamine (660 μL, 3.80 mmol), and (1-cyano-2-ethoxy-2-oxoethylideneaminooxy)dimethylaminomorpholinocarbenium (810 mg, 1.89 mmol) were added thereto, and then the mixture was stirred at room temperature for 18 hours. To the reaction solution was then added 0.3 M hydrochloric acid (20 mL), and the mixture was extracted with ethyl acetate (20 mL) three times. The combined ethyl acetate layer was washed with saturated aqueous sodium hydrogen carbonate solution (40 mL) and brine (40 mL), dried over anhydrous sodium sulfate, and the solvent therein was removed in vacuo. The residue was purified by silica gel column chromatography (elution with hexane-ethyl acetate (2:3)) to provide tert-butyl 2-(3-(4-methoxyphenoxy)phenylamido)ethylcarbamate (467 mg, 1.33 mmol, 96%).

Step 2. Tert-butyl 2-(3-(4-methoxyphenoxy)phenylamido)ethylcarbamate (101 mg, 0.261 mmol) was dissolved in methanol (2.5 mL), and hydrochloric acid-methanol reagent (5-10%) (2.5 mL) was added thereto, and then the mixture was stirred at room temperature for 5 hours. The reaction solution was concentrated in vacuo, the resulting residue was dissolved in dichloromethane (5 mL), and 4-(methoxymethoxy)benzoic acid (63 mg, 0.342 mmol), N,N-diisopropylethylamine (200 µL, 1.15 mmol), and (1-cyano-2-ethoxy-2-oxoethylideneamidooxy)dimethylaminomorpholinocarbenium (173 mg, 0.404 mmol) were added thereto, and then the mixture was stirred at room temperature for 15 hours. To the reaction solution was then added 0.3 M hydrochloric acid (20 mL), and the mixture was extracted with ethyl acetate (20 mL) three times. The combined ethyl acetate layer was washed with saturated aqueous sodium hydrogen carbonate solution (40 ml) and brine (4C mL), dried over anhydrous sodium sulfate, and the solvent therein was remove in vacuo. The residue was purified by silica gel column chromatography (elution with ethyl acetate) to provide N-(2-(4-(methoxymethoxy)phenylamido)ethyl)-3-(4-methoxyphenoxy)benzamide (80 mg, 0.178 mmol, 68% (2 steps)).

Step 3. N-(2-(4-(Methoxymethoxy)phenylamido)ethyl)-3-(4-methoxyphenoxy)benzamide (49 mg, 0.109 mmol) was dissolved in methanol (1.5 mL), and hydrochloric acid-methanol reagent (5-10%) (1.5 ml) was added thereto, and then the mixture was stirred at room temperature for 5 hours. The reaction solution was concentrated in vacuo, and the residue was Purified by silica gel column chromatography (elution with chloroform-methanol (19:1)) to provide Compound 21 (39 mg, 0.096 mmol, 88%).

The product was analyzed by electron impact mass spectrometry (EIMS) and NMR. The results of EIMS and NMR are as follows.

$^1$H-NMR (400 MHz, CDCl$_3$) δ 9.38 (1H, br.s), 8.00 (1H, br.s), 7.69 (1H, br.s), 7.63 (2H, d, J=8.8 Hz), 7.44 (1H, ddd, J=7.9, 2.0, 1.2 Hz), 7.40 (1H, dd, J=2.0, 1.2 Hz), 7.29 (1H, t, J=7.9 Hz), 7.02 (1H, ddd, J=7.9, 2.0, 1.2 Hz), 6.93 (2H, d, J=9.2 Hz), 6.86 (2H, d, J=9.2 Hz), 6.79 (2H, d, J=8.8 Hz), 3.77 (3H, s), 3.53-3.60 (4H, m).

$^{13}$C-NMR (100 MHz, CDCl$_3$) δ 169.0, 168.6, 160.2, 158.7, 156.0, 149.5, 135.5, 129.7, 129.0 (2C), 124.7, 120.8 (2C), 120.7, 120.5, 116.2 (2C), 115.2, 114.9 (2C), 55.5, 40.5, 40.2.

EIMS m/z (rel. int) 406 [M]$^+$ (100), 269 (40), 256 (23), 227 (69), 121 (73).

HREIMS m/z 406.1505 (406.1529 calculated for C$_{23}$H$_{22}$N$_2$O$_5$.

Example 22

N-(2-(2-(4-Methoxyphenoxy)benzoylamino)ethyl)-4-hydroxybenzamide (Compound 22)

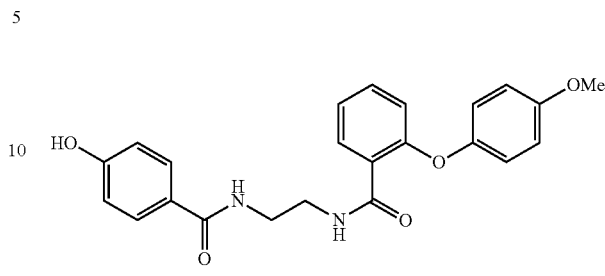

Compound 22 was synthesized according to a similar process to that of Compound 21, except that 2-(4-methoxyphenoxy)benzoic acid was used in place of 3-(4-methoxyphenoxy)benzoic acid.

The product was analyzed by electron impact mass spectrometry (EIMS) and NMR. The results of EIMS and NMR are as follows.

$^1$H-NMR (400 MHz, CD$_3$OD) δ 7.87 (1H, dd, J=7.8, 1.7 Hz), 7.57 (2H, d, J=8.8 Hz), 7.37 (1H, td, J=7.8, 1.7 Hz), 7.13 (1H, td, J=7.8, 1.7 Hz), 6.92 (2H, d, J=9.3 Hz), 6.85 (2H, d, J=9.3 Hz), 6.71-6.80 (3H, m), 3.79 (3H, s), 3.62 (2H, t, J=5.9 Hz), 3.55 (2H, t, J=5.9 Hz).

$^{13}$C-NMR (100 MHz, CD$_3$OD) δ 170.4, 164.3, 162.0, 158.2, 157.8, 150.1, 133.6, 131.8, 130.2 (2C), 126.2, 123.8, 122.2 (2C), 121.9, 118.3, 116.1 (2C), 116.0 (2C), 56.1, 40.7, 40.6.

EIMS m/z (rel. int) 406 [M]$^+$ (25), 215 (100).

HREIMS m/z 406.1549 (406.1529 calculated for C$_{23}$H$_{22}$N$_2$O$_5$).

Example 23

N-(4-Hydroxyphenyl)-4-(3-(4-chlorophenoxy)phenylamino)-4-oxobutanamide (Compound 23)

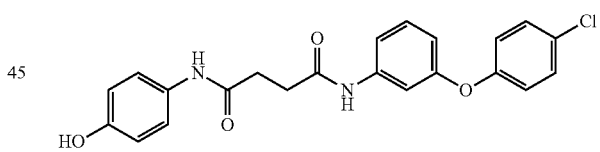

4-(4-Hydroxyphenylamino)-4-oxobutanoic acid (26 mg, 0.122 mmol) was dissolved in methanol (2 mL), and 3-(4-chlorophenoxy)aniline (26 mg, 0.136 mmol) and 4-(4,6-dimethoxyl, 3,5-triazin-2-yl)-4-methylmorpholinium chloride (37 mg, 0.134 mmol) were added thereto, and then the mixture was stirred at room temperature for 1 hour. To the reaction solution was then added 0.3 M hydrochloric acid (10 mL), and the mixture was extracted with ethyl acetate (10 mL) three times. The combined ethyl acetate layer was washed with saturated aqueous sodium hydrogen carbonate solution (20 mL) and brine (20 mL), dried over anhydrous sodium sulfate, and the solvent therein was removed in vacuo. The residue was purified by silica gel column chromatography (elution with chloroform-methanol (19:1)) to provide Compound 23 (11 mg, 0.026 mmol, 21%).

The product was analyzed by electron impact mass spectrometry (EIMS) and NMR. The results of EIMS and NMR are as follows.

$^1$H-NMR (400 MHz, CD$_3$OD) δ 7.36 (1H, t, J=1.5 Hz), 7.32 (2H, d, J=9.0 Hz), 7.29 (2H, d, J=8.9 Hz), 7.24-7.28 (2H, m), 6.97 (2H, d, J=9.0 Hz), 6.73-6.70 (3H, m), 2.65-2.74 (4H, m).
$^{13}$C-NMR (100 MHz, CD$_3$OD) δ 173.1, 172.6, 158.7, 157.4, 155.3, 141.6, 131.7, 131.0, 130.8 (2C), 129.4, 123.4 (2C), 121.4 (2C), 116.2 (2C), 116.1, 115.2, 111.6, 32.8, 32.4.
EIMS m/z (rel. int) 412 [M+2]$^+$ (4), 410 [M]$^+$ (11), 303 (25), 301 (67), 221 (33), 219 (100), 191 (92), 109 (84).
HREIMS m/z 410.1019 (410.1033 calculated for C$_{22}$H$_{19}$N$_2$O$_4$Cl).

Example 24

N-(3-(3-(4-Chlorophenoxy)phenylamino)-3-oxopropyl)-4-hydroxybenzamide (Compound 24)

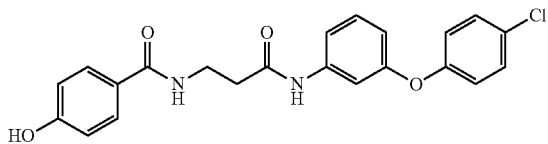 [SMILES: O=C(CCNC(=O)c1ccc(O)cc1)Nc1cccc(Oc2ccc(Cl)cc2)c1]

Step 1. 3-(4-Chlorophenoxy)aniline (55 mg, 0.250 mmol) was dissolved in dichloromethane (3 mL), and N-(tert-butoxycarbonyl)-β-alanine (59 mg, 0.312 mmol), N,N-diisopropylethylamine (130 μL, 0.776 mmol), and (1-cyano-2-ethoxy-2-oxoethylideneaminooxy)dimethylaminopholinocarbenium (145 mg, 0.339 mmol) were added thereto, and then the mixture was stirred at room temperature for 16 hours. To the reaction solution was then added 0.3 M hydrochloric acid (20 ml), and the mixture was extracted with ethyl acetate (20 mL) three times. The combined ethyl acetate layer was washed with saturated aqueous sodium hydrogen carbonate solution (40 mL) and brine (40 mL), dried over anhydrous sodium sulfate, and the solvent therein was removed in vacuo. The residue was purified by silica gel column chromatography (elution with hexane-ethyl acetate (3:7)) to provide tert-butyl 3-(3-(4-chlorophenoxy)phenylamino)-3-oxopropylcarbamate (61 mg, 0.155 mmol, 62%).

Step 2. Tert-butyl 3-(3-(4-chlorophenoxy)phenylamino)-3-oxopropylcarbamate (53 mg, 0.135 mmol) was dissolved in methanol (1.5 mL), and hydrochloric acid-methanol reagent (5-10%) (1.5 mL) was added thereto, and then the mixture was stirred at room temperature for 4 hours. The reaction solution was concentrated in vacuo, and the residue was dissolved in dichloromethane (3 mL), 4-(methoxymethoxy)benzoic acid (32 mg, 0.175 mmol), N,N-diisopropylethylamine (100 μL, 0.574 mmol), and (1-cyano-2-ethoxy-2-oxoethylideneaminooxy)dimethylaminopholinocarbenium (90 mg, 0.210 mmol) were added thereto, and then the mixture was stirred at room temperature for 12 hours. To the reaction solution was then added 0.3 M hydrochloric acid (20 mL), and the mixture was extracted with ethyl acetate (20 mL) three times. The combined ethyl acetate layer was washed with saturated aqueous sodium hydrogen carbonate solution (40 mL) and brine (40 mL), dried over anhydrous sodium sulfate, and the solvent therein was removed in vacuo. The residue was purified by silica gel column chromatography (elution with chloroform-methanol (39:1)) to provide N-(3-(3-(4-chlorophenoxy)phenylamino)-3-oxopropyl)-4-(methoxymethoxy)benzamide (38 mg, 0.082 mmol, 61% (2 steps)).

Step 3. N-(3-(3-(4-Chlorophenoxy)phenylamino)-3-oxopropyl)-4-(methoxymethoxy)benzamide (28 mg, 0.063 mmol) was dissolved in methanol (1 mL), and hydrochloric acid-methanol reagent (5-10%) (1 mL) was added thereto, and then the mixture was stirred at room temperature for 5 hours. The reaction solution was concentrated in vacuo, and the residue was purified by silica gel column chromatography (elution with chloroform-methanol (19:1)) to provide Compound 24 (9 mg, 0.022 mmol, 35%).

The product was analyzed by electron impact mass spectrometry (EIMS) and NMR. The results of EIMS and NMR are as follows.
$^1$H-NMR (400 MHz, CD$_3$OD) δ 7.66 (2H, d, J=8.8 Hz), 7.32-7.36 (1H, m), 7.28 (2H, d, J=9.0 Hz), 7.24-7.27 (2H, m), 6.95 (2H, d, J=9.0 Hz), 6.83 (2H, J=8.8 Hz), 6.70-6.74 (1H, m), 3.67 (2H, t, J=6.5 Hz), 2.65 (2H, t, J=6.5 Hz).
$^{13}$C-NMR (100 MHz, CD$_3$OD) δ 170.8, 168.4, 160.3, 157.2, 155.5, 139.6, 129.8, 129.5 (2C), 128.8 (2C), 128.2, 124.7, 120.0 (2C), 115.1 (2C), 114.8, 114.2, 110.4, 36.5, 36.0.
EIMS m/z (rel. int) 412 [M+2]$^+$ (3), 410 [M]$^+$ (8), 275 (6), 273 (20), 221 (24), 219 (73), 121 (100).
HREIMS m/z 410.1014 (410.1032 calculated for C$_{22}$H$_{19}$N$_2$O$_4$Cl).

Example 25

N-(2-(3-(4-Methoxyphenoxy)phenylamino)-2-oxyethyl)-4-hydroxybenzamide (Compound 25)

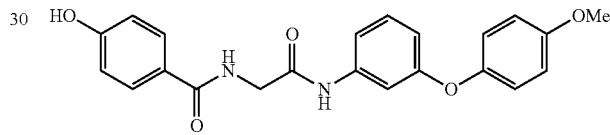

Compound 25 was synthesized according to a similar process to that of Compound 24, except that N-(tert-butoxycarbonyl)-β-alanine was used in place of 3-(4-chlorophenoxy)aniline, and N-(tert-butoxycarbonyl)glycine was used in place of 3-(4-methoxyphenoxy)aniline.

The product was analyzed by electron impact mass spectrometry (EIMS) and NMR. The results of TINS and NMR are as follows.
$^1$H-NMR (400 MHz, acetone-d$_6$) δ 7.74 (2H, d, J=8.9 Hz), 7.18-7.27 (3H, m), 6.98 (2H, d, J=9.2 Hz), 6.89 (2H, d, J=9.2 Hz), 6.86 (2H, d, J=8.9 Hz), 6.65-6.72 (1H, m), 4.14 (2H, s), 3.81 (3H, s).
$^{13}$C-NMR (100 MHz, acetone-d$_6$) δ 167.8, 160.5, 158.8, 155.8, 149.7, 141.7, 138.9, 129.6, 129.0 (2C), 124.1, 120.7 (2C), 115.1 (2C), 114.7 (2C), 113.8, 113.1, 109.2, 55.4, 43.7.
EIMS m/z (rel. int) 392 [M]$^+$ (44), 215 (100), 121 (27).
HREIMS m/z 392.1385 (392.1372 calculated for C$_{22}$H$_{20}$N$_2$O$_5$).

Example 26

N-(3-(3-(4-Methoxyphenoxy)phenylamino)-3-oxopropyl)-4-hydroxybenzamide (Compound 26)

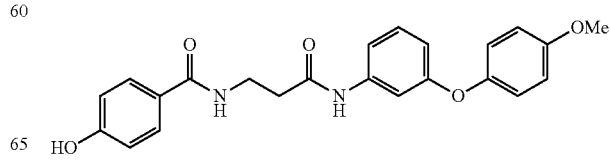

Compound 26 was synthesized according to a similar process to that of Compound 24, except that 3-(4-methoxyphenoxy)aniline was used in place of 3-(4-chlorophenoxy)aniline.

The product was analyzed by electron impact mass spectrometry (EIMS) and NMR. The results of EIMS and NMR are as follows.

$^1$H-NMR (400 MHz, CD$_3$OD) δ 7.67 (2H, d, J=8.8 Hz), 7.24-7.19 (3H, m), 6.98 (2H, d, J=9.3 Hz), 6.89 (2H, d, J=9.3 Hz), 6.84 (2H, d, J=8.8 Hz), 6.63-6.71 (1H, m), 3.80 (3H, s), 3.67 (2H, t, J=6.6 Hz), 2.64 (2H, t, J=6.6 Hz). $^{13}$C-NMR (100 MHz, CD$_3$OD) δ 170.7, 168.5, 160.2, 158.6, 155.7, 149.6, 139.2, 129.4, 128.7 (2C), 124.6, 120.6 (2C), 114.9 (2C), 114.6 (2C), 113.7, 112.9, 109.1, 55.3, 36.3, 35.8.

EIMS m/z (rel. int) 406 [M]$^+$ (55), 269 (23), 215 (100), 121 (28).

HREIMS m/z 406.1504 (406.1529 calculated for C$_{23}$H$_{22}$N$_2$O$_5$).

Example 27

N-(4-(3-(4-Methoxyphenoxy)phenylamino)-4-oxobuthyl)-4-hydroxybenzamide (Compound 27)

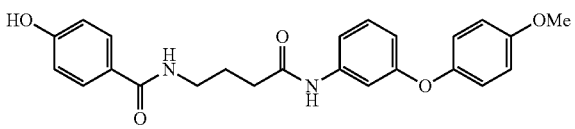 [SMILES: COc1ccc(Oc2cccc(NC(=O)CCCNC(=O)c3ccc(O)cc3)c2)cc1]

Compound 27 was synthesized according to a similar process to that of Compound 24, except that 3-(4-methoxyphenoxy)aniline was used in place of 3-(4-chlorophenoxy)aniline, and N-(tert-butoxycarbonyl)-4-aminobutanoic acid was used in place of N-(tert-butoxycarbonyl)-β-alanine.

The product was analyzed by electron impact mass spectrometry (EIMS) and NMR. The results of EIMS and NMR are as follows.

$^1$H-NMR (400 MHz, CD$_3$OD) δ 7.66 (2H, d, J=8.3 Hz), 7.25-7.17 (3H, m), 6.97 (2H, d, J=8.4 Hz), 6.88 (2H, d, J=8.4 Hz), 6.81 (2H, d, J=8.3 Hz), 6.61-6.66 (1H, m), 3.80 (3H, s), 3.44 (2H, t, J=6.7 Hz), 2.40 (2H, t, J=6.7 Hz), 1.95 (2H, quint, J=6.7 Hz).

$^{13}$C-NMR (100 MHz, CD$_3$OD) δ 183.4, 172.4, 168.7, 160.1, 158.7, 155.8, 149.8, 139.5, 129.5, 128.8 (2C), 120.7 (2C), 115.0 (2C), 114.7 (2C), 113.8, 112.9, 109.2, 55.5, 39.2, 34.5, 25.4.

EIMS m/z (rel. int) 420 [M]$^+$ (100), 270 (16), 257 (36), 215 (96), 121 (84).

HREIMS m/z 420.1693 (420.1684 calculated for C$_{24}$H$_{24}$N$_2$O$_5$).

Example 28

N-(2-(2-(4-Methoxyphenoxy)phenylamino)-2-oxoethyl)-4-hydroxybenzamide (Compound 28)

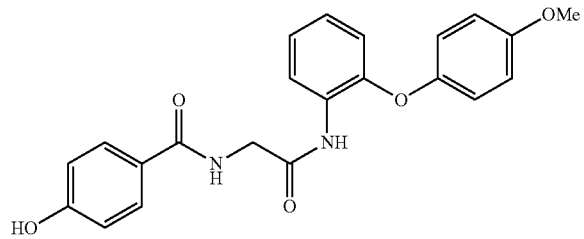 [SMILES: COc1ccc(Oc2ccccc2NC(=O)CNC(=O)c2ccc(O)cc2)cc1]

Compound 28 was synthesized according to a similar process to that of Compound 24, except that 2-(4-methoxyphenoxy)aniline was used place of 3-(4-chlorophenoxy)aniline, and N-(tert-butoxycarbonyl)glycine was used in place of N-(tert-butoxycarbonyl)-β-alanine.

The product was analyzed by electron impact mass spectrometry (EIMS) and NMR. The results of EIMS and NMR are as follows.

$^1$H-NMR (600 MHz, CD$_3$OD) δ 7.67 (2H, d, J=8.9 Hz), 7.00-7.11 (2H, m), 6.90 (2H, d, J=9.1 Hz), 6.83 (2H, d, J=9.0 Hz), 6.80 (2H, d, J=8.9 Hz), 6.77-6.86 (2H, m), 4.19 (2H, s), 3.77 (3H, s).

$^{13}$C-NMR (150 MHz, CD$_3$OD) δ 166.9, 160.8, 154.4, 150.4, 145.2, 131.3, 129.8 (2C), 129.0, 127.5, 123.6, 120.9 (2C), 119.9, 116.9 (2C), 115.6 (2C), 114.4, 114.2, 109.2, 41.2, 26.5. EIMS m/z (rel. int) 392. [M]$^+$ (24), 215 (100).

HREIMS m/z 392.1385 (392.1372 calculated for C$_{22}$H$_{20}$N$_2$O$_5$).

Example 29

N-(3-(2-(4-methoxyphenoxy)phenylamino)-3-oxopropyl)-4-hydroxybenzamide (Compound 29)

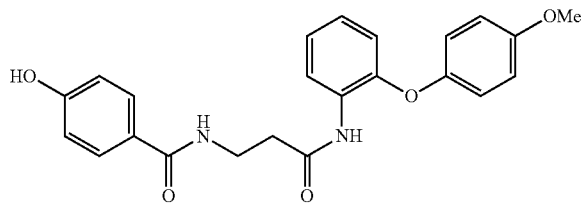 [SMILES: COc1ccc(Oc2ccccc2NC(=O)CCNC(=O)c2ccc(O)cc2)cc1]

Compound 29 was synthesized according to a similar process to that of Compound 24, except that 2-(4-methoxyphenoxy)aniline was used in place of 3-(4-chlorophenoxy)aniline.

The product was analyzed by electron impact mass spectrometry (EIMS) and NMR. The results of EIMS and NMR are as follows.

$^1$H-NMR (600 MHz, CD$_3$OD) δ 8.15 (1H, dd, J=7.8, 1.3 Hz), 7.66 (2H, d, J=8.7 Hz), 7.04 (1H, td, J=7.8, 1.3 Hz), 7.01 (1H, td, J=7.8, 1.3 Hz), 6.93 (2H, d, J=9.0 Hz), 6.88 (2H, d, J=9.0 Hz), 6.82 (2H, d, J=8.7 Hz), 6.73 (1H, dd, J=7.8, 1.3 Hz), 3.80 (3H, s), 3.71 (2H, t, J=6.2 Hz), 2.73 (2H, t, J=6.2 Hz).

$^{13}$C-NMR (150 MHz, CD$_3$OD) δ 170.8, 168.2, 160.1, 155.9, 149.1, 148.1, 128.7 (2C), 127.8, 124.7, 124.6, 122.5, 122.0, 120.4 (2C), 116.1, 114.9 (2C), 114.7 (2C), 55.3, 36.3, 35.8.

EIMS m/z (rel. int) 406 [M]$^+$ (25), 215 (100).

HREIMS m/z 406.1535 (406.1529 calculated for C$_{23}$H$_{22}$N$_2$O$_5$).

Example 30

N-(3-(4-(4-methoxyphenoxy)phenylamino)-3-oxo-propyl)-4-hydroxybenzamide (Compound 30)

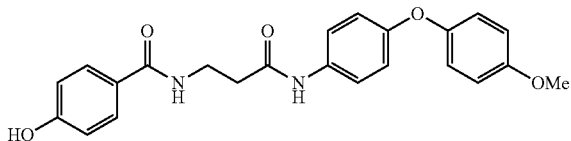 [SMILES: COc1ccc(Oc2ccc(NC(=O)CCNC(=O)c3ccc(O)cc3)cc2)cc1]

Compound 30 was synthesized according to a similar process to that of Compound 24, except that 4-(4-methoxyphenoxy)aniline was used in place of 3-(4-chlorophenoxy) aniline.

The product was analyzed by electron impact mass spectrometry (EIMS) and NMR. The results of EIMS and NMR are as follows.

$^1$H-NMR (400 MHz, CD$_3$OD) δ 7.68 (2H, d, J=8.8 Hz), 7.47 (2H, d, J=9.3 Hz), 6.94 (2H, d, J=9.0 Hz), 6.90 (2H, d, J=9.0 Hz), 6.87 (2H, d, J=9.3 Hz), 6.84 (2H, d, J=8.8 Hz), 3.80 (3H, s), 3.69 (2H, t, J=6.5 Hz), 2.66 (2H, t, J=6.5 Hz).

$^{13}$C-NMR (100 MHz, CD$_3$OD) δ 170.5, 168.4, 160.2, 155.5, 154.5, 150.3, 132.7, 128.8 (2C), 124.6, 121.5 (20), 120.1 (2C), 117.9 (2C), 115.0 (2C), 114.6 (2C), 55.4, 36.2, 36.0.

EIMS m/z (rel. int) 406 [M]$^+$ (48), 215 (100), 121(24).

HREIMS m/z 406.1542 (406.1527 calculated for C$_{23}$H$_{22}$N$_2$O$_5$).

Example 31

N-(3-(4-chlorophenoxy)phenyl)-1-(4-hydroxyphenylcarbonyl)azetidine-3-carboxamide (Compound 31)

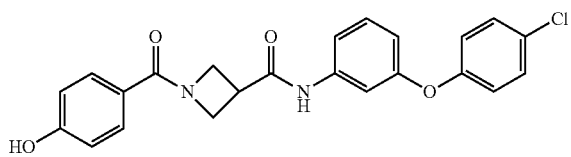 [SMILES: O=C(Nc1cccc(Oc2ccc(Cl)cc2)c1)C1CN(C(=O)c2ccc(O)cc2)C1]

Compound 31 was synthesized according to a similar process to that of Compound 24, except that 1-(tert-butoxycarbonyl)azetidine-3-carboxylic acid was used in place of N-(tert-butoxycarbonyl)-β-alanine.

The product was analyzed by electron impact mass spectrometry (EIMS) and NMR. The results of EIMS and NMR are as follows.

$^1$H-NMR (600 MHz, CD$_3$OD) δ 7.50 (2H, d, J=8.8 Hz), 7.30-7.34 (1H, m), 7.29 (2H, d, J=8.9 Hz), 7.21-7.27 (2H, m), 6.93 (2H, d, J=8.9 Hz), 6.78 (2H, d, J=8.8 Hz), 6.69 (1H, dt, J=6.6, 2.7 Hz), 4.44-4.50 (2H, m), 4.25-4.31 (1H, m), 4.18-4.23 (1H, m), 3.55 (1H, tt, J=8.6, 6.1 Hz).

$^{13}$C-NMR (150 MHz, CD$_3$OD) δ 172.5, 172.3, 162.0, 158.8, 157.2, 141.3, 131.2, 131.1 (2C), 130.9 (2C), 129.5, 124.5, 121.4 (2C), 116.2 (2C), 116.1, 115.5, 111.6, 56.9, 52.7, 35.5. EIMS m/z (rel. int) 424 [M+2]$^+$ (1), 422 [M]$^+$ (3), 287 (1), 285 (4), 274 (20), 272 (41), 121 (100).

HREIMS m/z 422.1004 (422.1033 calculated for C$_{23}$H$_{19}$O$_4$N$_2$Cl).

Example 32

N-(3-(4-chlorophenoxy)phenyl)-1-(4-hydroxyphenylcarbonyl)pyrrolidine-3-carboxamide (Compound 32)

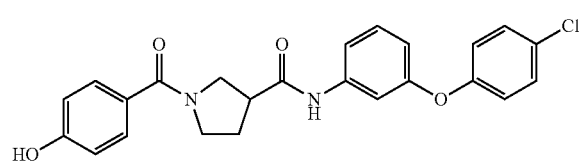 [SMILES: O=C(Nc1cccc(Oc2ccc(Cl)cc2)c1)C1CCN(C(=O)c2ccc(O)cc2)C1]

Compound 32 was synthesized according to a similar process to that of Compound 24, except that 1-(tert-butoxycarbonyl)pyrrolidine-3-carboxylic acid was used in place of N-(tert-butoxycarbonyl)-β-alanine The product was analyzed by electron impact mass spectrometry (EIMS) and NMR. The result of NMR shows that the title compound is a mixture of two conformational isomers (1:1). The results of EIMS and NMR are as follows.

$^1$H-NMR (600 MHz, CD$_3$OD) δ 7.38 (2H, d, J=8.2 Hz), 7.31-7.35 (1H, m), 7.19-7.29 (4H, m), 6.89-6.94 (2H, m), 6.77 (2H, d, J=8.8 Hz), 6.65-6.71 (1H, m), 3.62-3.83 (3H, m), 3.52-3.61 (1H, m), 3.16-3.22 (0.5H, m), 3.04-3.11 (0.5H, m), 2.20-2.27 (0.5H, m), 2.04-2.20 (1.5H, m).

$^{13}$C-NMR (150 MHz, CD$_3$OD): δ 173.6 (0.5C), 172.8 (0.5C), 172.1 (0.5C), 171.9 (0.5C), 160.9, 158.8, 157.3, 141.5 (0.5C), 141.4 (0.5C), 131.1, 130.9 (2C), 130.4 (2C), 129.5, 128.2, 121.4 (2C), 116.1, 116.0 (2C), 115.4, 111.6 (0.5C), 111.5 (0.5C), 53.2 (0.50), 50.5 (0.50), 50.3 (0.50), 47.2 (0.5C), 46.6 (0.5C), 44.8 (0.5C), 31.4 (0.5C), 29.5 (0.5C).

EIMS m/z (rel. int) 438 [M+2]$^+$ (6), 436 [M]$^+$ (17), 317 (4), 315 (12), 221 (3), 219 (9), 190 (100), 121 (85).

HREIMS m/z 436.1177 (436.1190 calculated for C$_{24}$H$_{21}$O$_4$N$_2$Cl).

Example 33

N-(3-(4-Chlorophenoxy)phenyl)-1-(4-hydroxyphenylcarbonyl)piperidine-3-carboxamide (Compound 33)

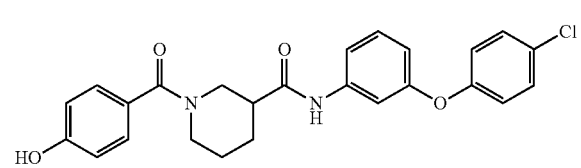 [SMILES: O=C(Nc1cccc(Oc2ccc(Cl)cc2)c1)C1CCCN(C(=O)c2ccc(O)cc2)C1]

Compound 33 was synthesized according to a similar process to that of Compound 24, except that 1-(tert-butoxycarbonyl)piperidine-3-carboxylic acid was used in place of N-(tert-butoxycarbonyl)-β-alanine.

The product was analyzed by electron impact mass spectrometry (EIMS) and NMR. The results of EIMS and NMR are as follows.

$^1$H-NMR (600 MHz, CD$_3$OD) δ 7.29 (2H, d, J=8.5 Hz), 7.18-7.27 (5H, m), 6.93 (2H, d, J=8.8 Hz), 6.75-6.81 (2H, m), 6.66-6.70 (1H, m), 3.72-3.82 (1H, m), 3.25-3.36 (1H, m), 3.05-3.20 (2H, m), 2.49-2.61 (1H, m), 1.96-2.05 (1H, m), 1.66-1.85 (2H, m), 1.47-1.58 (1H, m).

$^{13}$C-NMR (150 MHz, CD$_3$OD) δ 174.1, 173.2, 160.7, 158.7, 157.3, 141.4, 131.1, 130.8 (2C), 130.2 (2C), 129.5, 127.3, 121.4 (2C), 116.2 (2C), 116.1, 115.4, 111.5, 46.3, 45.0, 44.0, 29.0, 26.2.

EIMS m/z (rel. int) 452 [M+2]$^+$ (13), 450 [M]$^+$ (35), 331 (9), 329 (24), 204 (100), 121 (85).

HREIMS m/z 450.1344 (450.1346 calculated for C$_{25}$H$_{23}$O$_4$N$_2$Cl).

Example 34

N-(3-(4-Chlorophenoxy)phenyl)-1-(4-hydroxyphenylcarbonyl)pyrrolidine-2-carboxamide (Compound 34)

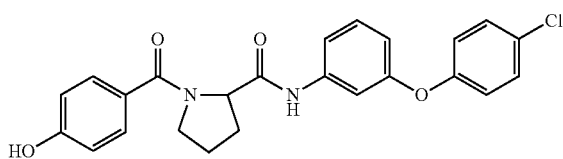 [SMILES: O=C(Nc1cccc(Oc2ccc(Cl)cc2)c1)C1CCCN1C(=O)c1ccc(O)cc1]

Compound 34 was synthesized according to a similar process to that of Compound 24, except that N-(tert-butoxycarbonyl)-DL-proline was used in place of N-(tert-butoxycarbonyl)-β-alanine.

The product was analyzed by electron impact mass spectrometry (EIMS) and NMR. The results of EIMS and NMR are as follows.

$^1$H-NMR (600 MHz, CD$_3$OD) δ 7.45 (2H, d, J=8.7 Hz), 7.35-7.38 (1H, m), 7.28 (2H, d, J=8.9 Hz), 7.23-7.27 (2H, m), 6.93 (2H, d, J=8.9 Hz), 6.77 (2H, d, J=8.8 Hz), 6.68-6.71 (1H, m), 4.57 (1H, t, J=7.3 Hz), 3.66-3.74 (1H, m), 3.55-3.62 (1H, m), 2.26-2.33 (1H, m), 1.92-2.07 (2H, m), 1.79-1.87 (1H, m).

$^{13}$C-NMR (150 MHz, CD$_3$OD) δ 173.2, 172.1, 161.1, 158.8, 157.3, 141.4, 131.1, 130.8 (2C), 130.7 (2C), 129.5, 127.8, 121.5 (2C), 116.1, 115.9 (2C), 115.4, 111.6, 62.9, 52.0, 31.1, 26.6.

EIMS m/z (rel. int) 438 [M+2]$^+$ (1), 436 [M]$^+$ (3), 218 (14), 190 (40), 121 (100).

HREIMS m/z 436.1153 (436.1190 calculated for C$_{24}$H$_{21}$O$_4$N$_2$Cl).

Example 33

N-(3-(3-(4-Chlorophenoxy)phenylamino)-3-oxopropyl)thiophene-2-carboxamide (Compound 35)

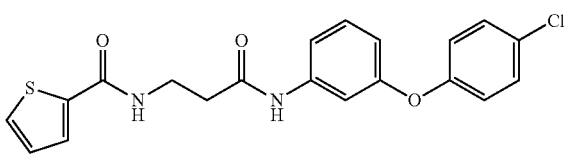 [SMILES: O=C(CCNC(=O)c1cccs1)Nc1cccc(Oc2ccc(Cl)cc2)c1]

Compound 35 was synthesized according to a similar process to that of Compound 24, except that 2-thiophenecarboxylic acid was used in place of 4-(methoxymethoxy)benzoic acid.

The product was analyzed by electron impact mass spectrometry (EIMS) and NMR. The results of EIMS and NMR are as follows.

$^1$H-NMR (600 MHz, CDCl$_3$) δ 9.44 (1H, br.s), 7.74 (1H, br.t, J=6.3 Hz), 7.48 (1H, dd, J=3.8, 1.0 Hz), 7.41 (1H, dd, J=4.9, 1.0 Hz), 7.25-7.27 (1H, m), 7.21 (2H, d, J=9.0 Hz), 7.15-7.19 (2H, m), 6.99 (1H, dd, J=4.9, 3.8 Hz), 6.87 (2H, d, J=9.0 Hz), 6.62-6.66 (1H, m), 3.59 (2H, q, J=6.3 Hz), 2.58 (2H, t, J=6.3 Hz).

$^{13}$C-NMR (150 MHz, CDCl$_3$) δ 170.6, 163.1, 157.2, 155.5, 139.5, 138.4, 130.3, 129.9, 129.6 (2C), 128.4, 128.2, 127.7, 120.1 (2C), 114.8, 114.3, 110.4, 36.5, 36.1.

EIMS m/z (rel. int) 402 [M+2] (17), 400 [M]$^+$ (41), 221 (37), 219 (100), 182 (27), 140 (20), 111 (46).

HREIMS m/z 400.0652 (400.0648 calculated for C$_{20}$H$_{17}$O$_3$N$_2$ClS).

Example 36

N-(3-(3-(4-Chlorophenoxy)phenylamino)-3-oxopropyl)thiophene-3-carboxamide (Compound 36)

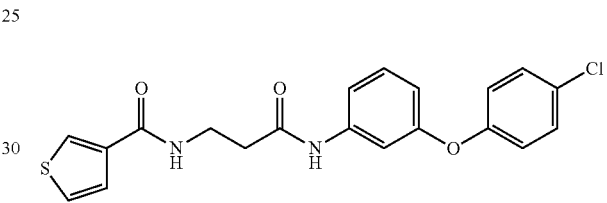

Compound 36 was synthesized according to a similar process to that of Compound 24, except that 3-thiophenecarboxylic acid was used in place of 4-(methoxymethoxy)benzoic acid.

The product was analyzed by electron impact mass spectrometry (EIMS) and NMR. The results of EIMS and NMR are as follows.

$^1$H-NMR (600 MHz, CDCl$_3$) δ 9.38 (1H, br.s), 7.85 (1H, dd, J=3.0, 1.2 Hz), 7.65 (1H, br.t, J=6.1 Hz), 7.34 (1H, dd, J=5.1, 1.2 Hz), 7.25-7.27 (1H, m), 7.25 (1H, dd, J=5.1, 3.0 Hz), 7.20 (2H, d, J=8.9 Hz), 7.16-7.19 (2H, m), 6.87 (2H, d, J=8.9 Hz), 6.62-6.66 (1H, m), 3.59 (2H, q, J=6.1 Hz), 2.58 (2H, t, J=6.1 Hz).

$^{13}$C-NMR (150 MHz, CDCl$_3$) δ 170.6, 164.0, 157.3, 155.5, 139.5, 136.7, 129.9, 129.6 (2C), 128.7, 128.3, 126.4, 126.0, 120.1 (2C), 114.8, 114.3, 110.4, 36.5, 35.8.

EIMS m/z (rel. int) 402 [M+2] (8), 400 [M]$^+$ (21), 221 (36), 219 (100), 182 (24), 140 (21), 111 (46).

HREIMS m/z 400.0652 (400.0648 calculated for C$_{20}$H$_{17}$O$_3$N$_2$ClS).

Example 37

N-(3-(3-(4-Chlorophenoxy)phenylamino)-3-oxopropyl)pyridine-4-carboxamide (Compound 37)

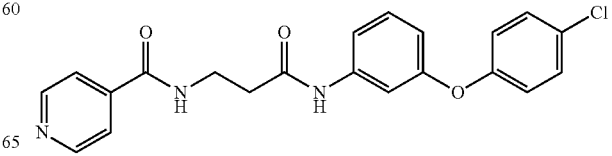

Compound 37 was synthesized according to a similar process to that of Compound 24, except that isonicotinic acid was used in place of 4-(methoxymethoxy)benzoic acid.

The product was analyzed by electron impact mass spectrometry (EIMS) and NMR. The results of EIMS and NMR are as follows.

$^1$H-NMR (600 MHz, CDCl$_3$) δ 8.93 (1H, br.s), 8.63 (2H, d, J=5.7 Hz), 7.92 (1H, br.t, J=6.1 Hz), 7.58 (2H, d, J=5.7 Hz), 7.23 (1H, t, J=2.2 Hz), 7.20 (2H, d, J=8.8 Hz), 7.19 (1H, t, J=7.9 Hz), 7.16 (1H, dd, J=7.9, 2.2 Hz), 6.87 (2H, d, J=8.8 Hz), 6.65 (1H, dd, J=7.9, 2.2 Hz), 3.66 (2H, q, J=6.2 Hz), 2.63 (2H, t, J=6.2 Hz).

$^{13}$C-NMR (150 MHz, CDCl$_3$) δ 170.4, 166.1, 157.4, 155.5, 150.3 (2C), 141.2, 139.4, 130.0, 129.7 (2C), 128.4, 121.1 (2C), 120.2 (2C), 114.8, 114.4, 110.5, 36.2, 36.1.

EIMS m/z (rel. int) 397 [M+2]$^+$ (12), 395 [M]$^+$ (33), 221 (40), 219 (100).

HREIMS m/z 395.1041 (395.1037 calculated for C$_{21}$H$_{18}$O$_3$N$_3$Cl).

Example 38

N-(3-(3-(3,4-dichlorophenoxy)phenylamino)-3-oxo-propyl)-4-hydroxybenzamide (Compound 38)

Compound 38 was synthesized according to a similar process to that of Compound 24, except that 3-(3,4-dichlorophenoxy)aniline was used in place of 3-(4-chlorophenoxy)aniline.

The product was analyzed by electron impact mass spectrometry (EIMS) and NMR. The results of EIMS and NMR are as follows.

$^1$H-NMR (400 MHz, CD$_3$OD) δ 7.62 (2H, d, J=9.0 Hz), 7.37 (1H, t, J=1.9 Hz), 7.31 (1H, dd, J=8.2, 2.2 Hz), 7.27-7.21 (2H, m), 7.01-7.08 (1H, m), 6.83-6.77 (3H, m), 6.65-6.73 (1H, m), 3.64 (2H, t, J=5.1 Hz), 2.62 (2H, t, J=5.1 Hz).

$^{13}$C-NMR (100 MHz, CD$_3$OD) δ 170.7, 168.4, 160.1, 156.1, 139.6, 132.7, 130.6, 129.8, 128.7 (2C), 128.6, 126.1, 124.5, 120.0, 117.7, 115.3, 114.9 (2C), 114.4, 110.7, 36.2, 35.8.

EIMS m/z (rel. int) 446 [M+2]$^+$ (1), 444 [M]$^+$ (2), 311 (4), 309 (27), 307 (42), 257 (9), 255 (63), 253 (100), 121 (85), 55 (93).

HREIMS m/z 444.0652 (444.0644 calculated for C$_{22}$H$_{18}$N$_2$O$_4$Cl$_2$).

Test Example 1

Method, for Confirming Luciferase Expression Inhibitory Effect Under Control of OPN Promoter A reporter vector pOPN1-luc obtained by the insertion of a human OPN promoter sequence (−765 to 23) into the multiple cloning site of pGL-3 basic vector (Promega) expresses luciferase when transfected into animal cells. The pOPN1-luc was transfected into a human non-small cell lung cancer-derived cell line A549 together with pPUR (Clontech) that expresses a puromycin resistance gene (puromycin-N-acetyl-transferase gene), and then cells expressing luciferase which could grow a puromycin-supplemented medium were selected. The selected cells were named "A549/OPNluc cells" and used for observation of luciferase expression inhibitory effect under control of OPN promoter, as described below.

A test compound was added to a culture containing A549/OPNluc cells to observe its influence on the amount of luciferase expressed in the cells. Here, it can be considered that when the test compound has a cell cytotoxity or cell growth inhibitory effect, the total expression level of luciferase is reduced due to a reduction in the number of living cells that depends on the concentration of the test compound, and therefore the luciferase expression inhibitory effect of the test compound under control of OPN promoter cannot be properly evaluated. For this reason, WST assay for quantification of cell proliferation ability or cell viability by colorimetric measurement was firstly performed to determine IC$_{50}$ (concentration for 50% inhibition of cell growth) of the test compound for cell growth. Then, luciferase activity measurement was performed to determine EC$_{50}$ (concentration for 50% inhibition of luciferase expression) of the test compound for luciferase expression under control of OPN promoter.

(1-1) WST Assay

A549/OPNluc cells were suspended in DMEM medium containing 10% fetal calf serum (FCS) and 1% penicillin/streptomycin (P/S) at 3×10$^4$ cells/mL to obtain a cell suspension, and then the cell suspension was dispensed into each well of a 96-well plate in an amount of 100 μL. In order to perform the assay in triplicate, wells were prepared for a control group, and 3 wells were prepared for each test compound-treated group at each concentration. After the dispensation, the 96-well plate was incubated in a CO$_2$ incubator (at 37° C. and 5% CO$_2$) for 24±4 hours.

The present compound was dissolved in dimethylsulfoxide (DMSO) to obtain a 50 mmol/L solution, and the compound solution was stored at −80° C. The compound solution was diluted with DMSO in 2-fold dilution series (usually, in the range of 0.31 mmol/L to 20 mmol/L) to prepare test compound solutions whose concentration varied by two fold for WST assay.

Each solution of only DMSO (control) and the diluted test compound (sample) was dispensed into each well containing the cell suspension in an amount of 0.5 μL (200-fold dilution). The solution in each well was mixed with a vortex mixer, and then the 96-well plate was incubated in a CO$_2$ incubator (at 37° C. and 5% CO$_2$) for 48±4 hours. Then, Premix WST-1 Reagent (TAKARA BIO INC.) was added in an amount of 10 μL to each well. The solution in each well was mixed with a vortex mixer, and then the 96-well plate was incubated at 37° C. and 5% CO$_2$. After 60 minutes or 120 minutes, the absorbance values (450 nm) were measured with a microplate reader (Bio-Rad; Benchmark or Thermo Scientific; Varioskan Flash).

The absorbance values of the control wells and the sample wells at each concentration were input into an Excel file to determine the percentages of absorbance values of the sample wells at each concentration with to the average absorbance value of the control wells. From the determined values, a fitted curve was determined by the method of least squares to calculate IC50.

(1-2) Luciferase Assay

The same steps as in the above-mentioned WST assay were performed in which each solution of only DMSO (control) or the diluted test compound (sample) was added in an amount of 0.5 µL to each well containing the cell suspension to achieve 200-fold dilution, and the solution in each well was mixed with a vortex mixer, and the 96-well plate was incubated in a $CO_2$ incubator (at 37° C. and 5% $CO_2$) for 48±4 hours.

Luciferase Assay Substrate (hereinafter referred to as "LAS") supplied in Luciferase Assay Systems (Promega: Cat #E1500) was dissolved in Luciferase Assay Buffer (LAB) to prepare a luciferase reagent. 5×Cell Culture Lysis Reagent (hereinafter referred to as "CCLR") was diluted by 5 times with water to prepare 1×CCLR.

After the incubation for 48±4 hours, the medium in each well was completely removed, and 1×CCLR was dispensed into each well in an amount of 50 µL. The 96-well plate was allowed to stand at room temperature for 30 minutes, and then 1×CCLR in each well was used as an assay sample. The luciferase reagent (100 µL) was placed in a tube for chemiluminescence measurement, and the assay sample (20 µL) was added to the tube and mixed with the luciferase reagent to measure chemiluminescence (Relative Luminescence Intensity: RLU) using TB 20/20 (Promega) or GloMax 20/20 (Promega).

The RLU values of the control wells and the sample wells at each concentration were input into an Excel file, and the percentages of RLU values of the sample wells at each concentration to the average RLU value of the control wells were determined. From these values, a fitted curve was determined by the method of least squares to calculate $EC_{50}$. Also, the percentages of RLU values of the sample wells at each concentration to the average RLU value of the control wells were divided by the percentages of absorbance values of the compounds in WST assay at the same concentrations as those of this assay (to the control), and a fitted curve was determined from the calculated values by the method of least squares to calculate corrected $EC_{50}$. The corrected $EC_{50}$ value is an $EC_{50}$ value corrected for a decrease in RLU based on the number of viable cells decreased depending on the concentration of the test compound for producing an inhibitory effect of cell cytotoxicity or cell growth.

Table 1 shows $IC_{50}$ values, $EC_{50}$ values, and corrected $EC_{50}$ values calculated using Compounds 1 to 38 as the test compound.

TABLE 1

| Compound No. | $IC_{50}$ (µmol/L) | $EC_{50}$ (µmol/L) | corrected $EC_{50}$ (µmol/L) |
|---|---|---|---|
| 1 | 65.9 | 17.1 | 24.5 |
| 2 | 51.0 | 26.8 | 60.3 |
| 3 | 32.5 | 32.2 | 103.2 |
| 4 | 67.1 | 27.6 | 37.0 |
| 5 | 64.9 | 19.5 | 22.6 |
| 6 | 66.0 | 8.9 | 10.2 |
| 7 | 63.3 | 35.6 | 43.7 |
| 8 | >100 | >100 | — |
| 9 | 93.7 | 41.5 | 65.6 |
| 10 | 52.8 | 31.5 | 41.7 |
| 11 | 200.3 | 165.7 | — |
| 12 | >200 | >200 | — |
| 13 | >200 | >200 | — |
| 14 | 61.1 | 5.6 | 5.0 |
| 15 | 35.4 | 5.6 | 5.3 |
| 16 | 34.9 | 9.8 | 12.5 |
| 17 | 47.7 | 3.7 | 4.2 |
| 18 | 49.4 | >50 | — |
| 19 | >100 | 6.8 | 7.8 |
| 20 | >100 | 16.3 | 18.0 |
| 21 | 95.9 | 16.1 | 17.0 |
| 22 | >100 | 42.2 | 50.4 |
| 23 | >100 | 71.5 | 82.8 |

TABLE 1-continued

| Compound No. | $IC_{50}$ (µmol/L) | $EC_{50}$ (µmol/L) | corrected $EC_{50}$ (µmol/L) |
|---|---|---|---|
| 24 | 29.4 | 7.5 | 11.4 |
| 23 | 87.3 | 40.6 | 50.9 |
| 26 | 86.2 | 20.3 | 27.1 |
| 27 | 71.9 | 19.8 | 26.6 |
| 28 | >100 | 41.5 | 53.7 |
| 29 | >100 | 51.4 | 62.1 |
| 30 | 52.3 | 7.0 | 12.6 |
| 31 | 26.9 | 9.3 | 11.0 |
| 32 | 24.7 | 8.0 | 9.3 |
| 33 | 25.9 | 8.5 | 11.1 |
| 34 | 55.1 | 24.9 | 32.9 |
| 35 | 74.6 | 23.8 | 41.4 |
| 36 | 43.3 | 22.0 | 31.2 |
| 37 | 60.1 | 15.6 | 20.9 |
| 38 | 17.3 | 4.6 | 7.5 |

Test Example 2

Inhibitory Effects of Compounds 1 6, 19, 26, and 38 on OPN Production in Human Cancer Cell-Derived Cell Lines Brefelamide (Compound 1) was added to a culture liquid containing cells of human liver cancer-derived cell line HepG2, human non-small cell lung cancer-derived cell line A549, human renal cell carcinoma-derived cell line OUR-10, or human pancreatic cancer-derived cell line QGP-1, and the amount of OPN in the culture supernatant after 2 days was measured using Human Osteopontin Immunoassay kit (R&D systems). The confirmation test was performed by comparison of the OPN amount of Compound 1-treated group with that of DMSO-treated group (control group). In addition, Compounds 6, 19, 26, and 38 which are brefelamide derivatives were added to a culture liquid containing cells of human non-small cell lung cancer-derived cell line A549, and a similar confirmation test to the above-mentioned test was performed.

Compounds 1, 6, 19, 26, and 38 have also a cell growth inhibitory effect. Thus, in order to properly evaluate the inhibitory effect of the compounds on the OPN production, the 1×CCLR solution used in luciferase assay was added to cells remaining in each well after removal of culture supernatant to prepare a cell lysate, and the amount of protein in the cell lysate was measured using BCA Protein Assay Kit (Thermo Scientific). The influence of Compound 1 on the amount of the OPN production was evaluated by comparison of the amount of OPN per milligram of protein.

(2-1) Preparation of Cell Culture Liquid (FIGS. 1, 2, 5, and 8 to 10)

HepG2 cells or A549 cells were suspended in DMEM medium containing 10% FCS and 1% P/S at $4\times10^4$ cells/mL to obtain a cell suspension, and the cell suspension was dispensed into each well of a 24-well plate in an amount of 500 µL. In order to perform the test in triplicate, 3 wells were prepared for each control group, and 3 wells were prepared for each test compound-treated group at each concentration. The 24-well Plate was incubated in a $CO_2$ incubator (at 37° C., and 3% $CO_2$) for 24±4 hours.

(2-2) Preparation of Cell Culture Liquid (FIGS. 3 and 4)

OUR-10 cells or QGP-1 cells were suspended in RPMI1640 medium containing 10% FCS and 1% P/S at $4\times10^4$ cells/mL to obtain a cell suspension, and the cell suspension was dispensed into each well of a 24-well plate in an amount of 500 µL. In order to perform the test in duplicate, 2 wells were prepared for each control group, and 2 wells were prepared for each test compound-treated group at each concentration. The 24-well plate was incubated in a $CO_2$ incubator (at 37° C., and 5% $CO_2$) for 24±4 hours.

(2-3) Addition of Compound

Compound 1, 6, 19, 26, and 38 which are test compounds were dissolved in DMSO to prepare a 50 mmol/L solution of each compound, and the solutions were stored at −80° C. The solution of Compound 1 was diluted with DMSO to prepare 2.5 mmol/L and 5 mmol/L solutions (FIG. 1), 3.125 mmol/L and 6.25 mmol/L solutions (FIG. 2), 6.25 mmol/L and 12.5 mmol/L solutions (FIG. 3), or 5 mmol/L and 10 mmol/L solutions (FIG. 4). The two solutions of Compound 1 at different concentrations were added in an amount of 2 µL per well to wells in which HepG2, A549, OUR-10, or QGP-1 cells were culture, respectively. Only DMSO was added in an amount of 2 µL to each control well.

Similarly, the 50 mmol/L solution of Compound 6 was stared at −80° C., and the solution was diluted with DMSO to prepare 2.5 mmol/L and 5 mmol/L solutions (FIG. 5). The two solutions of Compound 6 at different concentrations were added in an amount of 2 µL per well to wells in which A549 cells were cultured. Only DMSO was added in an amount of 2 µL to the control well.

Also, the 50 mmol/L solutions of Compounds 19, 26, and 38 were stored at −80° C., and each solution was diluted with DMSO to prepare 3.125 mmol/L and 6.25 mmol/L solutions (FIGS. 8 to 10). The two solutions of Compound 19, 26, or 38 at different concentrations were added in an amount of 2 µL per well to wells in which A549 cells were cultured, respectively. Only DMSO was added in an amount of 2 µL to each control well.

(2-4) Cell Culture and Preparation of Sample

The 24-well plate was shaken to mix the solution in each well, and was then incubated in a $CO_2$ incubator (at 37° C. and 5% $CO_2$) for 48±4 hours. Then, the total amount of the resulting culture supernatant was transferred into a 1.5 mL tube, and D-PBS(−) (500 µL) was added to each well containing cells.

The 24-well plate was gently shaken to remove D-PBS (−), and then 5×CCLR used in luciferase assay was diluted to 5 times with water to prepare 1×CCLR. The prepared 1×CCLR was dispensed into each well in an amount of 200 L. The 24-well plate was then rocked on a rocking shaker for 15 minutes.

After rocking the 24-well plate for 15 minutes, the cell lysate in each well of the 24-well plate was transferred into a 1.5 mL tube and centrifuged in a high-speed refrigerated micro centrifuge at 4° C. and 15,000 rpm for 1 minute to remove impurities such as cell debris. The resulting supernatant was used as a sample for protein assay.

On the other hand, the culture supernatant transferred into a 1.5 mL tube was centrifuged in a high-speed refrigerated micro centrifuge at 4° C. and 15,000 rpm for 1 minute to remove impurities such as cell debris. The resulting supernatant was used as a sample for ELISA.

(2-5) Measurement of Amount of OPN Protein

The samples for ELISA other than the sample of QGP-1 cells were diluted in the following manner. The sample of QGP-1 cells was used as an undiluted solution.

A549 cells (20-fold dilution): sample 5 µL+culture medium 95 µL

HepG2 cells (80-fold dilution): sample 2 µL+culture medium 158 µL

OUR-10 cells (10-fold dilution): sample 10 µL+culture medium 90 µL

Water (1 mL) was added into a vial of OPN standard supplied in an ELISA kit, and the solution was gently mixed and allowed to stand at room temperature for 15 minutes to prepare 200 ng/mL of OPN Standard. Then, as shown in Table 2, the OPN standard was serially diluted with a diluent RD5-24 supplied in the kit.

TABLE 2

| Vial | Amount of RD5-24 to be prepared (µL) | Type and amount of OPN standard solution to be added | OPN concentration (ng/mL) |
| --- | --- | --- | --- |
| — | — | — | 200 |
| A | 540 µL | 60 µL of 200 ng/mL OPN Standard | 20 |
| B | 300 µL | 300 µL of vial A | 10 |
| C | 300 µL | 300 µL of vial B | 5 |
| D | 300 µL | 300 µL of vial C | 2.5 |
| E | 300 µL | 300 µL of vial D | 1.25 |
| F | 300 µL | 300 µL of vial E | 0.625 |
| G | 300 µL | 300 µL of vial F | 0.312 |
| H | 300 µL | — | 0 = Blank |

The necessary number of OPN Microplates and RD1-6 supplied in the kit were prepared, and RD1-6 was dispensed into each well in an amount of 100 µL. The diluted OPN Standard (vial A to H) or the sample was further added in an amount of 50 µL to each well containing RD1-6. Then, the upper end of each well was covered with a seal, and the OPN microplates were allowed to stand at room temperature for 2 hours. In this period, Wash Buffer Concentrate supplied in the kit was diluted with water to prepare Wash Buffer.

After allowing the OPN microplates to stand for 2 hours, the liquid in each well was removed. The Wash Buffer was dispensed into each well in an amount of 250 µL and then removed to wash each well. This washing operation was performed 4 times.

OPN conjugate was dispensed into each well in an amount of 200 µL. The upper end of each well was then covered with a seal, and the OPN microplates were allowed to stand at room temperature for 2 hours. In this period, Color Reagent A and Color Reagent B supplied in the kit were mixed in an equal amount to prepare Substrate Solution.

After allowing the OPN microplates to stand for 2 hours, the liquid in each well was removed. The Wash Buffer was dispensed into each well in an amount of 250 µL and then removed to wash each well. This washing operation was performed 4 times.

The Substrate Solution was dispensed into each well in an amount of 200 µL, and then the OPN microplates were allowed to stand at room temperature for 30 minutes while being shielded from light. Then, Stop Solution supplied in the kit was added into each well in an amount of 50 µL, and the liquid in each well was gently mixed with a vortex mixer until the color of the liquid in each well was entirely changed from blue to yellow. After mixing, absorbance values (at 450 cm and 570 nm) were measured using a microplate reader (Bio-Rad; Benchmark or Thermo Scientific; Varioskan Flash). The subtraction of the value at OD 570 nm from the value at OD 450 nm was performed on all the measured data, and the thus determined values were used for calculation performed later.

A calibration curve was prepared from the absorbance values of the calibration curve samples. The amount of OPN protein was calculated using the formula of the calibration curve from the absorbance value of each sample.

(2-6) Measurement of Total Amount of Protein in Cells

The sample for protein assay (10 μL) and water (90 μL) were mixed to make 10-fold dilution. Calibration curve samples were prepared by diluting a BSA solution with water as shown in Table 3.

TABLE 3

| Vial | Water (μL) | Type and amount of BSA solution to be added | BSA concentration (ng/mL) |
|---|---|---|---|
| — | — | — | 2000 |
| A | 140 μL | 20 μL of 2000 ng/mL BSA | 250 |
| B | 80 μL | 80 μL of vial A | 125 |
| C | 90 μL | 60 μL of vial B | 50 |
| D | 80 μL | 80 μL of vial C | 25 |
| E | 80 μL | 20 μL of vial D | 5 |
| F | 80 μL | — | 0 |

BCA Reagent A and BCA Reagent B supplied in a protein assay kit were mixed (50:1) to prepare Working Reagent. The calibration curve sample (vial A to F) or the 10-fold diluted sample for protein assay was dispensed into each well of a 96-well plate in an amount of 25 μL. In order to perform the assay in duplicate, 2 wells were prepared for a control group, and 2 wells were prepared for each test compound-treated group at each concentration.

The Working Reagent was added in an amount of 200 μL to each well, and the solution in each well was mixed for 30 seconds with a vortex mixer. The 96-well plate was heated at 60° C. for 30 minutes and then allowed to stand at room temperature for 15 minutes. Then, absorbance values (at 550 nm) were measured with a microplate reader (Bio-Rad; Benchmark or Thermo Scientific; Varioskan Flash).

A calibration curve was prepared from the absorbance values of the calibration curve samples, and the total protein concentration of the diluted sample in each well as calculated using the formula of the calibration curve. Further, the total protein concentration was multiplied by the dilution factor (10) to calculate the total protein concentration of the sample.

(2-7) Expression of OPN (Protein) Amount

The OPN amount (the amount per milliliter of culture supernatant) was converted to the amount of OPN per total amount (0.5 mL) of the sample for ELISA. This converted value was divided by the amount of protein in the total amount (0.2 mL) of the sample for protein assay derived from the same well as the sample for measuring OPN amount for conversion to the amount of CON per milligram of total protein in cells. Based on the amount of OPN per milligram of protein, the influence on the addition of Compound 1 was evaluated.

(2-8) Statistical Processing

The statistical processing of the CON amounts was performed using Excel statistics, Statcel 3 The CON amounts of the samples of Compound 3 (test compound)-treated groups were subjected to Dunnett test for comparison with those of the control group on an Excel file.

FIG. 1 is a graph showing the inhibitory effect of Compound 1 on the OPN production in HepG2 cells. It was shown that there was no difference in the amount of the OPN production between Compound 1-treated group (10 μmol/L) and control group. On the other hand, it was demonstrated that Compound 1-treated group (20 μmol/L) significantly inhibited the CON production in HepG2 cells at a significance level of less than 1% as compared to the control group.

FIG. 2 is a graph showing the inhibitory effect of Compound 1 on the OPN production in A549 cells. It was shown that when the concentration of Compound 1 was increased from 12.5 μmol/L to 25 μmol/L, the OPN production was inhibited depending on the concentration of Compound 1. Also, it was demonstrated that Compound 1-treated groups (12.5 μmol/L and 25 μmol/L) significantly inhibited the OPN production in A549 cells at a significance level of less than 1% as compared to the control group.

FIG. 3 is a graph showing the inhibitory effect of Compound 1 on the OPN production in OUR-10 cells. The amounts of the OPN production in two control groups performed in duplicate were the almost same, and those of two Compound 1-treated groups performed in duplicate were the almost same. It was demonstrated that Compound 1-treated groups (25 μmol/L and 50 μmol/L) significantly inhibited the OPN production in OUR-10 cells as compared to the control groups.

FIG. 4 is a graph showing the inhibitory effect of Compound 1 on the OPN production in QGP-1 cells. The amounts of OPN production in two control groups performed in duplicate were the almost same, and those of two Compound 1-treated groups performed in duplicate were the almost same. It was shown that there was no difference in the amount of the OPN production between Compound 1-treated groups (20 μmol/L) and the control groups. On the other hand, it was demonstrated that Compound 1-treated groups (40 μmol/L) significantly inhibited the OPN production in QGP-1 cells as compared to the control groups.

FIG. 5 is a graph showing the inhibitory effect of Compound 6 on the OPN production in A549 cells. It was shown that when the concentration of Compound 6 was increased from 10 μmol/L to 20 μmol/L, the OPN production was inhibited depending on the concentration of Compound 6. Also, it was demonstrated that when Compound 6-treated groups (10 μmol/L and 20 μmol/L) significantly inhibited the OPN production in A549 cells at a significance level of less than 1% as compared to the control group.

FIG. 8 is a graph showing the inhibitory effect of Compound 19 on the OPN production in A549 cells. It was shown that when the concentration of Compound 19 was increased from 12.5 μmol/L to 25 μmol/L, the OPN production was inhibited depending on the concentration of Compound 19. Also, it was demonstrated that Compound 19-treated groups (12.5 μmol/L and 25 μmol/L) significantly inhibited the OPN production in A549 cells at a significance level of less than 1% as compared to the control group.

FIG. 9 is a graph showing the inhibitory effect of Compound 26 on the OPN production in A549 cells. It was shown that when the concentration of Compound 26 was increased from 12.5 μmol/L to 25 μmol/L, the OPN production was inhibited depending on the concentration of Compound 26. Also, it was demonstrated that Compound 19-treated groups (12.3 μmol/L and 25 μmol/L) significantly inhibited the OPN production in A549 cells at a significance level of less. than 1% as compared cc the control group.

FIG. 10 is a graph showing the inhibitory effect of Compound 38 on the OPN production in A549 cells. It was shown that when the concentration of Compound 38 was increased from 12.5 μmol/L to 25 μmol/L, the OPN production was inhibited depending on the concentration of Compound 38. Also, it was shown that Compound 38-treated groups (12.5 μmol/L and 25 μmol/L) significantly inhibited the OPN production in A549 cells at a significance level of less than 1% as compared to the control group.

FIGS. 1 to 4 show that Compound 1 could inhibit the OPN production in cells of human liver cancer-derived cell line HepG2, human non-small cell lung cancer-derived cell line A549, human renal cell carcinoma-derived cell line OUR- 10, and human pancreatic cancer-derived cell line QGP-1. FIG. 5 shows that Compound 6 could inhibit the OPN production in cells of human non-small cell lung cancer-derived cell line A549. In addition, FIGS. 8 to 10 show that Compounds 19, 26, and 38 could inhibit the OPN production in cells of human non-small cell lung cancer-derived cell line A549.

Test Example Effect of Compound 1 on Inhibition of Wound-Healing Capacity of Human Non-Small Cell Lung Cancer Derived Cell Line A549

The experimental results shown in FIGS. 1 to 4 revealed that brefelamide (Compound 1) that inhibits luciferase expression under control of OPN promoter actually inhibited the OPN production as a protein. In the next stage, a determination was made as to whether or not the physiological function of cells induced by the OPN production was inhibited with Compound 1 as a test compound. The determination was made by performing. Wound-Healing assay in cells. This assay is commonly known as a method for evaluating cell migration capacity. When a wound is made in a cell monolayer by scratching some cells with a pipette tip or the like, the wound is closed by migration of cells around the wound. The influence of a test compound on such function was observed by adding the test compound to a cell culture liquid.

(3-1) Method for Wound-Healing Assay

Cells of human non-small cell lung cancer-derived cell line A549 were suspended in OMEN medium containing 10% FCS and 1% P/S at $3.5 \times 10^5$ cells/mL to obtain a cell suspension, and the cell suspension was dispensed into each well of a 24-well plate in an amount of 500 μL ($1.75 \times 10^5$ cells). In order to perform the assay in triplicate, 3 wells were prepared for a control group, and 3 wells were prepared for test compound-treated groups at each concentration. After the dispensation, the 24-well plate was incubated in a $CO_2$ incubator (at 37° C. and 5% $CO_2$) for 24±4 hours.

After the incubation, the medium was removed from all of the wells, and a medium (serum-free medium) prepared by adding 0.1% bovine serum albumin (BSA) and 1% P/S to DMEM was dispensed into all of the wells in an amount of 500 μL per well. The 24-well plate was shaken, and then the medium was again removed from all of the wells. After removing the medium, the serum-free medium was dispensed into all of the wells in an amount of 500 μL per well.

Compound 1 as a test compound was dissolved in DMSO to prepare a 50 mmol/L solution, and the solution was stored at −80° C. The solution of Compound 1 was diluted with DMSO to prepare a 3.125 mmol/L solution and a 6.25 mmol/L solution. The solution of Compound 1 (3.125 mmol/L or 6.25 mmol/L) was added in an amount of 2 μL to each well in which A549 cells were cultured. Only DMSO was added in an amount of 2 μL to each control well.

The 24-well plate was shaken to mix the solution in each well, and was then incubated in a $CO_2$ incubator (at 37° C. and 5% $CO_2$) for 24±4 hours.

The cells in the 24-well plate were observed with a microscope to confirm that the cells were 100% confluent. Then, cells on the bottom surface of each well in the plate were scratched at three positions with a 20 μL-micropipette tip. As the microscope, IX71 inverted research microscope (OLYMPUS CORPORATION) equipped with Retiga-2000 Fast 1394 Color (QImaging) as a CCD camera system was used.

The wounds were observed with the microscope, and their images were taken in a single shot by adjusting the microscope. The magnification of the microscope was set to 40× (eyepiece: 10×, objective: 4×). After taking images, the 24-well plate was incubated in a $CO_2$ incubator (at 37° C. and 5% $CO_2$) for 48±4 hours.

After the incubation, the wounds were observed with the microscope, and their images were taken in a single shot by adjusting the microscope. The magnification of the microscope was set to 40× (eyepiece: 10×, objective: 4×).

Based on the taken images, the areas of the wounds were determined using Image-Pro Plus 7.0J (MediaCybernetics). Then, the wound-healing rate (%) was calculated according to the following calculation formula: Wound-healing rate (%)=100−[the area of the wound after 2 days from injury/the area of the wound just after injury]×100. The average wound-healing rates (%) of the control group and two Compound 1-treated groups at different concentrations were calculated. Also, the percentage of each of the wound-healing rates of the compound-treated groups to that of the control group was calculated.

(3-2) Statistical Processing

The statistical processing of calculated values of the wound-healing rate was performed using Excel statistics, Statcel 3. Specifically, all of the wound-healing rates of Compound 1-treated groups were subjected to Dunnett test for comparison with the control group on an Excel file.

FIG. 6 is a graph showing the wound-healing inhibitory effect of Compound 1 in A549 cells. It was shown that there was no difference in the wound-healing rate between Compound 1-treated group (12.5 μmol/L) and the control group. On the other hand, it was demonstrated that there was a significant difference in the wound-healing rate between Compound 1-treated group (25 μmol/L) and the control group at a significance level of less than 1%.

That is, it was found that Compound 1 (25 μmol/L) could significantly inhibit the wound-healing in A549 cells.

Test Example 4

Effect of Compounds 1 and 6 on Inhibition of Metastatic and Invasive Capacity of Human Non-Small Cell Lung Cancer-Derived Cell Line A549

As a second test for determining whether or not the physiological function of cells induced by the OPN production is inhibited with a test compound, Matrix-Invasion assay was performed. In this assay, cups (inserts) whose bottom was covered with a membrane having φ8 μm pores coated with collagen or laminin (Matrigel, BD Bioscience) that is an extracellular matrix component and a 24-well plate for inserting the inserts were prepared. The cells suspended in a serum-free medium were placed in the inside insert, and a medium containing a substance inducing metastasis and invasion of cells (i.e. fetal calf serum) was injected into each well of the outside 24-well plate to determine the number of cells passing through the Matrigel-coated membrane of the insert and coming into the outside well.

Matrigel is an artificial basement membrane matrix for cell culture, more specifically a solubilized basement membrane preparation extracted from Engelbreth-Holm-Swarm (EHS) mouse sarcoma rich in extracellular matrix protein. Matrigel mainly contains laminin, collagen IV, heparan sulfate proteoglycan, and entactin/nidogen. Matrigel also contains TGF-β, epidermal growth factor, insulin-like growth factor, fibroblast growth factor, tissue plasminogen activator, and other growth factors naturally produced by EHS tumors.

Specifically, a fluorescent dye was introduced into A549 cells invading outside the membrane, and then the cells were separated from the membrane to measure their fluorescence intensity. At the same time, a fluorescent dye was introduced into a known number of cells for preparing a calibration curve, and a calibration curve was prepared from their fluorescence intensity. Then, the number of invading cells of a test sample containing an unknown number of cells was determined from the fitted curve.

Cancer cells produce OPN by the stimulation of fetal calf serum added to the outside medium. When OPN is present in the culture liquid, the cells therein bind to OPN, and thereby Matrix Metalloproteinase (MMP) that is a collagen-degrading enzyme is produced. As a result, Matrigel is dissolved and the migration capacity of the cells is enhanced, and thus the cells transfer to the outside well. The inhibitory effects of brefelamide (Compound 1) and the derivative thereof, Compound 6 which suppress luciferase expression under control of OPN promoter on the matrix-invasive function of A549 cells were observed.

(4-1) Method for Matrix-Invasion Assay

The cells of human non-small cell lung cancer-derived cell line A549 were suspended in DMEM medium containing 10% FCS and 1% P/S at $1.8 \times 10^5$ cells/mL to obtain a cell suspension. The cell suspension was dispensed into a 75 cm$^2$ flask in an amount of 10 mL and was incubated in a $CO_2$ incubator (at 37° C. and 5% $CO_2$) for 24±4 hours. In the same manner, a suspension of A549 cells was prepared at $6 \times 10^4$ cells/mL in order to prepare a calibration curve, and the suspension was dispensed into a 25 cm$^2$ flask in an amount of 5 mL and was incubated in a $CO_2$ incubator (at 37° C. and 5% $CO_2$) for 24±4 hours. This day was counted as Day 0 of operation.

[Next Day: Day 1 of Operation]

The medium was removed from the 75 cm$^2$ flask in which the cells were seeded. The DMEM medium (serum-free medium) containing 0.1% BSA and 1% P/S was dispensed into the flask without the medium in an amount of 10 mL, and the flask was tilted so that the entire cell surface was evenly covered with the medium. Then, the medium was removed from the flask.

The serum-free medium was dispensed into the flask without the medium in an amount of 10 mL. Then, the flask was incubated in a $CO_2$ incubator (at 37° C. and 5% $CO_2$) for 24±4 hours.

[Day 2 of Operation]

Matrigel (10 mg/mL: BD Biosciences) was melted on ice. Cell culture inserts (for 24-well plates, with 8.0 μm pores: BD Biosciences) and the serum-free medium were ice-cooled. The Matrigel was diluted to 25 times with the ice-cooled serum-free medium to prepare a Matrigel solution.

A necessary number of cell culture inserts were set in the 24-well plate, and the Matrigel solution was dispensed into each cell culture insert in an amount of 50 μL, and then spread over the membrane with a pipette tip. Then, the 24-well plate was incubated in a $CO_2$ incubator (at 37° C. and 3% $CO_2$) for 1 to 2 hours.

The cell culture supernatant was removed from the 75 cm$^2$ flask in which medium replacement with the serum-free medium was performed on the previous day. Calcium-magnesium-free phosphate buffered saline (D-PBS(−)) was dispensed into the flask in an amount of 10 mL, and the flask was tilted so that the entire cell surface was evenly covered with the medium, and then D-PBS(−) was removed (the operation is referred to as "washing operation" with D-PBS (−)). Then, Cell Dissociation Solution (CDS: Sigma) was dispensed into the flask in an amount of 3 to 5 mL. The flask containing CDS was incubated in a $CO_2$ incubator (at 37° C. and 5% $CO_2$) for about 20 minutes (with rocking every 5 minutes) to dissociate the cells from the bottom of the flask (the operation is referred to as "cell dissociation" with CDS).

The flask was centrifuged at 300×g, and then the supernatant was removed and the cells were suspended in 5 mL of the serum-free medium to obtain a cell suspension. A part of the suspension (10 μL) was taken and mixed with a 0.4% trypan blue solution (10 μL) with gentle pipetting. Then, the number of cells was counted using Burker-Turk counting chamber to determine a cell concentration (the operation is referred to "cell counting").

A cell suspension with a cell concentration of $2 \times 10^5$ cells/mL was prepared in an amount of 8 mL using the serum-free medium. The surfaces of the cells were coated with the Matrigel solution, and then the prepared cell suspension was gently dispensed into each culture insert incubated in a $CO_2$ incubator for 1 to 2 hours in an amount of 0.5 mL ($1 \times 10^5$ cells). The assay was performed in triplicate.

The DMEM medium containing 10% FCS and 1% P/S was dispensed into 15 mL tubes in an amount of 5 mL per tube. The 50 mmol/L solution of Compound 1 in DMSO was dispensed into each tube in an amount of 1.25 μL (final concentration: 12.5 μmol/L) or 2.5 μL (final concentration: 25 μmol/L) to prepare a Compound 1-supplemented medium. Similarly, the 50 mmol/L solution of Compound 6 in DMSO was dispensed into the tube in an amount of 1 μL (final concentration: 10 μmol/L) to prepare a Compound 6-supplemented medium. DMSO (5 μL) was added to the DMEM medium containing 10% FOS and 1% P/S (5 mL) to prepare a control-supplemented medium.

Compound 1-supplemented medium, Compound 6-supplemented medium, or the control-supplemented medium was dispensed into each well of the 24-well plate in an amount of 0.75 mL through a gap between the culture insert and the plate. Then, the 24-well plate was incubated in a $CO_2$ incubator (at 37° C. and 5% $CO_2$) for 48±4 hours.

[Day 3 of Operation]

The medium containing A549 cells cultured in a 25 cm$^2$ flask was removed, and then replaced with 5 mL of the serum-free medium. Then, the 25 cm$^2$ flask was incubated in a $CO_2$ incubator (at 37° C. and 5% $CO_2$) for 48±4 hours.

[Day 4 of Operation]

A vial containing calcein AM (50 μg/vial: BD Biosciences) was cooled to room temperature, and DMSO (30 μL) was added thereto and mixed to prepare a calcein AM solution. CDS was dispensed into a 15 mL tube in an amount of 5 mL, and the calcein AM solution (6 μL) was added thereto and mixed with CDS to prepare a 1×calcein AM solution (calcein AM solution for inserts under test. On the other hand, CDS was dispensed into a 1.5 mL tube in an amount of 1.5 mL, and the calcein AM solution (3.6 μL) was added thereto and mixed with CDS to prepare a 2×calcein AM solution (calcein AM solution for calibration curve).

(4-2) Preparation of Cells for Preparing Calibration Curve

The cell culture supernatant was removed from the 25 cm$^2$ flask in which medium replacement was performed on the previous day, and the above-described washing operation was performed with D-PBS(−) (5 mL). Further, the above-described cell dissociation was performed with CDS (3 mL). Then, the above-described cell counting was performed, and a cell suspension at a concentration of $5 \times 10^5$ cells/mL was prepared with CDS. As shown in Table 4, the cell suspension was diluted with CDS. The cell suspension in each of vials A to H was dispensed into each well of a 96-well black plate (Corning) in an amount of 50 μL. The assay was performed in triplicate.

TABLE 4

| Vial | Cells/mL | Mixing ratio | | Cells/well |
|---|---|---|---|---|
| | | Suspension (mL) | CDS (mL) | |
| A | $5 \times 10^5$ | Cell suspension | | 25000 |
| B | $2 \times 10^5$ | Vial A 0.4 | 0.6 | 10000 |
| C | $1 \times 10^5$ | Vial B 0.5 | 0.5 | 5000 |
| D | $5 \times 10^4$ | Vial C 0.5 | 0.5 | 2500 |
| E | $2 \times 10^4$ | Vial D 0.4 | 0.6 | 1000 |
| F | $1 \times 10^4$ | Vial E 0.5 | 0.5 | 500 |
| G | $5 \times 10^3$ | Vial F 0.5 | 0.5 | 250 |
| H | 0 | 0 | 0.5 | 0 |

(4-3) Calcein AM Staining

D-PBS(−) was dispensed into each well of a fresh 24 well-plate in an amount of 0.75 ml. The medium in each insert was removed with a pipette while the insert was picked up with tweezers, and the insert was transferred into each well containing 0.75 mL of D-PBS(−). D-PBS(−) was dispensed into each insert in an amount of 0.5 mL to wash the insert with D-PBS(−).

A new 24-well plate was prepared, and the 1×calcein AM solution was dispensed into each well of the 24-well plate in an amount of 0.35 mL. D-PBS(−) in each insert washed with D-PBS(−) was removed with a pipette while the insert was picked up with tweezers, and the insert was transferred into each well containing the 1×calcein AM solution (fluorescence staining of cells in inserts under test). The 24-well plate with the transferred inserts was incubated in a $CO_2$ incubator (at 37° C. and 5% $CO_2$) for 1 hour while the side of the plate was gently tapped every 30 minutes.

During the incubation, the 2×calcein AM solution was dispensed into each well of the 96-well black plate containing the cell suspension in an amount of 50 μL, and the 96-well black plate was wrapped with aluminum foil and allowed to stand at room temperature (staining of cells for calibration curve).

(4-4) Fluorescence Measurement

After the incubation for 1 hour, the 24-well plate with inserts was carefully shaken so that the liquid in each well was mixed without spilling. Then, each insert was removed with tweezers from each well of the 24-well plate. The liquid in each well without the insert was transferred into 3 wells of a new 96-well black plate in an amount of 100 μL per well (plate for cells in inserts under test).

The fluorescence in each well of the 96-well black plates for cells for calibration curve and cells in inserts under test was measured using a microplate reader (Molecular Device; SpectraMax M5 or Thermo Scientific; Varioskan Flash) (excitation: 485 nm, emission: 520 nm).

(4-5) Calculation of Total Number of Invading Cells

The fluorescence intensity (RLU) values of the cells for calibration curve were input into Excel to determine the formula of a fitted curve (calibration curve) by the method of least squares. The number of invading cells was calculated according to the formula of the calibration curve from the fluorescence intensity value per well of the 96-well plate. The thus calculated number of invading cells was multiplied by 3.5 to obtain the total number of invading cells per well of the 24-well plate. Further, since the assay was performed in triplicate, the average of total numbers of invading cells of 3 wells was calculated.

(4-6) Statistical Processing

Statistical processing was performed using Excel statistics, Statcel 3. The total numbers of invading cells of Compound 1-treated group and Compound 6-treated group were subjected to Dunnett test for comparison with those of the negative control group (control group) on an Excel file.

FIG. 7 is a graph showing the inhibitory effect of Compound 1 or Compound 6 on the matrix invasion by A549 cells. When the numbers of invading cells in Compound 1-treated groups (12.5 μmol/L and 25 μmol/L) were compared with that of the control group, the number of invading cells was decreased depending on the concentration of Compound 1. It was demonstrated that Compound 1-treated groups (12.5 μmol/L and 25 μmol/L) significantly inhibited the numbers of invading A549 cells at significance levels of less than 5% and 1%, respectively, as compared to the control group. In addition, it was demonstrated that Compound 6-treated groups (10 μmol/L) significantly inhibited the number of invading A549 cells at a significance level of less than 5% as compared to the control group. That is, it was found that Compound 1 could significantly inhibit the matrix invasion by A549 cells at concentrations of 12.5 and 25 μmol/L, and Compound 6 could significantly inhibit the matrix invasion at a concentration of 10 μmol/L.

INDUSTRIAL APPLICABILITY

The present compound or a pharmaceutically acceptable salt thereof has a potent inhibitory effect of the osteopontin production, and thus is useful for the treatment and/or prophylaxis of a disease associated with the enhancement of the osteopontin production including. cancer.

The invention claimed is:

1. A compound of formula:

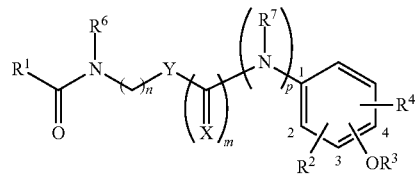

wherein $R^1$ is cyclohexyl, tetrahydropyranyl, pyridyl, thienyl, or phenyl wherein the cyclohexyl, tetrahydropyranyl, pyridyl, thienyl, and phenyl are unsubstituted or substituted with one group or the same or different two or more groups selected independently from the group consisting of halogen, hydroxy, amino, $C_{1-4}$ acylamino, $C_{1-6}$ alkyl, and $C_{1-6}$ alkoxy at any replaceable positions;

$R^2$ is hydrogen atom, amino, or hydroxy that is linked at the 2-position of the benzene ring;

$OR^3$ is linked at the 3-position of the benzene ring, and $R^3$ is phenyl which is unsubstituted or substituted with one group or the same or different two or more groups selected independently from the group consisting of halogen, hydroxy, $C_{1-6}$ alkyl, $C_{1-6}$ haloalkyl, $C_{1-6}$ alkoxy, and $C_{1-6}$ haloalkoxy at the 3- and/or 4-position (s);

$R^4$ is hydrogen atom or halogen;

$R^6$ and $R^7$ are independently hydrogen atom or $C_{1-4}$ alkyl;

n is 0 to 4, provided that when n is 1 to 4 and $R^6$ is $C_{1-4}$ alkyl, the terminal carbon atom of $R^6$ may be combined with any one carbon atom of the alkylene group in the parenthesis for n to form a 4- to 6-membered ring;

m is 0 or 1;

p is 0 or 1;

X is O, or when p is 0 and $R^2$ is amino or substituted amino which is linked at the 2-position of the benzene ring, X may be CH connecting the nitrogen atom in $R^2$ to form a pyrrole ring; and Y is $CH_2$ or NH;

or a pharmaceutically acceptable salt thereof, provided that the following compound is excluded:

N-(3-(2-amino-3-(4-hydroxyphenoxy)phenyl)-3-oxopropyl)-4-hydroxybenzamide.

2. The compound according to claim 1 represented by formula (I):

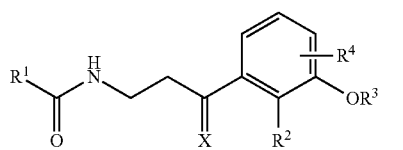

wherein $R^1$, $R^2$, $R^3$, $R^4$, and X is as defined in claim 1, or a pharmaceutically acceptable salt thereof.

3. The compound of claim 1 or a pharmaceutically acceptable salt thereof wherein $R^1$ is phenyl which is substituted with the group(s) selected independently from halogen, hydroxy, amino, $C_{1-4}$ acylamino, or $C_{1-6}$ alkoxy at the 3- and/or 4-position(s).

4. The compound according to claim 1 or a pharmaceutically acceptable salt thereof wherein $R^3$ is phenyl which is substituted with the group(s) selected independently from halogen, hydroxy, $C_{1-6}$ alkyl, $C_{1-6}$ haloalkyl, $C_{1-6}$ alkoxy, or $C_{1-6}$ haloalkoxy at the 3- and/or 4-position(s).

5. The compound according to claim 1 or a pharmaceutically acceptable salt thereof wherein $R^4$ is hydrogen atom.

6. The compound according to claim 1 or a pharmaceutically acceptable salt thereof wherein m is 1, X is O, and p is 1.

7. The compound according to claim 1 or a pharmaceutically acceptable salt thereof wherein n is 1 to 4, and $R^6$ is $C_{1-4}$ alkyl and further the terminal carbon atom of $R^6$ is combined with any one carbon atom of the alkylene group in the parenthesis for n to form a 4- to 6-membered ring.

8. A compound selected from the group consisting of:
4-hydroxy-N-(2-(7-(4-hydroxyphenoxy)-1H-indol-3-yl)ethyl)benzamide;
N-(3-(2,3-dihydroxyphenyl)-3-oxopropyl)-4-(4-hydroxyphenoxy)benzamide;
N-(3-(2-amino-3-(4-hydroxyphenoxy)phenyl)-3-oxopropyl)-4-methoxybenzamide;
N-(3-(2-amino-3-(4-methoxyphenoxy)phenyl)-3-oxopropyl)-4-methoxybenzamide;
N-(3-(2-amino-3-(4-methoxyphenoxy)phenyl)-3-oxopropyl)-4-hydroxybenzamide;
N-(3-(2-amino-3-(4-hydroxyphenoxy)phenyl)-3-oxopropyl)-3-methoxybenzamide;
N-(3-(2-amino-3-(4-hydroxyphenoxy)phenyl)-3-oxopropyl)-acetamide;
N-(3-(2-amino-3-(4-hydroxyphenoxy)phenyl)-3-oxopropyl)-4-fluorobenzamide;
N-(3-(2-amino-3-(4-hydroxyphenoxy)phenyl)-3-oxopropyl)-cyclohexanecarboxamide;
N-(3-(2-amino-3-(4-hydroxyphenoxy)phenyl)-3-oxopropyl)-(tetrahydro-2H-pyran-4-yl)-carboxamide;
N-(3-(2-amino-3-methoxyphenyl)-3-oxopropyl)-4-hydroxybenzamide;
N-(3-(2-amino-3-hydroxyphenyl)-3-oxopropyl)-4-hydroxybenzamide;
N-(3-(2-amino-3-(4-methylphenoxy)phenyl)-3-oxopropyl)-4-hydroxybenzamide;
N-(3-(2-amino-3-(4-(trifluoromethyl)phenoxy)phenyl)-3-oxopropyl)-4-hydroxybenzamide;
N-(3-(2-amino-3-(3,4-dimethoxyphenoxy)phenyl)-3-oxopropyl)-4-hydroxybenzamide;
N-(3-(2-amino-3-(4-chlorophenoxy)phenyl)-3-oxopropyl)-4-hydroxybenzamide;
N-(3-(2-amino-3-(4-chlorophenoxy)phenyl)-3-oxopropyl)-4-aminobenzamide;
N-(3-(2-amino-3-(4-chlorophenoxy)phenyl)-3-oxopropyl)-4-acetylaminobenzamide;
N-(2-(3-(4-methoxyphenoxy)benzoylamino)ethyl)-4-hydroxybenzamide;
N-(2-(2-(4-methoxyphenoxy)benzoylamino)ethyl)-4-hydroxybenzamide;
N-(4-hydroxyphenyl)-4-(3-(4-chlorophenoxy)phenylamino)-4-oxobutanamide;
N-(3-(3-(4-chlorophenoxy)phenylamino)-3-oxopropyl)-4-hydroxybenzamide;
N-(2-(3-(4-methoxyphenoxy)phenylamino)-2-oxyethyl)-4-hydroxybenzamide;
N-(3-(3-(4-methoxyphenoxy)phenylamino)-3-oxopropyl)-4-hydroxybenzamide;
N-(4-(3-(4-methoxyphenoxy)phenylamino)-4-oxobuthyl)-4-hydroxybenzamide;
N-(2-(2-(4-methoxyphenoxy)phenylamino)-2-oxoethyl)-4-hydroxybenzamide;
N-(3-(2-(4-methoxyphenoxy)phenylamino)-3-oxopropyl)-4-hydroxybenzamide;
N-(3-(4-(4-methoxyphenoxy)phenylamino)-3-oxopropyl)-4-hydroxybenzamide;
N-(3-(4-chlorophenoxy)phenyl)-1-(4-hydroxyphenylcarbonyl)azetidine-3-carboxamide;
N-(3-(4-chlorophenoxy)phenyl)-1-(4-hydroxyphenylcarbonyl)pyrrolidine-3-carboxamide;
N-(3-(4-chlorophenoxy)phenyl)-1-(4-hydroxyphenylcarbonyl)piperidine-3-carboxamide;
N-(3-(4-chlorophenoxy)phenyl)-1-(4-hydroxyphenylcarbonyl)pyrrolidine-2-carboxamide;
N-(3-(3-(4-chlorophenoxy)phenylamino)-3-oxopropyl)thiophene-2-carboxamide;
N-(3-(3-(4-chlorophenoxy)phenylamino)-3-oxopropyl)thiophene-3-carboxamide;
N-(3-(3-(4-chlorophenoxy)phenylamino)-3-oxopropyl)pyridine-4-carboxamide; and
N-(3-(3-(3,4-dichlorophenoxy)phenylamino)-3-oxopropyl)-4-hydroxybenzamide;
or a pharmaceutically acceptable salt thereof.

9. A pharmaceutical composition comprising the compound according to claim 1 or a pharmaceutically acceptable salt thereof and a pharmaceutically acceptable additive.

10. The pharmaceutical composition according to claim 9, wherein the compound according to claim 1 is present in an amount effective for use in the treatment of a disease associated with the enhancement of the osteopontin production.

11. A medicament for treating a disease associated with the enhancement of the osteopontin production, comprising an effective amount of a compound according to claim 1 or a pharmaceutically acceptable salt thereof as an active ingredient.

12. The medicament according to claim 11 wherein the compound is a compound of formula (I):
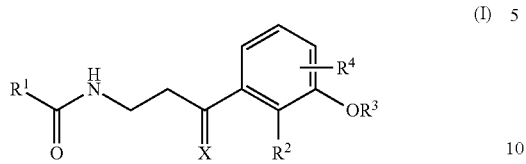
wherein $R^1$, $R^2$, $R^3$, $R^4$, and X are as defined in claim 1.
13. The medicament according to claim 11 wherein the disease is selected from cancer, hepatitis, arteriosclerosis, multiple sclerosis, arthritis, rheumatism, pulmonary fibrosis, osteoporosis, or urolithiasis.
* * * * *